(12) United States Patent
Krieger et al.

(10) Patent No.: US 11,732,268 B2
(45) Date of Patent: Aug. 22, 2023

(54) METHODS AND COMPOSITIONS FOR USE IN GENOME MODIFICATION IN PLANTS

(71) Applicant: MONSANTO TECHNOLOGY LLC, St. Louis, MO (US)

(72) Inventors: Elysia K. Krieger, Kirkwood, MO (US); Richard J. Lawrence, Kirkwood, MO (US); Zarir E. Vaghchhipawala, Madison, WI (US); Jianping Xu, Chesterfield, MO (US); Xudong Ye, Chesterfield, MO (US)

(73) Assignee: Monsanto Technology LLC, St. Louis, MO (US)

(*) Notice: Subject to any disclaimer, the term of this patent is extended or adjusted under 35 U.S.C. 154(b) by 332 days.

(21) Appl. No.: 16/311,749

(22) PCT Filed: Jun. 27, 2017

(86) PCT No.: PCT/US2017/039502
§ 371 (c)(1),
(2) Date: Dec. 20, 2018

(87) PCT Pub. No.: WO2018/005491
PCT Pub. Date: Jan. 4, 2018

(65) Prior Publication Data
US 2019/0211344 A1 Jul. 11, 2019

Related U.S. Application Data

(60) Provisional application No. 62/355,715, filed on Jun. 28, 2016.

(51) Int. Cl.
*C12N 15/82* (2006.01)
(52) U.S. Cl.
CPC ..... *C12N 15/8202* (2013.01); *C12N 15/8205* (2013.01); *C12N 15/8213* (2013.01)
(58) Field of Classification Search
CPC .................................................. C12N 15/8205
See application file for complete search history.

(56) References Cited

U.S. PATENT DOCUMENTS

| | | |
|---|---|---|
| 4,761,373 A | 8/1988 | Anderson et al. |
| 4,810,648 A | 3/1989 | Stalker |
| 5,013,659 A | 5/1991 | Bedbrook et al. |
| 5,015,580 A | 5/1991 | Christou et al. |
| 5,034,322 A | 7/1991 | Rogers et al. |
| 5,094,945 A | 3/1992 | Comai |
| 5,106,739 A | 4/1992 | Comai et al. |
| 5,141,870 A | 8/1992 | Bedbrook et al. |
| 5,159,135 A | 10/1992 | Umbeck |
| 5,188,958 A | 2/1993 | Moloney et al. |
| 5,217,902 A | 6/1993 | Jones et al. |
| 5,229,114 A | 7/1993 | Cregan et al. |
| 5,273,894 A | 12/1993 | Strauch et al. |
| 5,276,268 A | 1/1994 | Strauch et al. |
| 5,322,938 A | 6/1994 | McPherson et al. |
| 5,352,605 A | 10/1994 | Fraley et al. |
| 5,359,142 A | 10/1994 | McPherson et al. |
| 5,362,865 A | 11/1994 | Austin |
| 5,378,619 A | 1/1995 | Rogers |
| 5,378,824 A | 1/1995 | Bedbrook et al. |
| 5,463,174 A | 10/1995 | Moloney et al. |
| 5,463,175 A | 10/1995 | Barry et al. |
| 5,512,466 A | 4/1996 | Klee et al. |
| 5,530,196 A | 6/1996 | Fraley et al. |
| 5,538,880 A | 7/1996 | Lundquist et al. |
| 5,543,576 A | 8/1996 | Van Ooijen et al. |
| 5,550,318 A | 8/1996 | Adams et al. |
| 5,561,236 A | 10/1996 | Leemans et al. |
| 5,591,616 A | 1/1997 | Hiei et al. |
| 5,605,011 A | 2/1997 | Bedbrook et al. |
| 5,608,149 A | 3/1997 | Barry et al. |
| 5,627,061 A | 5/1997 | Barry et al. |
| 5,633,437 A | 5/1997 | Bernasconi et al. |
| 5,633,435 A | 6/1997 | Barry et al. |
| 5,637,489 A | 6/1997 | Strauch et al. |
| 5,641,876 A | 6/1997 | McElroy et al. |
| 5,646,024 A | 7/1997 | Leemans et al. |
| 5,659,122 A | 8/1997 | Austin |
| 5,689,041 A | 11/1997 | Mariani et al. |
| 5,731,179 A | 3/1998 | Komari et al. |
| 5,750,871 A | 5/1998 | Moloney et al. |
| 5,750,876 A | 5/1998 | Barry et al. |
| 5,767,366 A | 6/1998 | Sathasivan et al. |
| 5,824,877 A | 10/1998 | Hinchee et al. |
| 5,837,848 A | 11/1998 | Ely et al. |

(Continued)

FOREIGN PATENT DOCUMENTS

| | | |
|---|---|---|
| EP | 0 154 204 A2 | 9/1985 |
| EP | 0 275 957 A2 | 7/1988 |

(Continued)

OTHER PUBLICATIONS

Matheka et al 2013 BMC Research Notes 6:448, 1-9 (Year: 2013).*
Beurdeley et al., "Compact designer TALENs for efficient genome engineering," *Nature Communications*, 4:1762 (2013).
Bevan et al., "Structure and transcription of the nopaline synthase gene region of T-DNA," *Nucleic Acids Research*, 11:369-385 (1983).
Callis et al., "Heat Inducible Expression of a Chimeric Maize hsp70CAT Gene in Maize Protoplasts" *Plant Physiology*, 88:965-968 (1988).
Carrington and Freed, "Cap-Independent Enhancement of Translation by a Plant Potyvirus 5′ Nontranslated Region" *Journal of Virology*, 64:1590-1597 (1990).
Castle et al., "Discovery an Directed Evolution of a Glyphosate Tolerance Gene," *Science*, 304:1151-1154 (2004).

(Continued)

Primary Examiner — Brent T Page
(74) Attorney, Agent, or Firm — Morrison & Foerster LLP

(57) ABSTRACT

The present disclosure is in the field of plant transformation. The disclosure provides methods for increasing the rate of site-directed integration of a sequence of interest in plants. The disclosure also provides methods for increasing the efficiency of Rhizobiales-mediated plant transformation.

16 Claims, 7 Drawing Sheets

Specification includes a Sequence Listing.

(56) References Cited

U.S. PATENT DOCUMENTS

| | | | |
|---|---|---|---|
| 5,850,019 A | 12/1998 | Maiti et al. | |
| 5,869,720 A | 2/1999 | John | |
| 5,914,451 A | 6/1999 | Martinell et al. | |
| 5,958,745 A | 9/1999 | Gruys et al. | |
| 5,981,834 A | 11/1999 | John et al. | |
| 5,985,605 A | 11/1999 | Cheng et al. | |
| 5,998,700 A | 12/1999 | Lightfoot et al. | |
| 6,002,070 A | 12/1999 | D'Halluin et al. | |
| 6,011,199 A | 1/2000 | Speirs et al. | |
| 6,040,497 A | 3/2000 | Spencer et al. | |
| 6,051,409 A * | 4/2000 | Hansen | C12N 15/8201 435/320.1 |
| 6,051,753 A | 4/2000 | Comai et al. | |
| 6,051,756 A | 4/2000 | Chen et al. | |
| 6,072,103 A | 6/2000 | Wu et al. | |
| 6,080,560 A | 6/2000 | Russell et al. | |
| 6,140,075 A | 10/2000 | Russell et al. | |
| 6,140,078 A | 10/2000 | Sanders et al. | |
| 6,153,812 A | 11/2000 | Fry et al. | |
| 6,160,208 A | 12/2000 | Lundquist et al. | |
| 6,166,292 A | 12/2000 | Osumi et al. | |
| 6,171,640 B1 | 1/2001 | Bringe | |
| 6,175,060 B1 | 1/2001 | Lefebvre et al. | |
| 6,177,611 B1 | 1/2001 | Rice | |
| 6,194,636 B1 | 2/2001 | McElroy et al. | |
| 6,225,105 B1 | 5/2001 | Sathasivan et al. | |
| 6,228,623 B1 | 5/2001 | Asrar et al. | |
| 6,232,526 B1 | 5/2001 | McElroy et al. | |
| 6,252,138 B1 | 6/2001 | Karimi et al. | |
| 6,265,638 B1 | 7/2001 | Bidney et al. | |
| 6,271,443 B1 | 8/2001 | Stalker et al. | |
| 6,294,714 B1 | 9/2001 | Matsinaga et al. | |
| 6,297,056 B1 | 10/2001 | Tulsieram et al. | |
| RE37,543 E | 2/2002 | Krüger et al. | |
| 6,380,462 B1 | 4/2002 | Kridl | |
| 6,380,466 B1 | 4/2002 | Facciotti | |
| 6,384,301 B1 | 5/2002 | Martinell et al. | |
| 6,399,861 B1 | 6/2002 | Anderson et al. | |
| 6,414,222 B1 | 7/2002 | Gengenbach et al. | |
| 6,426,446 B1 | 7/2002 | McElroy et al. | |
| 6,426,447 B1 | 7/2002 | Knauf et al. | |
| 6,429,357 B1 | 8/2002 | McElroy et al. | |
| 6,429,362 B1 | 8/2002 | Crane | |
| 6,433,252 B1 | 8/2002 | Kriz et al. | |
| 6,437,217 B1 | 8/2002 | McElroy et al. | |
| 6,444,876 B1 | 9/2002 | Lassner et al. | |
| 6,459,018 B1 | 10/2002 | Knutzon | |
| 6,476,295 B2 | 11/2002 | Barry et al. | |
| 6,483,008 B1 | 11/2002 | Dehesh et al. | |
| 6,489,461 B1 | 12/2002 | Dehesh et al. | |
| 6,495,739 B1 | 12/2002 | Lassner et al. | |
| 6,531,648 B1 | 3/2003 | Lanahan et al. | |
| 6,537,750 B1 | 3/2003 | Shorrosh | |
| 6,538,178 B1 | 3/2003 | Kishore | |
| 6,538,179 B1 | 3/2003 | Barry et al. | |
| 6,538,181 B1 | 3/2003 | Stalker et al. | |
| 6,541,259 B1 | 4/2003 | Lassner et al. | |
| 6,589,767 B1 | 7/2003 | Knutzon et al. | |
| 6,596,538 B1 | 7/2003 | Lardizabal et al. | |
| 6,603,061 B1 | 8/2003 | Armstrong et al. | |
| 6,613,963 B1 | 9/2003 | Gingera et al. | |
| 6,635,806 B1 | 10/2003 | Kriz et al. | |
| 6,653,530 B1 | 11/2003 | Shewmaker et al. | |
| 6,660,849 B1 | 12/2003 | Dehesh | |
| 6,706,950 B2 | 3/2004 | Dehesh | |
| 6,723,837 B1 | 4/2004 | Karunanandaa et al. | |
| 6,770,465 B1 | 8/2004 | Dehesh et al. | |
| 6,774,283 B1 | 8/2004 | Goodman et al. | |
| 6,812,379 B2 | 11/2004 | Staub | |
| 6,822,141 B2 | 11/2004 | Lardizabal et al. | |
| 6,828,475 B1 | 12/2004 | Metz et al. | |
| 7,029,908 B1 * | 4/2006 | Stuiver | C12N 15/8201 435/320.1 |
| 7,122,722 B2 | 10/2006 | Trolinder et al. | |
| 8,076,536 B2 | 12/2011 | Ye et al. | |
| 8,609,934 B2 * | 12/2013 | Fillatti | C12N 15/8247 800/294 |
| 9,757,089 B2 | 9/2017 | Reichel | |
| 2003/0028917 A1 | 2/2003 | Gruys et al. | |
| 2003/0083480 A1 | 5/2003 | Castle et al. | |
| 2003/0110532 A1 | 6/2003 | Armostrong et al. | |
| 2003/0115626 A1 | 6/2003 | Weeks et al. | |
| 2003/0135879 A1 | 7/2003 | Weeks et al. | |
| 2004/0123342 A1 | 6/2004 | Elliott et al. | |
| 2004/0177399 A1 | 9/2004 | Hammer et al. | |
| 2004/0216189 A1 | 10/2004 | Houmard et al. | |
| 2004/0237142 A1 | 11/2004 | Gilbertson et al. | |
| 2005/0183170 A1 | 8/2005 | Fillatti et al. | |
| 2005/0289672 A1 | 12/2005 | Jefferson | |
| 2006/0070137 A1 * | 3/2006 | Rommens | C12N 15/8201 800/278 |
| 2006/0150286 A1 | 7/2006 | Huang et al. | |
| 2006/0200878 A1 | 9/2006 | Lutfiyya et al. | |
| 2007/0271627 A1 | 11/2007 | Ye et al. | |
| 2012/0156784 A1 * | 6/2012 | Adams, Jr. | C12N 15/8205 435/430 |
| 2015/0013031 A1 | 1/2015 | Gilbertson et al. | |
| 2015/0184171 A1 | 7/2015 | D Halluin | |

FOREIGN PATENT DOCUMENTS

| | | |
|---|---|---|
| EP | 0 385 962 A1 | 9/1990 |
| WO | WO 87/04181 | 7/1987 |
| WO | WO 89/00193 A1 | 1/1989 |
| WO | WO 97/41228 A2 | 11/1997 |
| WO | WO 99/27116 | 6/1999 |
| WO | WO 2004/009761 A2 | 1/2004 |
| WO | WO 2004/074443 A2 | 9/2004 |
| WO | WO 2005/003362 A2 | 1/2005 |
| WO | 2005029944 A2 | 4/2005 |
| WO | 2006036739 A2 | 4/2006 |

OTHER PUBLICATIONS

Cermak et al., "Efficient design and assembly of custom TALEN and other TAL effector-based constructs for DNA targeting," *Nucleic Acids Research*, 39(12):e82 (2011).

Chandler et al., "Two Regulatory Genes of the Maize Anthocyanin Pathway Are Homologous: Isolation of the B Utilizing R Genomic Sequences," *Plant Cell* 1:1175-1183 (1989).

Dekeyser et al., "Evaluate of Selectable Markers for Rice Transformation" *Plant Physiology*, 90:217-223 (1989).

Della-Cioppa et al., "Targeting a Herbicide-Resistant Enzyme from *Escherichia coli* to Chloroplasts of Higher Plants," *Bio/Technology*, 5:579-584 (1987).

Depicker et al., "Nopaline Synthase: Transcript Mapping and DNA Sequence," *Journal of Molecular and Applied Genetics*, 1:561-573 (1982).

Doyle et al., "TAL Effector-Nucleotide Targeter (TALE-NT) 2.0: tools for TAL effector design and target prediction," *Nucleic Acids Research*, 40:W117-W122 (2012).

Ebert et al., "Identification of an essential upstream element in the nopaline synthase promoter by stable and transient assays," *Proc. Natl. Acad. Sci. USA*, 84:5745-5749 (1987).

Fraley et al., "Expression of bacterial genes in plant cells," *Proc. Natl. Acad. Sci. USA*, 80:4803-4807 (1983).

Gabsalilow et al., "Site- and strand-specific nicking of DNA by fusion proteins derived from MutH and I-ScEl or TALE repeats," *Nucleic Acids Research*, 41(7): e83 (2013).

GenBank Accession No. V00087.

Haseloff et al., "Removal of a cryptic intron and subcellular location of green fluorescent protein are required to mark transgenic *Ararbidopsis* plants brightly," *Proc. Natl. Acad. Sci. USA*, 94:2122-2127 (1997).

Katz et al., "Cloning and Expression of the Tyrosinase Gene from *Streptomyces antibioticus* in *Streptomyces lividans*," *J. Gen. Micro.*, 129:2703-2714 (1983).

Kuhlemeier et al., "The Pea rbcS-3A Promoter Mediates Light Responsiveness but not Organ Specificity," *Plant Cell*, 1: 471-478 (1989).

(56) References Cited

OTHER PUBLICATIONS

Lawton et al., "Expression of a soybean β-conclycinin gene under the control of the Cauliflower Mosaic Virus 35S and 19S promoters in transformed petunia tissues," *Plant Molecular Biology*, 9:315-324 (1987).
Marcotte et al., "Abscisic Acid-Responsive Sequences from the Em Gene of Wheat," *Plant Cell*, 1:969-976 (1989).
Odell et al., "Identification of DNA sequences required for activity of the cauliflower mosaic virus 35S promoter," *Nature*, 313:810-812 (1985).
Ow et al., "Transient and Stable Expression of the Firefly Luciferase Gene in Plant Cells and Transgenic Plants," *Science*, 234(4778):856-859 (1986).
Pitzschke and Hirt, "New insights into an old story: *Agrobacterium*-induced tumour formation in plants by plant transformation," *The EMBO Journal*, 29:1021-1032 (2010).
Reichel et al., "Enhanced green fluorescence by the expression of an Aequorea Victoria green fluorescent protein mutant in mono- and dicotyledonous plant cells," *Proc. Natl. Acad. Sci. USA*, 93:5888-5893 (1996).
Schaffner et al., "Maize rbcS Promoter Activity Depends on Sequence Elements Not Found in Dicot rbcS Promoters," *Plant Cell*, 3:997-1012 (1991).
Sheen et al., "Green-fluorescent protein as a new vital marker in plant cells," *The Plant Journal*, 8(5):777-784 (1995).
Siebertz et al., "cis-Analysis of the Wound-Inducible Promoter wun1 in Transgenic Tobacco Plants and Histochemical Localization of Its Expression," *Plant Cell*, 1:961-968 (1989).
Stalker et al., "Herbicide Resistance in Transgenic Plants Expressing a Bacterial Detoxification Gene," *Science*, 242(4877):419-4231 (988).
Sutcliffe, "Nucleotide sequence of the ampicillin resistance gene of *Escherichia coli* plasmid pBR322," *Proc. Natl. Acad. Sci. USA*, 75(8):3737-3741 (1978).
Thillet et al., "Site-directed Mutagenesis of Mouse Dihydrofolate Reductase: Mutants With Increased Resistance to Methotrexate and Trimethoprim," 263(25):12500-12508 (1988).
Thompson et al., "CLUSTAL W: improving the sensitivity of progressive multiple sequence alignment through sequence weighting, position-specific gap penalties and weight matrix choice," *Nucl. Acids Res.*, 22(22):4673-4680 (1994).
Yang and Russell, "Maize sucrose synthase-1 promoter directs phloem cell-specific expression of Gus gene in transgenic tobacco plants," *Proc. Natl. Acad. Sci. USA*, 87:4144-4148 (1990).
Yanik et al., "TALE-PvuII Fusion Proteins—Novel Tools for Gene Targeting," *PLoS One*, 8: e82539, 1-13.
Caribe Dos Santos, A. C. et al. (Jun. 2009, e-pub. Jul. 12, 2009) "DsRNA-induced Gene Silencing in Moniliophthora Perniciosa, the Causal Agent of Witches' Broom Disease of Cacao," Fungal Genetics and Biology 46(11): 825-836.
International Search Report and Written Opinion, dated Sep. 25, 2017, for PCT Application No. PCT/US2017/039502, filed Jun. 27, 2017, 26 pages.
Mette, M. F. et al. (Oct. 2, 2000). "Transcriptional Silencing and Promoter Methylation Triggered by Double-stranded RNA," The EMBO Journal 19(19): 5194-5201.
Dauvillee, D. et al. (2004). "Minimal Extent of Sequence Homology Required for Homologous Recombination at the PsbA Locus in Chlamydomonas Reinhardtii Chloroplasts Using PCR-Generated DNA Fragments," Photosynthesis Research 79:219-224.

\* cited by examiner

METHODS AND COMPOSITIONS FOR USE IN GENOME MODIFICATION IN PLANTS

CROSS-REFERENCE TO RELATED APPLICATIONS PRIORITY-CLAIM AND INCORPORATION OF SEQUENCE LISTING

This application is a U.S. National Phase of PCT/US2017/039502, filed Jun. 27, 2017, which claims priority to U.S. Provisional Application No. 62/355,715, filed Jun. 28, 2016, both of which are incorporated by reference in their entireties herein. A sequence listing contained in the file named "P34339US01_SEQ.TXT" which is 34,637 bytes (measured in MS-Windows®) and created on Dec. 19, 2018 is filed electronically herewith and incorporated by reference in its entirety.

FIELD

This disclosure relates to the field of plant transformation. Methods of, and compositions for, transfer of T-strands of DNA from *Agrobacterium* plasmids are provided. Also provided are methods of, and compositions for, using *Agrobacterium*-mediated transfer of T-strands of DNA to promote templated gene editing and site-directed integration of transgenes. Also provided are methods for increasing the efficiency of *Agrobacterium*-mediated transformation. Non-*Agrobacterium*-mediated transformation methods and compositions are also provided.

BACKGROUND

*Agrobacterium*-mediated transformation utilizes *Agrobacterium tumefaciens* to transfer single-stranded DNA synthesized from recombinant plasmids to plant cells. Transformation of plant cells often requires co-culturing with *A. tumefaciens*. A DNA sequence of interest is incorporated into specially-constructed DNA plasmids where the DNA sequence of interest is flanked by an *Agrobacterium* tumor-inducing (Ti) plasmid right border DNA region and a left border DNA region. The *Agrobacterium*-mediated transformation process initiates when an endonuclease, VirD2, nicks the DNA plasmid at the right border and left border regions to release a single-stranded transfer DNA (also called the T-strand). The T-strand transfers transgenes situated between the right and left borders into the targeted plant cells, where the T-strand can integrate into the genome (see, for example, U.S. Pat. No. 5,034,322; Pitzschke and Hirt. *The EMBO Journal* (2010) 29: 1021-1032). The right border, but not the left border, is essential for successful transformation of plant cells (see Wang et al. *Cell* (1984) 38:455-462; and van Haaren et al. *Plant Molecular Biology* (1987) 8: 95-104). Plant cells that have been transformed via *Agrobacterium*-mediated transformation can be manipulated to regenerate into a whole, fertile plant.

Successful *Agrobacterium*-mediated transformation of a plant cell typically results in a random integration in the plant genome. Such random integrations can have deleterious effects to the plant cell if the transgene inserts into an essential endogenous gene. Similarly, such random integrations can have a deleterious effect on expression of the transgene due to position effects of the chromosome where the transgene inserted. There exists a need in the art for an *Agrobacterium*-mediated transformation method for plant cells that promotes templated gene editing and site-directed integration of transgenes.

SUMMARY

In one aspect, the present disclosure provides a method of transforming a plant cell, comprising contacting the plant cell with a Rhizobiales cell capable of transforming the plant cell, where the Rhizobiales cell comprises at least one vector capable of forming two T-strands that are essentially complementary in at least a portion of the T-strands. In a further aspect, the at least one vector comprises a first right border DNA sequence (RB1), a second right border DNA sequence (RB2), and at least one sequence of interest, and the RB1 is positioned in the vector to initiate synthesis of a first T-strand such that the sequence of interest is in the sense orientation from the 5' to 3' end of the first T-strand; and the RB2 is positioned in the vector to initiate synthesis of a second T-strand such that the sequence of interest is in the anti-sense orientation relative to the sequence of interest in the first T-strand, and the two T-strands resulting from initiation at RB1 and RB2 are essentially complementary in at least a portion of the sequence of interest. In an alternative further aspect, the at least one vector comprises a RB1, a RB2, a sequence of interest, a first left border DNA sequence (LB1) and a second left border DNA sequence (LB2), where the vector is configured such that the RB1 is paired with the LB1 which are positioned in the vector to initiate (RB1) and terminate (LB1) synthesis of a first T-strand such that the sequence of interest is in the sense orientation from the 5' to 3' end of the first T-strand; and the RB2 is paired with the LB2 which are positioned in the vector to initiate (RB2) and terminate (LB2) synthesis of a second T-strand such that the sequence of interest is in an anti-sense orientation relative to the sequence of interest in the first T-strand, and where the two T-strands resulting from initiation at RB1 and RB2 are essentially complementary in at least a portion of the sequence of interest. In another alternative further aspect, the vector comprises a first sequence of interest and a second sequence of interest, where the first sequence of interest is essentially identical to the second sequence of interest, where the vector further comprises a RB1 and a LB1 which are positioned in the vector to initiate (RB1) and terminate (LB1) synthesis of a first T-strand such that the first sequence of interest is in the sense orientation from the 5' to 3' end of the first T-strand, and the vector further comprises a RB2 and a LB2 which are positioned in the vector to initiate (RB2) and terminate (LB2) synthesis of a second T-strand such that the second sequence of interest is in an anti-sense orientation relative to the first sequence of interest in the first T-strand, and where the two T-strands resulting from initiation at RB1 and RB2 are essentially complementary in at least a portion of the first sequence of interest and the second sequence of interest. In yet another alternative further aspect, the Rhizobiales cell comprises at least a first vector and a second vector, where each vector comprises essentially identical sequences of interest, and where the first vector comprises a RB1 and a LB1 which are positioned in the first vector to initiate (RB1) and terminate (LB1) synthesis of a first T-strand such that the sequence of interest is in the sense orientation from the 5' to 3' end of the first T-strand; and where the second vector comprises a RB2 and a LB2) which are positioned in the second vector to initiate (RB2) and terminate (LB2) synthesis of a second T-strand such that the sequence of interest is in an anti-sense orientation relative to the sequence of interest in the first T-strand, and where the two T-strands resulting from initiation at RB1 and RB2 are essentially complementary in at least a portion of the sequence of interest. In another alternative further aspect, the vector comprises a first sequence of interest, a second sequence of interest different from the first sequence of interest, at least two RB DNA sequences, and one or more optional LB DNA sequences, wherein the first RB DNA sequence (RB1) and a first LB DNA sequence (LB1) are positioned in the vector to initiate (RB1) and terminate (LB1) synthesis of the first T-strand such that the first sequence of interest is in the sense orientation from the 5' to 3' end of the first T-strand; and the vector configuration further comprises a second RB DNA sequence (RB2) and a second LB DNA sequence (LB2) which are positioned in the vector to initiate (RB2) and terminate (LB2) synthesis of a second T-strand such that the first sequence of interest is in an anti-sense orientation from the 5' to 3' end of the second T-strand, wherein the two T-strands resulting from initiation at RB1 and RB2 are essentially complementary to each other in at least a portion of the first sequence of interest, and wherein the vector configuration further comprises a third RB DNA sequence (RB3) and a third LB DNA sequence (LB3) which are positioned in the vector to initiate (RB3) and terminate (LB3) synthesis of a third T-strand such that the second sequence of interest is in the sense orientation from the 5' to 3' end of the third T-strand; and the vector configuration further comprises a fourth RB DNA sequence (RB4) and a fourth LB DNA sequence (LB4) which are positioned in the vector to initiate (RB4) and terminate (LB4) synthesis of a fourth T-strand such that the second sequence of interest is in an anti-sense orientation from the 5' to 3' end of the fourth T-strand, and the two T-strands resulting from initiation at RB3 and RB4 are essentially complementary to each other in at least a portion of the second sequence of interest. In some embodiments, RB1 is 5' to LB2. In some embodiments, RB1 is 3' to LB2. In some embodiments, RB2 is 5' to LB1. In some embodiments, RB2 is 3' to LB1.

In one aspect, the instant disclosure provides a method of transforming a plant cell, comprising contacting the plant cell with two or more Rhizobiales cells capable of transforming the plant cell, where the two or more Rhizobiales cells each contain one of at least two vectors capable of forming two essentially complementary T-strands. In a further aspect, each vector comprises an essentially identical sequence of interest, and where the first vector comprises a first right border DNA sequence (RB1), and where the RB1 is positioned in the vector to initiate synthesis of a first T-strand such that the sequence of interest is in the sense orientation from the 5' to 3' end of the first T-strand; and the second vector comprises a second right border DNA sequence (RB2) which is positioned in the vector to initiate synthesis of a second T-strand such that the sequence of interest is in the anti-sense orientation relative to the sequence of interest in the first T-strand, and where the two T-strands resulting from initiation at RB1 and RB2 are essentially complementary in at least a portion of the sequence of interest. In an alternative further aspect, each vector comprises an essentially identical sequence of interest, and where the first vector comprises a RB1 and a first left border DNA sequence (LB1) which are positioned in the first vector to initiate (RB1) and terminate (LB1) synthesis of a first T-strand such that the sequence of interest is in the sense orientation from the 5' to 3' end of the first T-strand; and the second vector comprises a RB2 and a second left border DNA sequence (LB2) which are positioned in the second vector to initiate (RB2) and terminate (LB2) synthesis of a second T-strand such that the sequence of interest is in an anti-sense orientation from the 5' to 3' end of the second T-strand, and where the sequence of interest in the two T-strands resulting from initiation at RB1 and RB2 are essentially complementary to each other. In some embodiments, RB1 is 5' to LB2. In some embodiments, RB1 is 3' to LB2. In some embodiments, RB2 is 5' to LB1. In some embodiments, RB2 is 3' to LB1.

In one aspect, the instant disclosure provides a method of increasing the rate of site directed integration of a sequence of interest, comprising contacting a plant cell with at least one vector capable of forming two essentially complementary T-strands. In a further aspect, the at least one vector comprises a first right border DNA sequence (RB1), a second right border DNA sequence (RB2), and at least one sequence of interest, where the RB1 is positioned in the vector to initiate synthesis of a first T-strand such that the sequence of interest is in the sense orientation from the 5' to 3' end of the first T-strand; and the RB2 is positioned in the vector to initiate synthesis of a second T-strand such that the sequence of interest is in the anti-sense orientation relative to the sequence of interest in the first T-strand, and where the two T-strands resulting from initiation at RB1 and RB2 are essentially complementary in at least a portion of the sequence of interest. In an alternative further aspect, the at least one vector comprises a RB1, a RB2, a sequence of interest, a first left border DNA sequence (LB1), a second left border DNA sequence (LB2) and where the vector is configured such that the RB1 is paired with the LB1 which are positioned in the vector to initiate (RB1) and terminate (LB1) synthesis of a first T-strand such that the sequence of interest is in the sense orientation from the 5' to 3' end of the first T-strand; and the RB2 is paired with the LB2 which are positioned in the vector to initiate (RB2) and terminate (LB2) synthesis of a second T-strand such that the sequence of interest is in an anti-sense orientation relative to the sequence of interest in the first T-strand, and where the sequence of interest in the two T-strands resulting from initiation at RB1 and RB2 are essentially complementary in at least a portion of the sequence of interest. In another alternative further aspect, the vector comprises a first sequence of interest and a second sequence of interest, where the first sequence of interest is essentially identical to the second sequence of interest; where the vector further comprises a RB1 and a LB1 which are positioned in the vector to initiate (RB1) and terminate (LB1) synthesis of a first T-strand such that the first sequence of interest is in the sense orientation from the 5' to 3' end of the first T-strand; and the vector further comprises a RB2 and a LB2 which are positioned in the vector to initiate (RB2) and terminate (LB2) synthesis of a second T-strand such that the second sequence of interest is in an anti-sense orientation relative to the first sequence of interest in the first T-strand, and where the two T-strands resulting from initiation at RB1 and RB2 are essentially complementary in at least a portion of the first sequence of interest and the second sequence of interest. In yet another alternative further aspect, the Rhizobiales cell comprises at least a first and a second vector, where each vector comprises essentially identical sequences of interest, and where the first vector comprises a RB1 and a LB1 which are positioned in the first vector to initiate (RB1) and terminate (LB1) synthesis of a first T-strand such that the sequence of interest is in the sense orientation from the 5' to 3' end of the first T-strand; and the second vector comprises a RB2 and a LB2 which are positioned in the second vector to initiate (RB2) and terminate (LB2) synthesis of a second T-strand such that the sequence of interest is in an anti-sense orientation relative to the sequence of interest in the first T-strand, and where the two T-strands resulting from initiation at RB1 and RB2 are essentially complementary in at least a portion of the sequence of interest. In another alternative further aspect, the vector comprises a first sequence of interest, a second sequence of interest different from the first sequence of interest, at least two RB DNA sequences, and one or more optional LB DNA sequences, wherein the first RB DNA sequence (RB1) and a first LB DNA sequence (LB1) are positioned in the vector to initiate (RB1) and terminate (LB1) synthesis of the first T-strand such that the first sequence of interest is in the sense orientation from the 5' to 3' end of the first T-strand; and the vector configuration further comprises a second RB DNA sequence (RB2) and a second LB DNA sequence (LB2) which are positioned in the vector to initiate (RB2) and terminate (LB2) synthesis of a second T-strand such that the first sequence of interest is in an anti-sense orientation from the 5' to 3' end of the second T-strand, wherein the two T-strands resulting from initiation at RB1 and RB2 are essentially complementary to each other in at least a portion of the first sequence of interest, and wherein the vector configuration further comprises a third RB DNA sequence (RB3) and a third LB DNA sequence (LB3) which are positioned in the vector to initiate (RB3) and terminate (LB3) synthesis of a third T-strand such that the second sequence of interest is in the sense orientation from the 5' to 3' end of the third T-strand; and the vector configuration further comprises a fourth RB DNA sequence (RB4) and a fourth LB DNA sequence (LB4) which are positioned in the vector to initiate (RB4) and terminate (LB4) synthesis of a fourth T-strand such that the second sequence of interest is in an anti-sense orientation from the 5' to 3' end of the fourth T-strand, and the two T-strands resulting from initiation at RB3 and RB4 are essentially complementary to each other in at least a portion of the second sequence of interest. In some embodiments, RB1 is 5' to LB2. In some embodiments, RB1 is 3' to LB2. In some embodiments, RB2 is 5' to LB1. In some embodiments, RB2 is 3' to LB1.

In one aspect, the instant disclosure provides a method of increasing the rate of site directed integration of a sequence of interest, comprising contacting a plant cell with two or more Rhizobiales cells, where the two or more Rhizobiales cells each contain one of at least two vectors capable of forming two essentially complementary T-strands. In a further aspect, each vector comprises an essentially identical sequence of interest, and where the first vector comprises a first right border DNA sequence (RB1), and where the RB1 is positioned in the vector to initiate synthesis of a first T-strand such that the sequence of interest is in the sense orientation from the 5' to 3' end of the first T-strand; and the second vector comprises a second right border DNA sequence (RB2) which is positioned in the vector to initiate synthesis of a second T-strand such that the sequence of interest is in the anti-sense orientation relative to the sequence of interest in the first T-strand, and where the two T-strands resulting from initiation at RB1 and RB2 are essentially complementary in at least a portion of the sequence of interest. In an alternative further aspect, each vector comprises an essentially identical sequence of interest, and where the first vector comprises a RB1 and a first left border (LB1) which are positioned in the first vector to initiate (RB1) and terminate (LB1) synthesis of a first T-strand such that the sequence of interest is in the sense orientation from the 5' to 3' end of the first T-strand; and the second vector comprises a RB2 and a second left border (LB2) which are positioned in the second vector to initiate (RB2) and terminate (LB2) synthesis of a second T-strand such that the sequence of interest is in an anti-sense orientation from the 5' to 3' end of the second T-strand, and where the sequence of interest in the two T-strands resulting from initiation at RB1 and RB2 are essentially complementary to each other. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof. In some embodiments, RB1 is 5' to LB2. In some embodiments, RB1 is 3' to LB2. In some embodiments, RB2 is 5' to LB1. In some embodiments, RB2 is 3' to LB1.

In one aspect, the instant disclosure provides a method of transforming a plant cell, comprising contacting the plant cell with a Rhizobiales cell capable of transforming the plant cell, where the Rhizobiales cell comprises at least one vector comprising a right border DNA sequence (RB) and a left border DNA sequence (LB) and where the vector comprises between the RB and LB: (i) a first sequence of interest in a sense orientation relative to the RB, (ii) a spacer, and (iii) a second sequence of interest in an anti-sense orientation relative to the RB, where the first sequence of interest and second sequence of interest are essentially complementary and after synthesis of the T-strand anneal to form a double-stranded DNA. In some embodiments, the Rhizobiales cell is selected from an *Agrobacterium* spp., a *Bradyrhizobium* spp., a *Mesorhizobium* spp., an Ochrobactrum spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof.

In one aspect, the instant disclosure provides a method of increasing the rate of site directed integration of a double-stranded DNA into a genome of a plant cell, comprising contacting the plant cell with at least one vector comprising a right border DNA sequence (RB) and a left border DNA sequence (LB), where the vector comprises between the RB and LB: (i) a first sequence of interest in a sense orientation relative to the RB, (ii) a spacer, and (iii) a second sequence of interest in an anti-sense orientation relative to the RB, where the first sequence of interest and second sequence of interest are essentially complementary and after synthesis of the T-anneal, where the double-stranded DNA is integrated into a genome of a plant cell.

In one aspect, the instant disclosure provides an *Agrobacterium* cell comprising at least one vector that is capable of forming two essentially complementary T-strands.

In one aspect, the instant disclosure provides an *Agrobacterium* cell comprising at least one vector comprising a right border DNA sequence (RB) and a left border DNA sequence (LB) and where the vector comprises between the RB and LB: (i) a first sequence of interest in a sense orientation relative to the RB, (ii) a spacer, and (iii) a second sequence of interest in an anti-sense orientation relative to the RB, where the first sequence of interest and second sequence of interest are essentially complementary, and after synthesis of the T-strand anneal to form a double-stranded DNA.

In one aspect, the instant disclosure provides a method of transforming a plant genome, comprising contacting at least one plant cell on a co-culture medium for at least 2 days, with at least one Rhizobiales cell capable of transforming the plant cell, where the Rhizobiales cell comprises at least one vector capable of forming two essentially complementary T-strands. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof.

In one aspect, the instant disclosure provides a method of transforming a plant genome, comprising contacting at least one plant cell on a co-culture medium for at least 2 days, with at least one Rhizobiales cell capable of transforming the plant cell, where the Rhizobiales cell comprises at least one vector comprising a right border (RB) DNA sequence and a left border (LB) DNA sequence and where the vector further comprises between the RB and LB DNA sequences: (i) a first sequence of interest in a sense orientation relative to the RB DNA sequence, and (ii) a spacer, and (iii) a second sequence of interest in an anti-sense orientation relative to the RB DNA sequence, where the first sequence of interest and second sequence of interest are essentially complementary, and after synthesis of the T-strand anneal to form a double-stranded DNA. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof.

In one aspect, the instant disclosure provides a method of transforming a plant genome, comprising contacting at least one plant cell on a co-culture medium for at least 3 days, with at least one Rhizobiales cell capable of transforming the plant cell, where the Rhizobiales cell comprises at least one vector capable of forming two essentially complementary T-strands. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof.

In one aspect, the instant disclosure provides a method of transforming a plant genome, comprising contacting at least one plant cell on a co-culture medium for at least 3 days, with at least one Rhizobiales cell capable of transforming the plant cell, where the Rhizobiales cell comprises at least one vector comprising a right border (RB) DNA sequence and a left border (LB) DNA sequence and where the vector further comprises between the RB and LB DNA sequences: (i) a first sequence of interest in a sense orientation relative to the RB DNA sequence, and (ii) a spacer, and (iii) a second sequence of interest in an anti-sense orientation relative to the RB DNA sequence, where the first sequence of interest and second sequence of interest are essentially complementary, and after synthesis of the T-strand anneal to form a double-stranded DNA. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof.

Several embodiments relate to a method of providing a sequence of interest to a plant cell, comprising contacting the plant cell with a Rhizobiales cell capable of transforming the plant cell, wherein the Rhizobiales cell comprises at least one vector capable of forming two T-strands that are essentially complementary in at least a portion of the T-strands, wherein the at least one vector comprises a first right border DNA sequence (RB1), a second right border DNA sequence (RB2), and at least one sequence of interest, and wherein the RB1 is positioned in the vector to initiate synthesis of a first T-strand such that the sequence of interest is in the sense orientation from the 5' to 3' end of the first T-strand; and the RB2 is positioned in the vector to initiate synthesis of a second T-strand such that the sequence of interest is in the anti-sense orientation relative to the sequence of interest in the first T-strand, and wherein the two T-strands resulting from initiation at RB1 and RB2 are essentially complementary in at least a portion of the sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell. In some embodiments, the Rhizobiales cell is selected from an *Agrobacterium* spp., a *Bradyrhizobium* spp., a *Mesorhizobium* spp., an *Ochrobactrum* spp., a *Phyllobacte-*

*rium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof.

A method of providing a sequence of interest to a plant cell, comprising contacting the plant cell with a Rhizobiales cell capable of transforming the plant cell, wherein the Rhizobiales cell comprises at least one vector capable of forming two T-strands that are essentially complementary in at least a portion of the T-strands, wherein the at least one vector comprises a RB1, a RB2, a sequence of interest, a first left border DNA sequence (LB1) and a second left border DNA sequence (LB2), wherein the vector is configured such that the RB1 is paired with the LB1 which are positioned in the vector to initiate (RB1) and terminate (LB1) synthesis of a first T-strand such that the sequence of interest is in the sense orientation from the 5' to 3' end of the first T-strand; and the RB2 is paired with the LB2 which are positioned in the vector to initiate (RB2) and terminate (LB2) synthesis of a second T-strand such that the sequence of interest is in an anti-sense orientation relative to the sequence of interest in the first T-strand, and wherein the two T-strands resulting from initiation at RB1 and RB2 are essentially complementary in at least a portion of the sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring anti-sense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell.

A method of providing a sequence of interest to a plant cell, comprising contacting the plant cell with a Rhizobiales cell capable of transforming the plant cell, wherein the Rhizobiales cell comprises at least one vector capable of forming two T-strands that are essentially complementary in at least a portion of the T-strands, wherein the vector comprises a first sequence of interest and a second sequence of interest, wherein the first sequence of interest is essentially identical to the second sequence of interest; wherein the vector further comprises a RB1 and a LB1 which are positioned in the vector to initiate (RB1) and terminate (LB1) synthesis of a first T-strand such that the first sequence of interest is in the sense orientation from the 5' to 3' end of the first T-strand; and the vector further comprises a RB2 and a LB2 which are positioned in the vector to initiate (RB2) and terminate (LB2) synthesis of a second T-strand such that the second sequence of interest is in an anti-sense orientation relative to the first sequence of interest in the first T-strand, and wherein the two T-strands resulting from initiation at RB1 and RB2 are essentially complementary in at least a portion of the first sequence of interest and the second sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof.

A method of providing a sequence of interest to a plant cell, comprising contacting the plant cell with a Rhizobiales cell capable of transforming the plant cell, wherein the Rhizobiales cell comprises at least one vector capable of forming two T-strands that are essentially complementary in at least a portion of the T-strands, wherein the Rhizobiales cell comprises at least a first vector and a second vector, wherein each vector comprises essentially identical sequences of interest, and wherein the first vector comprises a RB1 and a LB1 which are positioned in the first vector to initiate (RB1) and terminate (LB1) synthesis of a first T-strand such that the sequence of interest is in the sense orientation from the 5' to 3' end of the first T-strand; and wherein the second vector comprises a RB2 and a LB2) which are positioned in the second vector to initiate (RB2) and terminate (LB2) synthesis of a second T-strand such that the sequence of interest is in an anti-sense orientation relative to the sequence of interest in the first T-strand, and wherein the two T-strands resulting from initiation at RB1 and RB2 are essentially complementary in at least a portion of the sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring anti-sense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof.

A method of providing a sequence of interest to a plant cell, comprising contacting the plant cell with a Rhizobiales cell capable of transforming the plant cell, wherein the Rhizobiales cell comprises at least one vector capable of forming two T-strands that are essentially complementary in at least a portion of the T-strands, wherein the at least one vector comprises a first sequence of interest, a second sequence of interest different from the first sequence of interest, at least two RB DNA sequences, and one or more optional LB DNA sequences, wherein the first RB DNA sequence (RB1) and a first LB DNA sequence (LB1) are positioned in the vector to initiate (RB1) and terminate (LB1) synthesis of the first T-strand such that the first sequence of interest is in the sense orientation from the 5' to 3' end of the first T-strand; and the vector configuration further comprises a second RB DNA sequence (RB2) and a second LB DNA sequence (LB2) which are positioned in the vector to initiate (RB2) and terminate (LB2) synthesis of a second T-strand such that the first sequence of interest is in an anti-sense orientation from the 5' to 3' end of the second T-strand, wherein the two T-strands resulting from initiation at RB1 and RB2 are essentially complementary to each other in at least a portion of the first sequence of interest, and wherein the vector configuration further comprises a third RB DNA sequence (RB3) and a third LB DNA sequence (LB3) which are positioned in the vector to initiate (RB3) and terminate (LB3) synthesis of a third T-strand such that the second sequence of interest is in the sense orientation from the 5' to 3' end of the third T-strand; and the vector configuration further comprises a fourth RB DNA sequence (RB4) and a fourth LB DNA sequence (LB4) which are positioned in the vector to initiate (RB4) and terminate (LB4) synthesis of a fourth T-strand such that the second sequence of interest is in an anti-sense orientation from the 5' to 3' end of the fourth T-strand, and the two T-strands resulting from initiation at RB3 and RB4 are essentially complementary to each other in at least a portion of the second sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell.

Several embodiments relate to a method of transforming a plant cell, comprising contacting the plant cell with two or more Rhizobiales cells capable of transforming the plant cell, wherein the two or more Rhizobiales cells each contain one of at least two vectors capable of forming two essentially complementary T-strands, wherein each vector comprises an essentially identical sequence of interest, and where the first vector comprises a first right border DNA sequence (RB1), and wherein the RB1 is positioned in the vector to initiate synthesis of a first T-strand such that the sequence of interest is in the sense orientation from the 5' to 3' end of the first T-strand; and the second vector comprises a second right border DNA sequence (RB2) which is positioned in the vector to initiate synthesis of a second T-strand such that the sequence of interest is in the anti-sense orientation relative to the sequence of interest in the first T-strand, and wherein the two T-strands resulting from initiation at RB1 and RB2 are essentially complementary in at least a portion of the sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring anti-sense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell.

Several embodiments relate to a method of transforming a plant cell, comprising contacting the plant cell with two or more Rhizobiales cells capable of transforming the plant cell, wherein the two or more Rhizobiales cells each contain one of at least two vectors capable of forming two essentially complementary T-strands, wherein each vector comprises an essentially identical sequence of interest, and where the first vector comprises a RB1 and a first left border DNA sequence (LB1) which are positioned in the first vector to initiate (RB1) and terminate (LB1) synthesis of a first T-strand such that the sequence of interest is in the sense orientation from the 5' to 3' end of the first T-strand; and the second vector comprises a RB2 and a second left border DNA sequence (LB2) which are positioned in the second vector to initiate (RB2) and terminate (LB2) synthesis of a second T-strand such that the sequence of interest is in an anti-sense orientation from the 5' to 3' end of the second T-strand, and wherein the sequence of interest in the two T-strands resulting from initiation at RB1 and RB2 are essentially complementary to each other. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof.

Several embodiments relate to a method of increasing the rate of site directed integration of a sequence of interest, comprising contacting a plant cell with at least one vector capable of forming two essentially complementary T-strands, wherein the at least one vector comprises a first right border DNA sequence (RB1), a second right border DNA sequence (RB2), and at least one sequence of interest, wherein the RB1 is positioned in the vector to initiate synthesis of a first T-strand such that the sequence of interest is in the sense orientation from the 5' to 3' end of the first T-strand; and the RB2 is positioned in the vector to initiate synthesis of a second T-strand such that the sequence of interest is in the anti-sense orientation relative to the sequence of interest in the first T-strand, and wherein the two T-strands resulting from initiation at RB1 and RB2 are essentially complementary in at least a portion of the sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding sit-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring anti-sense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell.

Several embodiments relate to a method of increasing the rate of site directed integration of a sequence of interest, comprising contacting a plant cell with at least one vector capable of forming two essentially complementary T-strands, wherein the at least one vector comprises a RB1, a RB2, a sequence of interest, a first left border DNA sequence (LB1), a second left border DNA sequence (LB2) and wherein the vector is configured such that the RB1 is paired with the LB1 which are positioned in the vector to initiate (RB1) and terminate (LB1) synthesis of a first T-strand such that the sequence of interest is in the sense orientation from the 5' to 3' end of the first T-strand; and the RB2 is paired with the LB2 which are positioned in the vector to initiate (RB2) and terminate (LB2) synthesis of a second T-strand such that the sequence of interest is in an anti-sense orientation relative to the sequence of interest in the first T-strand, and wherein the sequence of interest in the two T-strands resulting from initiation at RB1 and RB2 are essentially complementary in at least a portion of the sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring anti-sense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell.

Several embodiments relate to a method of increasing the rate of site directed integration of a sequence of interest, comprising contacting a plant cell with at least one vector capable of forming two essentially complementary T-strands, wherein the vector comprises a first sequence of interest and a second sequence of interest, wherein the first sequence of interest is essentially identical to the second sequence of interest; wherein the vector further comprises a RB1 and a LB1 which are positioned in the vector to initiate (RB1) and terminate (LB1) synthesis of a first T-strand such that the first sequence of interest is in the sense orientation from the 5' to 3' end of the first T-strand; and the vector further comprises a RB2 and aLB2 which are positioned in the vector to initiate (RB2) and terminate (LB2) synthesis of a second T-strand such that the second sequence of interest is in an anti-sense orientation relative to the first sequence of interest in the first T-strand, and wherein the two T-strands resulting from initiation at RB1 and RB2 are essentially complementary in at least a portion of the first sequence of interest and the second sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring anti-sense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell.

Several embodiments relate to a method of increasing the rate of site directed integration of a sequence of interest, comprising contacting a plant cell with at least one vector capable of forming two essentially complementary T-strands, wherein the Rhizobiales cell comprises at least a first and a second vector, wherein each vector comprises essentially identical sequences of interest, and wherein the first vector comprises a RB1 and a LB1 which are positioned in the first vector to initiate (RB1) and terminate (LB1) synthesis of a first T-strand such that the sequence of interest is in the sense orientation from the 5' to 3' end of the first T-strand; and the second vector comprises a RB2 and a LB2 which are positioned in the second vector to initiate (RB2) and terminate (LB2) synthesis of a second T-strand such that the sequence of interest is in an anti-sense orientation relative to the sequence of interest in the first T-strand, and wherein the two T-strands resulting from initiation at RB1 and RB2 are essentially complementary in at least a portion of the sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell.

Several embodiments relate to a method of increasing the rate of site directed integration of a sequence of interest, comprising contacting a plant cell with at least one vector capable of forming two essentially complementary T-strands, wherein the at least one vector comprises a first sequence of interest, a second sequence of interest different from the first sequence of interest, at least two RB DNA sequences, and one or more optional LB DNA sequences, wherein the first RB DNA sequence (RB1) and a first LB DNA sequence (LB1) are positioned in the vector to initiate (RB1) and terminate (LB1) synthesis of the first T-strand such that the first sequence of interest is in the sense orientation from the 5' to 3' end of the first T-strand; and the vector configuration further comprises a second RB DNA sequence (RB2) and a second LB DNA sequence (LB2) which are positioned in the vector to initiate (RB2) and terminate (LB2) synthesis of a second T-strand such that the first sequence of interest is in an anti-sense orientation from the 5' to 3' end of the second T-strand, wherein the two T-strands resulting from initiation at RB1 and RB2 are essentially complementary to each other in at least a portion of the first sequence of interest, and wherein the vector configuration further comprises a third RB DNA sequence (RB3) and a third LB DNA sequence (LB3) which are positioned in the vector to initiate (RB3) and terminate (LB3) synthesis of a third T-strand such that the second sequence of interest is in the sense orientation from the 5' to 3' end of the third T-strand; and the vector configuration further comprises a fourth RB DNA sequence (RB4) and a fourth LB DNA sequence (LB4) which are positioned in the vector to initiate (RB4) and terminate (LB4) synthesis of a fourth T-strand such that the second sequence of interest is in an anti-sense orientation from the 5' to 3' end of the fourth T-strand, and the two T-strands resulting from initiation at RB3 and RB4 are essentially complementary to each other in at least a portion of the second sequence of interest. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring anti-sense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell.

Several embodiments relate to a method of transforming a plant cell, comprising contacting the plant cell with a Rhizobiales cell capable of transforming the plant cell, wherein the Rhizobiales cell comprises at least one vector comprising a right border DNA sequence (RB) and a left border DNA sequence (LB) and wherein the vector comprises between the RB and LB: (i) a first sequence of interest in a sense orientation relative to the RB, (ii) a spacer, and (iii) a second sequence of interest in an anti-sense orientation relative to the RB, wherein the first sequence of interest and second sequence of interest are essentially complementary and after synthesis of the T-strand anneal to form a double-stranded DNA. In some embodiments, the first sequence of interest further comprises a first left homology arm DNA sequence and a first right homology arm DNA sequence, and the second sequence of interest further comprises a second left homology arm DNA sequence and a second right homology arm DNA sequence. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring anti-sense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell.

Several embodiments relate to a method of increasing the rate of site directed integration of a double-stranded DNA into a genome of a plant cell, comprising contacting the plant cell with at least one vector comprising a right border DNA sequence (RB) and a left border DNA sequence (LB), wherein the vector comprises between the RB and LB: (i) a first sequence of interest in a sense orientation relative to the RB, (ii) a spacer, and (iii) a second sequence of interest in an anti-sense orientation relative to the RB, wherein the first sequence of interest and second sequence of interest are essentially complementary and after synthesis of the T-strand anneal to form a double-stranded DNA. In some embodiments, the first sequence of interest further comprises a first left homology arm DNA sequence and a first right homology arm DNA sequence, and the second sequence of interest further comprises a second left homology arm DNA sequence and a second right homology arm DNA sequence. In some embodiments, the RB1 and the RB2 are essentially homologous. In some embodiments, the LB1 and the LB2 are essentially homologous. In some embodiments, the RB1 and the RB2 are not essentially homologous. In some embodiments, the LB1 and LB2 are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24. In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO:19. In some embodiments, the sequence of interest comprises one or more expression cassettes. In some embodiments, the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest comprises a sequence encoding a site-specific enzyme target site 5' to an expression cassette and a sequence encoding a site-specific enzyme target site 3' to an expression cassette. In some embodiments, the sequence of interest does not comprise a homology arm DNA sequence. In some embodiments, the sequence of interest comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology DNA arm sequence, and ii) a second sequence that is not positioned between the left homology arm DNA sequence and the right homology arm DNA sequence. In some embodiments, the sequence of interest comprises a sequence positioned between the left homology arm DNA sequence and the right homology DNA arm sequence, where the left and right homology arm sequences are positioned between two sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence that is not positioned between sequences encoding site-specific enzyme target sites. In some embodiments, the sequence of interest comprises i) a first sequence positioned between the left homology arm DNA sequence and the right homology DNA arm sequence where the left and right homology arm sequences are positioned between two sequences encoding site-specific enzyme target sites, and ii) a second sequence encoding the site-specific enzyme, where the second sequence is not positioned between sequences encoding site-specific enzyme target sites. In some embodiments, at least one homology arm DNA sequence comprises a sequence that is at least 80%, at least 85%, at least 90%, at least 95%, or at least 99% identical to a target sequence in the plant genome. In some embodiments, the target sequence in the plant genome is a genic sequence. In some embodiments, the target sequence in the plant genome is a non-genic sequence. In some embodiments, the sequence of interest flanked by homology arms comprises a sequence that is at least 80%, at least 85%, at least 90%, at least 91%, at least 92%, at least 93%, at least 94%, at least 95%, at least 96%, at least 97%, at least 98%, at least 99%, or 100% identical to a native gene of the plant cell. In some embodiments, the sequence of interest comprises a protein-coding sequence. In some embodiments, the sequence of interest comprises a non-protein-coding RNA. In some embodiments, the non-protein-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA), or any combination thereof. In some embodiments, the site-specific enzyme is selected from a group consisting of an endonuclease, a recombinase, and a transposase. In some embodiments, the endonuclease is selected from a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest further comprises at least one site-specific enzyme target site. In some embodiments, the at least one site-specific enzyme target site is selected from a Cre/lox recombination site, a Flp/FRT recombination site, a endonuclease recognition site, and a TALEN site. In some embodiments, the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof. In some embodiments, at least part of the sequence of interest is integrated into the plant genome via homologous recombination, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, at least part of the sequence of interest is integrated into the plant genome via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or a combination thereof. In some embodiments, the plant cell already comprises a site-specific enzyme. In some embodiments, the plant cell is selected from the group consisting of a corn cell, a soybean cell, a canola cell, a cotton cell, a wheat cell, or a sugarcane cell. In some embodiments, a nucleotide sequence encoding the site-specific enzyme is stably transformed into the plant cell.

Several embodiments relate to an *Agrobacterium* cell comprising at least one vector that is capable of forming two essentially complementary T-strands. In some embodiments, the *Agrobacterium* cell comprises at least one vector comprises a first right border DNA sequence (RB1), a second right border DNA sequence (RB2), and at least one sequence of interest, and wherein the RB1 is positioned in the vector to initiate synthesis of a first T-strand such that the sequence of interest is in the sense orientation from the 5' to 3' end of the first T-strand; and the RB2 is positioned in the vector to initiate synthesis of a second T-strand such that the sequence of interest is in the anti-sense orientation relative to the sequence of interest in the first T-strand, and wherein the two T-strands resulting from initiation at RB1 and RB2 are essentially complementary in at least a portion of the sequence of interest. In some embodiments, the *Agrobacterium* cell comprises at least one vector comprises a first right border DNA sequence (RB1), a second right border DNA sequence (RB2), a sequence of interest, a first left border DNA sequence (LB1) and a second left border DNA sequence (LB2), wherein the vector is configured such that the RB1 is paired with the LB1 which are positioned in the vector to initiate (RB1) and terminate (LB1) synthesis of a first T-strand such that the sequence of interest is in the sense orientation from the 5' to 3' end of the first T-strand; and the RB2 is paired with the LB2 which are positioned in the vector to initiate (RB2) and terminate (LB2) synthesis of a second T-strand such that the sequence of interest is in an anti-sense orientation relative to the sequence of interest in the first T-strand, and wherein the two T-strands resulting from initiation at RB1 and RB2 are essentially complementary in at least a portion of the sequence of interest. In some embodiments, the *Agrobacterium* cell comprises at least one vector comprises a first sequence of interest and a second sequence of interest, where the first sequence of interest is essentially identical to the second sequence of interest; wherein the vector further comprises a first right border DNA sequence (RB1) and a first left border DNA sequence (LB1) which are positioned in the vector to initiate (RB1) and terminate (LB1) synthesis of a first T-strand such that the first sequence of interest is in the sense orientation from the 5' to 3' end of the first T-strand; and the vector further comprises a second right border DNA sequence (RB2) and a second left border DNA sequence (LB2) which are positioned in the vector to initiate (RB2) and terminate (LB2) synthesis of a second T-strand such that the second sequence of interest is in an anti-sense orientation relative to the first sequence of interest in the first T-strand, and wherein the two T-strands resulting from initiation at RB1 and RB2 are essentially complementary in at least a portion of the first sequence of interest and the second sequence of interest. In some embodiments, the *Agrobacterium* cell comprises at least a first vector and a second vector wherein each vector comprises essentially identical sequences of interest, and wherein the first vector comprises a first right border DNA sequence (RB1) and a first left border DNA sequence (LB1) which are positioned in the first vector to initiate (RB1) and terminate (LB1) synthesis of a first T-strand such that the sequence of interest is in the sense orientation from the 5' to 3' end of the first T-strand; and wherein the second vector comprises a second right border DNA sequence (RB2) and a second left border DNA sequence (LB2) which are positioned in the second vector to initiate (RB2) and terminate (LB2) synthesis of a second T-strand such that the sequence of interest is in an anti-sense orientation relative to the sequence of interest in the first T-strand, and wherein the two T-strands resulting from initiation at RB1 and RB2 are essentially complementary in at least a portion of the sequence of interest. In some embodiments, the *Agrobacterium* cell comprises a RB1 and RB2 that are essentially homologous. In some embodiments, the *Agrobacterium* cell comprises a LB1 and LB2 that are essentially homologous. In some embodiments, the *Agrobacterium* cell comprises RB1 and RB2 sequences that are not essentially homologous. In some embodiments, the *Agrobacterium* cell of LB1 and LB2 sequences that are not essentially homologous. In some embodiments, at least one of the RB1 and RB2 comprise an *Agrobacterium* Ti plasmid right border consensus DNA sequence. In some embodiments, the right border consensus DNA sequence is selected from SEQ ID NO: 21 or SEQ ID NO: 22. In some embodiments, at least one of the RB1 and RB2 comprise a sequence selected from SEQ ID NOs: 1-13. In some embodiments, at least one of the RB1 and RB2 comprise a sequence at least 80% identical to a sequence selected from SEQ ID NOs:4 and SEQ ID NO:12. In some embodiments, at least one of the LB1 and LB2 comprise an *Agrobacterium* Ti plasmid left border consensus DNA sequence. In some embodiments, the left border consensus DNA sequence is selected from SEQ ID NO: 23 or SEQ ID NO: 24 In some embodiments, at least one of the LB1 and LB2 comprise a sequence selected from SEQ ID NOs: 14-20. In some embodiments, at least one of the LB1 and LB2 comprise a sequence at least 80% identical to SEQ ID NO: 19. In some embodiments, the sequence of interest comprises one or more expression cassettes. In some embodiments, the sequence of interest comprises at least one sequence selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, gene expression cassette comprising a sequence encoding a cell factor that functions to increase DNA repair, a sequence comprising a linker or a spacer, a sequence comprising one or more restriction enzyme sites, a sequence for templated genome editing, and any combination thereof. In some embodiments, the sequence of interest does not comprise a homology arm DNA sequence. In some embodiments, the sequence of interest further comprises at least one homology arm DNA sequence. In some embodiments, the sequence of interest comprises both a left homology arm DNA sequence and a right homology arm DNA sequence. In some embodiments, the sequence of interest comprises i) a first sequence positioned between the left homology arm DNA sequence and the right homology arm DNA sequence, and ii) a second sequence that is not positioned between the region comprising the left homology arm DNA sequence and the right homology arm DNA sequence. In some embodiments, the at least one homology arm DNA sequence comprises a sequence that is at least 80%, at least 85%, at least 90%, at least 95%, or at least 99% identical to a target sequence in the plant genome. In some embodiments, the sequence of interest comprises a protein-coding sequence. In some embodiments, the sequence of interest comprises a non-protein-coding RNA In some embodiments, the non-protein-coding RNA is selected from a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA), or any combination thereof. In some embodiments, the expression cassette comprises a nucleic acid sequence at least 80% identical to a native plant gene. In some embodiments, the expression cassette comprises a nucleic acid sequence that is not homologous to a native plant sequence. In some embodiments, at least one expression cassette comprises at a sequence selected from: an insecticidal resistance gene, herbicide tolerance gene, nitrogen use efficiency gene, a water use efficiency gene, a nutritional quality gene, a DNA binding gene, a selectable marker gene, an RNAi construct, a site specific nuclease gene, a guide RNA, and any combination thereof. In some embodiments, the site-specific enzyme is selected from an endonuclease, a recombinase, a transposase, and any combination thereof. In some embodiments, the endonuclease is selected from the group consisting of: a meganuclease, a zinc finger nuclease, a transcription activator-like effector nuclease (TALEN), an Argonaute, a Cas9 nuclease, a CasX nuclease, a CasY nuclease, and a Cpf1 nuclease. In some embodiments, the Cas9 nuclease is selected from the group comprising Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the recombinase is a tyrosine recombinase attached to a DNA recognition motif, or a serine recombinase attached to a DNA recognition motif. In some embodiments, the tyrosine recombinase attached to a DNA recognition motif is selected from the group consisting of a Cre recombinase, a Flp recombinase, and a Tnp1 recombinase. In some embodiments, the serine recombinase attached to a DNA recognition motif is selected from the group consisting of a PhiC31 integrase, an R4 integrase, and a TP-901 integrase. In some embodiments, the transposase is a DNA transposase attached to a DNA binding domain. In some embodiments, the sequence of interest comprises at least one site-specific enzyme target site. In some embodiments, at least one site-specific enzyme target site is selected from the group consisting of: a Cre/lox recombination site, a Flp/FRT recombination site, a endonuclease recognition site, and a TALEN site. In some embodiments, the sequence of interest comprises a sequence encoding at least one protein involved in DNA repair, wherein the protein is selected from the group comprising a vir gene from the Ti plasmid, Rad51, Rad52, Rad2, a dominant-negative Ku70, or any combination thereof.

Several embodiments relate to an *Agrobacterium* cell comprising at least one vector comprising a right border DNA sequence (RB) and a left border DNA sequence (LB) and wherein the vector comprises between the RB and LB: (i) a first sequence of interest in a sense orientation relative to the RB, (ii) a spacer, and (iii) a second sequence of interest in an anti-sense orientation relative to the RB, wherein the first sequence of interest and second sequence of interest are essentially complementary, and after synthesis of the T-strand anneal to form a double-stranded DNA. Ins some embodiments, the *Agrobacterium* cell comprises a first sequence of interest comprising a left homology arm DNA sequence and a right homology arm DNA sequence and a second sequence of interest comprising a left homology arm sequence DNA sequence and a right homology arm DNA sequence. In some embodiments, the RB comprises an *Agrobacterium* Ti plasmid right border consensus DNA sequence. In some embodiments, the right border consensus DNA sequence is selected from SEQ ID NO: 21 or SEQ ID NO: 22. In some embodiments, the RB comprises a sequence selected from SEQ ID NOs: 1-13. In some embodiments, the RB comprises a sequence at least 80% identical to a sequence selected from SEQ ID NOs:4 and SEQ ID NO:12. In some embodiments, the LB comprises an *Agrobacterium* Ti plasmid left border consensus DNA sequence. In some embodiments, the left border consensus DNA sequence is selected from SEQ ID NO: 23 or SEQ ID NO: 24. In some embodiments, the LB comprises a sequence selected from SEQ ID NOs: 14-20. In some embodiments, the LB comprises a sequence at least 80% identical to SEQ ID NO: 19. In some embodiments, a sequence of interest comprises one or more expression cassettes. In some embodiments, a sequence of interest comprises at least one sequence selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, gene expression cassette comprising a sequence encoding a cell factor that functions to increase DNA repair, a sequence comprising a linker or a spacer, a sequence comprising one or more restriction enzyme sites, a sequence for templated genome editing, and any combination thereof. In some embodiments, a sequence of interest does not comprise a homology arm DNA sequence. In some embodiments, a sequence of interest further comprises at least one homology arm DNA sequence.

Several embodiments relate to a method of transforming a plant genome, comprising contacting at least one plant cell on a co-culture medium for at least 24-48 hours, for at least 24-30 hours, for at least 30-36 hours, for at least 36-42 hours, for at least 42-48 hours, for at least 48-54 hours, for at least 54-60 hours, for at least 60-66 hours, for at least 66-72 hours, for at least 72-78 hours, for at least 78-84 hours, for at least 84-90 hours, for at least 90-96 hours, for at least 96-102 hours, for at least 102-108 hours, for at least 108-114 hours, for at least 114-120 hours, for at least 120-126 hours, or for at least 126-132 hours, with at least one Rhizobiales cell capable of transforming the plant cell, In some embodiments, the Rhizobiales cell comprises at least one vector capable of forming two essentially complementary T-strands. In some embodiments, the plant cell is a corn immature embryo cell, a corn mature embryo cell, a corn seed cell, a soybean immature embryo cell, a soybean mature embryo cell, a soybean seed cell, a canola immature embryo cell, a canola mature embryo cell, a canola seed cell, a cotton immature embryo cell, a cotton mature embryo cell, a cotton seed cell, a wheat immature embryo cell, a wheat mature embryo cell, a wheat seed cell, a sugarcane immature embryo cell, a sugarcane mature embryo cell, or a sugarcane seed cell. In some embodiments, the Rhizobiales cell comprises at least one vector comprises a first right border (RB1) DNA sequence, a second right border DNA sequence (RB2), and at least one sequence of interest, and wherein the RB1 is positioned in the vector to initiate synthesis of a first T-strand such that the sequence of interest is in the sense orientation from the 5' to 3' end of the first T-strand; and the RB2 is positioned in the vector to initiate synthesis of a second T-strand such that the sequence of interest is in the anti-sense orientation relative to the sequence of interest in the first T-strand, and wherein the sequence of interest in the two T-strands resulting from initiation at RB1 and RB2 are essentially complementary in at least a portion of the sequence of interest. In some embodiments, the Rhizobiales cell comprises at least one vector disclosed herein comprises a RB1, a RB2, and a sequence of interest, and further comprises a first left border DNA sequence (LB1) and a second left border DNA sequence (LB2), and wherein the vector is configured such that the RB1 is paired with the LB1 which are positioned in the vector to initiate (RB1) and terminate (LB1) synthesis of a first T-strand such that the sequence of interest is in the sense orientation from the 5' to 3' end of the first T-strand; and the RB2 is paired with the LB2 which are positioned in the vector to initiate (RB2) and terminate (LB2) synthesis of a second T-strand such that the sequence of interest is in an anti-sense orientation relative to the sequence of interest in the first T-strand, and wherein the sequence of interest in the two T-strands resulting from initiation at RB1 and RB2 are essentially complementary in at least a portion of the sequence of interest. In some embodiments, the Rhizobiales cell comprises a vector comprising a first sequence of interest and a second sequence of interest, where the first sequence of interest is essentially identical to the second sequence of interest; and the vector configuration further comprises a RB1 with aLB1 which are positioned in the vector to initiate (RB1) and terminate (LB1) synthesis of a first T-strand such that the first sequence of interest is in the sense orientation from the 5' to 3' end of the first T-strand; and the vector further comprises a RB2 and a LB2 which are positioned in the vector to initiate (RB2) and terminate (LB2) synthesis of a second T-strand such that the second sequence of interest is in an anti-sense orientation relative to the first sequence of interest in the first T-strand, and wherein the sequence of interest in the two T-strands resulting from initiation at RB1 and RB2 are essentially complementary in at least a portion of the first sequence of interest and the second sequence of interest. In some embodiments, the Rhizobiales cell comprises at least a first vector and a second vector, wherein each vector comprises essentially identical sequences of interest, and wherein the first vector configuration comprises a RB1 and a LB1 which are positioned in the first vector to initiate (RB1) and terminate (LB1) synthesis of a first T-strand such that the sequence of interest is in the sense orientation from the 5' to 3' end of the first T-strand; and wherein the second vector configuration comprises a RB2 and a LB2 which are positioned in the second vector to initiate (RB2) and terminate (LB2) synthesis of a second T-strand such that the sequence of interest is in an anti-sense orientation relative to the sequence of interest in the first T-strand, and wherein the sequence of interest in the two T-strands resulting from initiation at RB1 and RB2 are essentially complementary in at least a portion of the sequence of interest. In some embodiments, the Rhizobiales cell comprises at least one vector comprises a first sequence of interest, a second sequence of interest different from the first sequence of interest, at least two RB DNA sequences, and one or more optional LB DNA sequences, wherein the first RB DNA sequence (RB1) and a first LB DNA sequence (LB1) are positioned in the vector to initiate (RB1) and terminate (LB1) synthesis of the first T-strand such that the first sequence of interest is in the sense orientation from the 5' to 3' end of the first T-strand; and the vector configuration further comprises a second RB DNA sequence (RB2) and a second LB DNA sequence (LB2) which are positioned in the vector to initiate (RB2) and terminate (LB2) synthesis of a second T-strand such that the first sequence of interest is in an anti-sense orientation from the 5' to 3' end of the second T-strand, wherein the two T-strands resulting from initiation at RB1 and RB2 are essentially complementary to each other in at least a portion of the first sequence of interest, and wherein the vector configuration further comprises a third RB DNA sequence (RB3) and a third LB DNA sequence (LB3) which are positioned in the vector to initiate (RB3) and terminate (LB3) synthesis of a third T-strand such that the second sequence of interest is in the sense orientation from the 5' to 3' end of the third T-strand; and the vector configuration further comprises a fourth RB DNA sequence (RB4) and a fourth LB DNA sequence (LB4) which are positioned in the vector to initiate (RB4) and terminate (LB4) synthesis of a fourth T-strand such that the second sequence of interest is in an anti-sense orientation from the 5' to 3' end of the fourth T-strand, and the two T-strands resulting from initiation at RB3 and RB4 are essentially complementary to each other in at least a portion of the second sequence of interest. In some embodiments, the method comprises contacting the plant cell with a first Rhizobiales cell and a second Rhizobiales cell, wherein each Rhizobiales cell contains at least one of two vectors, wherein each vector comprises an essentially identical sequence of interest, and where the first vector comprises a RB1, and wherein the RB1 is positioned in the vector to initiate synthesis of a first T-strand such that the sequence of interest is in the sense orientation from the 5' to 3' end of the first T-strand; and the second vector comprises a RB2 which is positioned in the vector to initiate synthesis of a second T-strand such that the sequence of interest is in the anti-sense orientation relative to the sequence of interest in the first T-strand, and wherein the two T-strands resulting from initiation at RB1 and RB2 are essentially complementary in at least a portion of the sequence of interest. In some embodiments, the method comprises contacting the plant cell with a first Rhizobiales cell and a second Rhizobiales cell, wherein each Rhizobiales cell contains at least one of two vectors, wherein each vector comprises an essentially identical sequence of interest, and where the first vector comprises a RB1 and a LB1 which are positioned in the first vector to initiate (RB1) and terminate (LB1) synthesis of a first T-strand such that the sequence of interest is in the sense orientation from the 5' to 3' end of the first T-strand; and the second vector comprises a RB2 and a LB2 which are positioned in the second vector to initiate (RB2) and terminate (LB2) synthesis of a second T-strand such that the sequence of interest is in an anti-sense orientation from the 5' to 3' end of the second T-strand, and wherein the sequence of interest in the two T-strands resulting from initiation at RB1 and RB2 are essentially complementary to each other. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the *Agrobacterium* spp. cell is selected from the group consisting of an *Agrobacterium tumefaciens* cell and an *Agrobacterium rhizogenes* cell. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof. In some embodiments the method results in at least a fragment of the sequence of interest being integrated into the plant genome by homologous recombination. In some embodiments, the method results in at least a fragment of the sequence of interest being integrated into the plant genome by non-homologous end joining. In some embodiments, the method further comprises detecting the integration of at least a fragment of the sequence of interest of the vector in the at least one plant cell. In some embodiments, the method further comprises selecting the plant cell based on the presence of the at least a fragment of the sequence of interest integrated into the plant genome. In some embodiments, the method further comprises regenerating a transgenic plant from the selected plant cell.

Several embodiments relate to a method of transforming a plant genome, comprising contacting at least one plant cell on a co-culture medium for at least 24-48 hours, for at least 24-30 hours, for at least 30-36 hours, for at least 36-42 hours, for at least 42-48 hours, for at least 48-54 hours, for at least 54-60 hours, for at least 60-66 hours, for at least 66-72 hours, for at least 72-78 hours, for at least 78-84 hours, for at least 84-90 hours, for at least 90-96 hours, for at least 96-102 hours, for at least 102-108 hours, for at least 108-114 hours, for at least 114-120 hours, for at least 120-126 hours, or for at least 126-132 hours, with at least one Rhizobiales cell capable of transforming the plant cell, wherein the Rhizobiales cell comprises at least one vector comprising a right border (RB) DNA sequence and a left border (LB) DNA sequence and where the vector further comprises between the RB and LB DNA sequences: (i) a first sequence of interest in a sense orientation relative to the RB DNA sequence, and (ii) a spacer, and (iii) a second sequence of interest in an anti-sense orientation relative to the RB DNA sequence, wherein the first sequence of interest and second sequence of interest are essentially complementary, and after synthesis of the T-strand anneal to form a double-stranded DNA. In some embodiments, the first sequence of interest further comprises a left homology arm DNA sequence and a right homology arm DNA sequence in and the second sequence of interest further comprises a left homology arm DNA sequence and a right homology arm DNA sequence. In some embodiments, the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In some embodiments, the *Agrobacterium* spp. cell is selected from the group consisting of an *Agrobacterium tumefaciens* cell and an *Agrobacterium rhizogenes* cell. In some embodiments, the Rhizobiales cell further contains a vector comprising at least one expression cassette, wherein the expression cassettes comprise a sequence encoding a protein involved in DNA repair, and wherein the protein is selected from the group comprising a vir gene from the Ti plasmid, Rad51, Rad52, Rad2, a dominant-negative Ku70, or any combination thereof. In some embodiments the method results in at least a fragment of the sequence of interest being integrated into the plant genome by homologous recombination. In some embodiments, the method results in at least a fragment of the sequence of interest being integrated into the plant genome by non-homologous end joining. In some embodiments, the method further comprises detecting the integration of at least a fragment of the sequence of interest of the vector in the at least one plant cell. In some embodiments, the method further comprises selecting the plant cell based on the presence of the at least a fragment of the sequence of interest integrated into the plant genome. In some embodiments, the method further comprises regenerating a transgenic plant from the selected plant cell.

BRIEF DESCRIPTION OF FIGURES

The accompanying drawings, which are incorporated in and form a part of the specification, illustrate the aspects of this disclosure and together with the description, serve to explain embodiments described in the disclosure. In the drawings:

FIG. 3B illustrates a first cassette positioned between two homology arms (HA) and a second cassette positioned outside of the one of the homology arms (HA). FIG. 3C illustrates both a first cassette and a second cassette positioned between two homology arms (HA).

FIG. 5 further illustrates the position of PCR primers and Southern blot probes used in Example 9.

DETAILED DESCRIPTION

Figure 1:
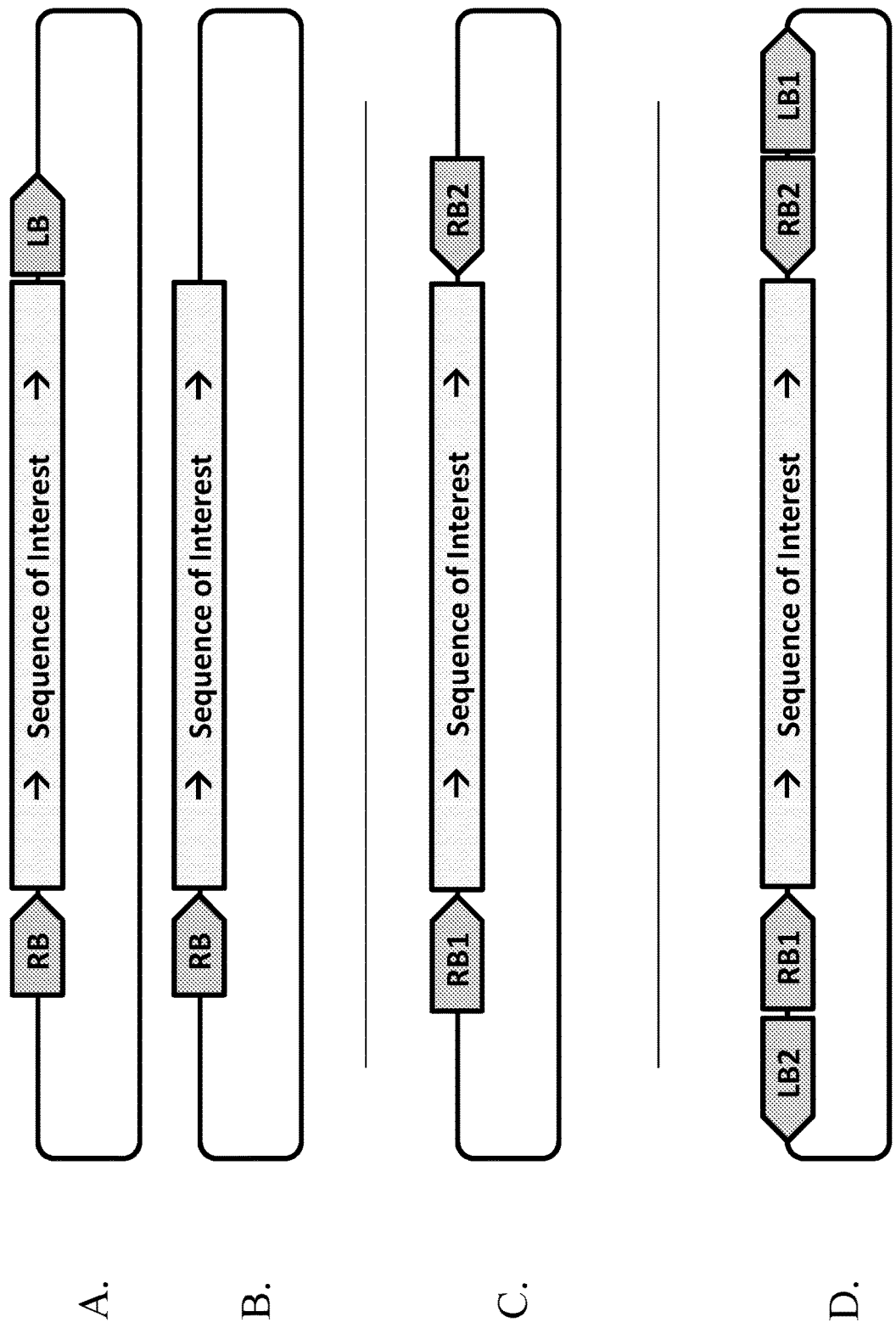
FIGS. 1A and 1B illustrate two control vector configurations in which a sequence of interest is flanked by a right border (RB) DNA sequence on the 5' end, and a left border (LB) DNA sequence on the 3' end (Panel 1A); or alternatively, one RB DNA sequence on the 5' end (Panel 1B).
FIG. 1C illustrates a vector configuration comprising two RB DNA sequences, where the first RB DNA sequence (RB1) is positioned in the vector to initiate synthesis of a first T-strand such that the sequence of interest is in the sense orientation from the 5' to 3' end of the first T-strand; and the second RB DNA sequence (RB2) is positioned in the vector to initiate synthesis of a second T-strand such that the sequence of interest is in the anti-sense orientation from the 5' to 3' end of the second T-strand. The two T-strands resulting from initiation at RB1 and RB2 are essentially complementary to each other in at least a portion of the sequence of interest.
FIG. 1D illustrates a vector configuration comprising optional LB DNA sequences. In the illustrated vector configuration, the first RB DNA sequence (RB1) is paired with a first LB DNA sequence (LB1) which are positioned in the vector to initiate (RB1) and terminate (LB1) synthesis of a first T-strand such that the sequence of interest is in the sense orientation from the 5' to 3' end of the first T-strand; and the second RB DNA sequence (RB2) is paired with a second left border DNA sequence (LB2) which are positioned in the vector to initiate synthesis of a second T-strand such that the sequence of interest is in an anti-sense orientation from the 5' to 3' end of the second T-strand. The two T-strands resulting from initiation at RB1 and RB2 are essentially complementary to each other in at least a portion of the sequence of interest.

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of this disclosure includes, unless otherwise indicated, conventional techniques of biochemistry, chemistry, molecular biology, microbiology, cell biology, genomics and biotechnology, which are within the skill of the art. See Green and Sambrook, Molecular Cloning: A Laboratory Manual, 4th edition (2012); Current Protocols In Molecular Biology (F. M. Ausubel, et al. eds., (1987)); the series Methods In Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Animal Cell Culture (R. I. Freshney, ed. (1987)); Recombinant Protein Purification: Principles And Methods, 18-1142-75, GE Healthcare Life Sciences; C. N. Stewart, A. Touraev, V. Citovsky, T. Tzfira eds. (2011) Plant Transformation Technologies (Wiley-Blackwell); and R. H. Smith (2013) Plant Tissue Culture: Techniques and Experiments (Academic Press, Inc.).

All references cited herein are incorporated by reference in their entireties.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, "plant" refers to a whole plant. A cell or tissue culture derived from a plant can comprise any plant components or plant organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

As used herein, "transgenic" means a plant cell, a plant, a plant part, or a seed whose genome has been altered by the stable integration of exogenous DNA. A transgenic line includes a plant regenerated from an originally-transformed plant cell and progeny transgenic plants from later generations or crosses of a transformed plant.

As used herein, "stably transformed" is defined as a transfer of DNA into genomic DNA of a targeted cell that allows the targeted cell to pass the transferred DNA to the next generation. In some embodiments the transferred DNA is integrated into the genomic DNA of a reproductive cell. In embodiments the transferred DNA is integrated into the genomic DNA of a somatic cell. As used herein, "transiently transformed" is defined as a transfer of DNA into a cell that is not integrated into the transformed cell's genomic DNA.

As used herein, "plant genome" refers to a nuclear genome, a mitochondrial genome, or a plastid (e.g., chloroplast) genome of a plant cell.

In one aspect, the instant disclosure provides a Rhizobiales cell comprising at least one vector that is capable of forming at least two T-strands that are essentially complementary in at least a portion of a sequence of interest. In another aspect, the instant disclosure provides a Rhizobiales cell comprising at least one vector that is capable of forming at least two T-strands that are essentially complementary for at least a portion of the vector backbone. In another aspect, the instant disclosure provides a Rhizobiales cell comprising at least one vector that is capable of forming two T-strands that are essentially complementary for at least 25, 30, 35, 40, 45, 50, 60, 70, 80, 90, 100, 200, 300, 400, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000, or more base pairs. In some aspects, 1, 2, 3, 4, 5, 6, 7, 8, 9 or 10 or more vectors provided herein are located within a single Rhizobiales cell.

In another aspect, the instant disclosure provides a Rhizobiales cell comprising at least a first vector and a second vector, where the first vector is configured to produce a first T-strand comprising a sequence of interest and the second vector is configured to produce a second T-strand comprising a sequence of interest oriented such that the first and second T-strands are essentially complementary in at least a portion of a sequence of interest. In another aspect, the instant disclosure provides a Rhizobiales cell comprising at least a first vector and a second vector that are capable of producing a first T-strand and a second T-strand that are essentially complementary for at least a portion of the vector backbone. In another aspect, the instant disclosure provides a Rhizobiales cell comprising at least a first vector and a second vector that are capable of producing a first T-strand and a second T-strand that are essentially complementary for at least 25, 30, 35, 40, 45, 50, 60, 70, 80, 90, 100, 200, 300, 400, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000, or more base pairs. In some aspects, 3, 4, 5, 6, 7, 8, 9 or 10 or more vectors provided herein are located within a single Rhizobiales cell.

As used herein, the term "Rhizobiales" refers to members of the bacterial Order Rhizobiales that are capable of transforming a plant cell. In some aspects, a Rhizobiales provided herein can refer to an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp. In other aspects, a Rhizobiales provided herein can refer to *Agrobacterium tumefaciens* or *Agrobacterium rhizogenes*. In some aspects, 1, 2, 3, 4, 5, 6, 7, 8, 9 or 10 or more vectors provided herein are located within a single Rhizobiales cell. In other aspects, 2, 3, 4, 5, 6, 7, 8, 9 or 10 or more different vectors provided herein are located within 2, 3, 4, 5, 6, 7, 8, 9 or 10 or more different Rhizobiales cells.

As used herein, the term "recombination" refers to the exchange of nucleotides between two nucleic acid molecules. The term "homologous recombination" (HR) refers to the exchange of nucleotides at a conserved region shared by two nucleic acid molecules. HR includes symmetric homologous recombination and asymmetric homologous recombination. Asymmetric homologous recombination can also mean unequal recombination. As used herein, "non-homologous end joining" (NHEJ) refers to the ligation of two ends of double-stranded DNA without the need of a homologous sequence to direct the ligation. As used herein, "microhomology" refers to the presence of the same short sequence (1 to 10 bp) of bases in different nucleic acid molecules. In some embodiments, at least one of the nucleic acid molecules is genomic DNA and at least one of the nucleic acid molecules comprises two T-strands that are essentially complementary in at least a portion of a sequence of interest.

Methods for detecting HR and NHEJ include, but are not limited to, 1) phenotypic screening, 2) molecular marker technologies such as single nucleotide polymorphism (SNP) analysis by TaqMan® or Illumina/Infinium technology, 3) Southern blot, and 4) sequencing (e.g., Sanger, Illumina®, 454, Pac-Bio, Ion Torrent™). One example of a method for identifying recombination between two parental chromosomes is inverse PCR (iPCR). In this method, restriction nuclease sites flanking a targeted gene are identified on each of the two parental chromosomes. These restriction nuclease sites can be the same or different. A PCR primer specific for the first parental chromosome and another PCR primer specific for the second parental chromosome are designed. An induced double-strand break promotes recombination between the two parental chromosomes brings both restriction endonuclease sites and primer binding sites onto the same recombinant chromosome. A PCR product is observed only in instances where recombination occurs. In one aspect, the occurrence of homologous recombination can be detected by PCR, with primers specifically designed for the T-strand insert paired with primers specifically designed for flanking sequences of the target sequence (outside of the homologous regions). For example, when an upstream flanking primer is paired with a downstream insert-specific primer, a PCR product is observed only when recombination occurs.

As used herein, the term "vector" or "plasmid" is used interchangeably and refer to a circular, double-stranded DNA molecule that is physically separate from chromosomal DNA. In one aspect, a plasmid or vector used herein is capable of replication in vivo. In several embodiments, the vector is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid.

In one aspect, a plasmid or vector provided herein is a recombinant vector. As used herein, the term "recombinant vector" refers to a vector formed by laboratory methods of genetic recombination, such as molecular cloning. In another aspect, a vector or plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

As used herein, the terms "homology" and "identity" when used in relation to nucleic acids, describe the degree of similarity between two or more nucleotide sequences. The percentage of "sequence identity" between two sequences is determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. (1994) Nucl. Acids Res., 22: 4673-4680).

As used herein, the term "complementary" in reference to a nucleic acid molecule refers to pairing of nucleotide bases such that A is complementary to T (or U), and G is complementary to C. Two complementary nucleic acid molecules are capable of hybridizing with each other. As an example, the two strands of double stranded DNA are complementary to each other.

As used herein, the term "essentially homologous" or "essentially identical" means that two nucleotide sequences have at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity with each other.

As used herein, the term "essentially complementary" means that two nucleotide sequences have at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence complementarity with each other.

As used herein, a "portion" of a nucleic acid molecule refers to at least 5%, 10%, 20%, 30%, 40%, 50%, 60%, 70%, 80%, 90%, 95%, 96%, 97%, 98%, 99%, or 100% of its total length, or at least 5, 10, 15, 20, 25, 30, 25, 40, 45, 50, 75, 100, 150, 200, 250, 300, 350, 400, 450, 500, 600, 700, 800, 900, or 1000 or more contiguous nucleotides.

As used herein, the term "polynucleotide" refers to a nucleic acid molecule containing multiple nucleotides and generally comprises at least 2, at least 5, at least 10, at least 20, at least 30, at least 40, at least 50, at least 100, at least 250, at least 500, at least 1000, at least 1500, at least 2000, at least 2500, at least 3000, at least 5000, at least 10,000 or more nucleotide bases. As an example, a polynucleotide provided herein can be a plasmid. A specific polynucleotide of 18-25 nucleotides in length may be referred to as an "oligonucleotide". Nucleic acid molecules provided herein include deoxyribonucleic acids (DNA) and ribonucleic acids (RNA) and functional analogues thereof, such as complementary DNA (cDNA). Nucleic acid molecules provided herein can be single stranded or double stranded. Nucleic acid molecules comprise the nucleotide bases adenine (A), guanine (G), thymine (T), cytosine (C). Uracil (U) replaces thymine in RNA molecules. The symbol "N" can be used to represent any nucleotide base (e.g., A, G, C, T, or U). The symbol "K" can be used to represent a G or a T/U nucleotide base.

As used herein, "physically linked" means that the physically linked nucleic acid sequences are located on the same nucleic acid molecule. A physical linkage can be adjacent or proximal. In an aspect, a nucleic acid sequence provided herein is adjacent to another nucleic acid sequence. In another aspect, a first nucleic acid molecule provided herein is physically linked to a second nucleic acid molecule provided herein. As used herein, "flanked" refers to a nucleic acid sequence that is linked on one or both sides to another nucleic acid sequence, including linked to a sequence of interest, or to a LB DNA sequence, or a RB DNA sequence. In one aspect, a flanking sequence precedes a sequence of interest. In another aspect, a flanking sequence follows a sequence of interest. In one aspect, a sequence of interest is flanked by another sequence of interest. In yet another aspect, a flanking sequence is on the 5' or upstream end of a sequence of interest. In another aspect, a flanking sequence is on the 3' or downstream end of a sequence of interest. In some embodiments, the flanking sequence is contiguous with the sequence of interest. In some embodiments, there are one or more nucleotides between the flanking sequence and the sequence of interest.

As used herein, "operably linked" means that the operably linked nucleic acid sequences exhibit their desired function. For example, in an aspect of this disclosure, a provided DNA promoter sequence can initiate transcription of an operably linked DNA sequence into RNA. A nucleic acid sequence provided herein can be upstream or downstream of a physically or operably linked nucleic acid sequence. In an aspect, a first nucleic acid molecule provided herein is both physically linked and operably linked to a second nucleic acid molecule provided herein. In another aspect, a first nucleic acid molecule provided herein is neither physically linked nor operably linked to a second nucleic acid molecule provided herein. As used herein, "upstream" means the nucleic acid sequence is positioned before the 5' end of a linked nucleic acid sequence. As used herein, "downstream" means the nucleic acid sequence is positioned after the 3' end of a linked nucleic acid sequence.

As used herein, a "spacer" or a "linker" refers to any polynucleotide sequence capable of forming a loop structure that is at least 4 nucleotides in length. Without being limiting, a spacer provided herein can comprise a non-coding sequence or a coding sequence.

Right and Left Borders

As used herein, the term "T-strand" refers to a single-strand copy of DNA made when transcription is initiated from a RB DNA sequence of a vector. In a naturally occurring Ti plasmid, synthesis of the transfer DNA (T-DNA) is initiated at a 25-base-pair consensus DNA sequence referred to as the "right border" (RB), and T-strand synthesis termination occurs at a 25 bp consensus DNA sequence referred to as the "left border" (LB). The 25 bp RB consensus DNA sequence (SEQ ID NO: 21) and the 25 bp LB consensus DNA sequence (SEQ ID NO: 23) are from the nopaline *Agrobacterium tumefaciens* strain C58. The 25 bp RB consensus DNA sequence (SEQ ID NO: 22) and the 25 bp LB consensus DNA sequence (SEQ ID NO: 24) are from the octopine *Agrobacterium tumefaciens* strain A6. In some embodiments, a RB consensus DNA sequence is selected from SEQ ID NOs: 21 and 23. In some embodiments a LB consensus DNA sequence is selected from SEQ ID NOs: 22 and 24.

In one aspect, a RB DNA sequence or LB DNA sequence provided herein comprises at least a 25 bp Ti plasmid RB or LB (respectively) consensus DNA sequence and may additionally comprise a nucleic acid sequence comprising at least 25 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, at least 500 nucleotides, or at least 600 nucleotides. In an aspect, a RB DNA sequence or a LB DNA sequence provided herein can be of any length such that the DNA segment is capable of transformation of plant tissue performed by *Agrobacterium* or other Rhizobiales-mediated methods (See U.S. Pat. Nos. 5,731,179 and 6,265,638; and U.S. Patent Application Publications US2003/110532; US2005/0183170; and US2007/0271627).

As used in this application, RB DNA sequences are presented as SEQ ID NOs: 1-13 and are variants of *A. tumefaciens* Ti plasmid sequences ranging from 162 nt to 505 nt in length and comprising either the nopaline RB consensus DNA sequence (SEQ ID NO: 21) or the octopine RB consensus DNA sequence (SEQ ID NO: 22). Similarly, as used in this application, LB DNA sequences are presented as SEQ ID NOs: 14-20 and are variants of *A. tumefaciens* Ti plasmid sequences ranging from 220 nt to 443 nt in length and comprising either the nopaline LB consensus DNA sequence (SEQ ID NO: 23) or the octopine LB consensus DNA sequence (SEQ ID NO: 24). Table 1 contains the SEQ ID NOs for each of the RB and LB DNA sequences presented herein with the position indicated within each SEQ ID NO of the nopaline or octopine 25 bp consensus sequences. Other RB and LB sequences are contemplated.

TABLE 1

SEQ ID NOs of disclosed right border (RB) and left border (LB) DNA sequences

| SEQ ID NO | Length (# of nt) | RB or LB DNA Sequence | Nopaline or Octopine | Position of 25 bp consensus |
|---|---|---|---|---|
| 1 | 355 | RB | Nopaline | 291-315 |
| 2 | 356 | RB | Nopaline | 292-316 |
| 3 | 355 | RB | Nopaline | 291-315 |
| 4 | 505 | RB | Octopine | 194-218 |
| 5 | 470 | RB | Nopaline | 293-317 |
| 6 | 334 | RB | Octopine | 194-218 |
| 7 | 162 | RB | Nopaline | 98-122 |
| 8 | 329 | RB | Nopaline | 291-315 |
| 9 | 331 | RB | Nopaline | 293-317 |
| 10 | 331 | RB | Nopaline | 293-317 |
| 11 | 285 | RB | Octopine | 194-218 |
| 12 | 357 | RB | Nopaline | 293-317 |
| 13 | 330 | RB | Nopaline | 292-316 |
| 14 | 220 | LB | Nopaline | 46-70 |
| 15 | 401 | LB | Octopine | 222-246 |
| 16 | 443 | LB | Octopine | 263-287 |
| 17 | 319 | LB | Nopaline | 58-82 |
| 18 | 427 | LB | Nopaline | 166-190 |
| 19 | 442 | LB | Octopine | 263-287 |
| 20 | 411 | LB | Octopine | 232-256 |

In one aspect, a vector provided herein can comprise at least 1, at least 2, at least 3, at least 4, at least 5, at least 6, at least 7, at least 8, at least 9, or at least 10 RB DNA sequences. In one aspect of the vector, the RB DNA sequence comprises an octopine *Agrobacterium* Ti plasmid 25 bp RB DNA consensus sequence. In another aspect of the vector, the RB DNA sequence comprises a nopaline *Agrobacterium* Ti plasmid 25 bp RB consensus DNA sequence. In another aspect, in vector configurations with two or more RB DNA sequences, the RB DNA sequences may be essentially homologous or the RB DNA sequences may not be essentially homologous. In another aspect, the one or more RB DNA sequences comprise a sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical to a sequence selected from SEQ ID NOs: 1-13. In another embodiment, the first RB (RB 1) DNA sequence or the second RB (RB2) DNA sequence comprises a sequence selected from the group comprising SEQ ID NOs: 1-13. In some embodiments, the RB1 DNA sequence comprises a sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical to a sequence selected from SEQ ID NO: 4 or SEQ ID NO: 12; and the RB2 DNA sequence comprises a sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical to a sequence selected from SEQ ID NO: 4 or SEQ ID NO: 12.

In one aspect, the at least one vector disclosed herein does not comprise a LB DNA sequence. In another aspect, the at least one vector disclosed herein comprises at least one, at least 1, at least 2, at least 3, at least 4, at least 5, at least 6, at least 7, at least 8, at least 9, or at least 10 LB DNA sequences. In another aspect, in vector configurations with two or more LB DNA sequences, the LB DNA sequences may be essentially homologous or the LB DNA sequences may not be essentially homologous. In a further aspect, the LB DNA sequence comprises an octopine *Agrobacterium* Ti plasmid 25 bp LB consensus DNA sequence. In another aspect, the LB DNA sequence comprises a nopaline *Agrobacterium* Ti plasmid 25 bp LB consensus DNA sequence. In one aspect, the one or more of the LB DNA sequences are selected from the group comprising SEQ ID NOs: 14-20. In another aspect, the two or more LB DNA sequences comprise a sequence at least 80%, at least 81%, at least 81%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a sequence selected from SEQ ID NOs: 14-20. In one aspect, the LB DNA sequence comprises a sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical to SEQ ID NO: 19.

Sequence of Interest

As used herein, the term "sequence of interest" refers to a polynucleotide sequence in a vector that forms part of the T-strand. In one aspect, a vector provided herein comprises 0, at least 1, at least 2, at least 3, at least 4, at least 5, at least 6, at least 7, at least 8, at least 9, or at least 10, or more sequences of interest. As used herein, a sequence of interest in a vector disclosed herein does not include RB or a LB DNA sequences, and does not include vector backbone sequence. In one aspect, in vector configurations with two sequences of interest positioned between two RB DNA sequences such that the sequence of interest in the two T-strands synthesized from the two RB DNA sequences are essentially complementary. In some embodiments, the nucleotide sequence of the two sequences of interest may be identical, or the nucleotide sequence may be at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical.

In some aspects, a sequence of interest provided herein comprises 0, at least 1, at least 2, at least 3, at least 4, at least 5, at least 6, at least 7, at least 8, at least 9, or at least 10 expression cassettes. In some aspects, the sequence of interest provided herein comprises one or more expression cassettes physically and/or operably linked in a cassette stack. In some aspects a sequence of interest comprises an expression cassette adjacent to a left homology arm DNA sequence, a right homology arm DNA sequence, or a left homology arm DNA sequence and a right homology arm DNA sequence. In some aspects, a sequence of interest comprises an expression cassette flanked by homology arm DNA sequences. In some aspects, a sequence of interest comprises one ore more expression cassettes that is not flanked by homology arms. In some aspects, a sequence of interest comprises one or more expression cassettes flanked by one ore more site-specific enzyme target sites. In some aspects, a sequence of interest comprises one or more expression cassettes flanked by one ore more recombinase recognition sites. In another aspect, a sequence of interest provided herein comprises an endogenous polynucleotide sequence. In some embodiments, the endogenous polynucleotide sequence comprises an intergenic sequence, a native gene, or a mutated gene. In another aspect, a sequence of interest provided herein comprises an exogenous polynucleotide sequence.

In one aspect, at least part of the sequence of interest in the vector disclosed herein is integrated into a plant genome via HR. In another aspect, at least part of the sequence of interest in the vector disclosed herein is integrated into a plant genome via NHEJ.

In one aspect, a sequence of interest is flanked by at least two homology arm DNA sequences and comprises a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a native gene of a plant cell. In some embodiments, the at least two homology are sequences are flanked by one or more site-specific enzyme target sites. In some embodiments, the at least two homology are sequences are flanked by one or more recombinase recognition sites.

Homology Arms

In an aspect, a sequence of interest provided herein comprises 0, at least 1, or at least 2 homology arm DNA sequences. When a sequence of interest provided herein comprises at least two homology arm DNA sequences the at least two homology arm DNA sequences can be distinguished by referring to them as a "left homology arm DNA sequence" and a "right homology arm DNA sequence." In an aspect, a sequence of interest provided herein comprises both a left homology arm DNA sequence and a right homology arm DNA sequence. In an aspect, a right homology arm DNA sequence and a left homology arm DNA sequence provided herein are homologous to a targeted genomic DNA sequence in the plant or plant cell. In an aspect, a right homology arm DNA sequence and a left homology arm DNA sequence are not essentially homologous to each other. In another aspect, a right homology arm DNA sequence and a left homology arm DNA sequence are essentially homologous to each other. In an aspect, a sequence of interest comprises one or more expression cassettes positioned between a right homology arm DNA sequence and a left homology arm DNA sequence. In an aspect, a sequence of interest comprises a sequence for templated genome editing positioned between a right homology arm DNA sequence and a left homology arm DNA sequence. In yet another aspect, at least part of a sequence of interest provided herein is outside of the region comprising a left homology arm DNA sequence, a right homology arm DNA sequence, and one or more cassettes. In another aspect, at least part of a sequence of interest provided herein is within the region comprising a left homology arm DNA sequence, a right homology arm DNA sequence, and a sequence for templated genome editing.

In one aspect, a sequence of interest provided herein comprises a first sequence positioned between a left homology arm DNA sequence and a right homology arm DNA sequence, and a second sequences that is not positioned between a left homology arm DNA sequence and a right homology arm DNA sequence. In another aspect, a vector provided herein comprises a first sequence of interest further comprising a first left homology arm DNA sequence and a first right homology arm DNA sequence and a second sequence of interest further comprising a second left homology arm DNA sequence and a second right homology arm DNA sequence.

In an aspect, a sequence of interest provided herein is integrated into a plant genome in its entirety. In an aspect, at least a part of a sequence of interest provided herein is integrated into a plant genome. In another aspect, only the sequence of interest between a right homology arm DNA sequence and a left homology arm DNA sequence is integrated into a plant genome. In another aspect, a sequence of interest provided herein is integrated into a plant genome via HR. In an aspect, HR can occur between one or two homology arm DNA sequences provided herein and a plant genome. In another aspect, a sequence of interest provided herein is integrated into a plant genome via NHEJ. In another aspect, a sequence of interest provided herein is integrated into a plant genome via microhomology-mediated end joining. In yet another aspect, a sequence of interest provided herein is randomly integrated into a plant genome via *Agrobacterium*-mediated T-strand integration.

In an aspect, integration of at least part of a sequence of interest provided herein results in one or more point mutations, one or more insertions, one or more deletions, an inversion, increased transcription of an endogenous locus, decreased transcription of an endogenous locus or any combination thereof. In an aspect, integration of at least part of a sequence of interest provided herein results in altered protein activity, altered production of RNAi polynucleotides, altered sequence of RNAi target sites, altered RNAi pathway activity, increased transcription of the sequence of interest, silencing of the integrated sequence of interest, or any combination thereof. Silencing technologies include, without limitations, antisense-, co-suppression-mediated mechanisms, and RNAi technologies, such as miRNA (e.g., U.S. Patent Application Publication 2006/0200878). In another aspect, integration of at least part of a sequence of interest causes targeted transcription, decreased transcription, enhanced transcription, or templated editing of a transgenic nucleic acid sequence present in the genome.

As used herein, the term "homology arm" or "homology arm DNA sequence" refers to a polynucleotide sequence that has at least 80%, at least 85%, at least 90%, at least 91%, at least 92%, at least 93%, at least 94%, at least 95%, at least 96%, at least 97%, at least 98%, at least 99% or 100% sequence identity to a target sequence in a plant or plant cell. A homology arm can comprise at least 5, at least 10, at least 15, at least 20, at least 25, at least 30, at least 40, at least 50, at least 100, at least 150, at least 200, at least 250, at least 300, at least 350, at least 400, at least 450, at least 500, at least 500, at least 550, at least 600, at least 650, at least 700, at least, 750, at least 800, at least 850, at least 900, at least 950, at least 1000, or at least 2500 nucleotides. In one aspect, the target sequence comprises a protein-coding sequence. In one aspect, the target sequence is a genic sequence. As used herein, a "genic" sequence is a nucleic acid sequence that encodes a protein or a non-protein-coding RNA. A genic sequence can include one or more introns. In another aspect, the target sequence is a non-genic sequence. As used herein, a "non-genic" sequence is a nucleic acid sequence that is not a genic sequence. In another aspect, the target sequence comprises a non-coding sequence. In yet another aspect, the target sequence comprises both a protein-coding sequence and a non-coding sequence. In another aspect, the target sequence does not comprise a gene or a portion of a gene. In some embodiments, the target sequence is linked to a gene of interest. In some embodiments, the target sequence is linked to a transgene integrated in the genome of a plant or plant cell.

As used herein, the term "target sequence" refers to a genomic locus selected for targeted integration of a sequence of interest. In some embodiments, the sequence of interest is integrated into the target sequence by HR or NHEJ. Depending upon the circumstances, the term target sequence can refer to the full-length nucleotide sequence of the genomic locus targeted for cleavage and recombination, or the nucleotide sequence of a portion of the genomic locus targeted for cleavage and recombination. The target sequence can be an endogenous genomic locus or a transgene. In one aspect, a target sequence is a genic sequence. In another aspect, a target sequence is a non-genic sequence.

As used herein, a "site-specific recombination site" or "site-specific target site" are used interchangeably to refer to a nucleic acid sequence where exogenous DNA is inserted by HR or by non-homologous recombination.

As used herein "site-specific enzyme target site" refers to the site that is cleaved by a nuclease introducing a double stranded break into the nucleic acid backbone. The site of the double-strand break may be a target site for introduction of a sequence of interest.

As used herein, "endogenous" refers to a nucleic acid sequence that exists naturally in the genome of a cell. In an aspect, a method provided herein is used to modify an endogenous locus so that the modified locus shares at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or at least 99.9% sequence identity as compared to an unmodified endogenous locus. In one aspect, an endogenous nucleic acid sequence undergoes "template editing." Template editing can occur via HR between a target sequence and a donor template after a double-stranded break occurs in or near the target sequence. As used herein, a "donor template" is a nucleic acid sequence that shares at least 60% at least 60%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or at least 99.9% sequence identity to at least a portion of a target sequence. In one aspect, a donor template provided herein comprises a sequence of interest. Template editing can introduce one or more point mutations, deletions, or insertions into a target sequence. In one aspect, the entire donor template, a portion of the donor template, a copy of the donor template, or a portion of a copy of the donor template integrates into the target sequence. One of ordinary skill in the art would recognize that such template editing would be analogous to an orthologous nucleic acid sequence, a paralogous nucleic acid sequence, an isogenic nucleic acid sequence, or a cisgenic nucleic acid sequence of the endogenous genome.

As used herein "exogenous" refers to a nucleic acid sequence that is not normally present in a cell, but can be introduced into a cell by one or more genetic, biochemical or other methods. In some embodiments, an exogenous nucleic acid sequence can be homologous to an endogenous molecule.

Cassettes

As used herein, the terms "cassette" or "expression cassette" refer to a nucleic acid sequence which may or may not be operably linked to one or more expression elements such as an enhancer, a promoter, a leader, an intron, a 5' untranslated region (UTR), a 3' UTR, or a transcription termination sequence. In one aspect, a cassette comprises a nucleic acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an endogenous nucleic acid sequence. In another aspect, the cassette comprises an exogenous nucleic acid sequence.

In one aspect, a cassette in a vector disclosed herein comprises at least one sequence selected from: a gene, a portion of a gene, an intergenic sequence, an enhancer, a promoter, an intron, an exon, a transcription termination sequence, a sequence encoding a chloroplast targeting peptide, a sequence encoding a mitochondrial targeting peptide, an insulator sequence, a sequence encoding an anti-sense RNA, a sequence encoding non-protein-coding RNA (npcRNA), a sequence encoding a recombinase, a sequence encoding a recombinase recognition site (for example, a lox site or a flp site), a sequence encoding an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof), a sequence encoding DNA guide, a sequence encoding an RNA-guided endonuclease (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof), a sequence encoding a CRISPR RNA, a sequence encoding a tracrRNA, a sequence encoding a fused guide RNA, a sequence encoding a zinc finger nuclease, a sequence encoding a TALEN, a landing pad, an editing template, a transgene, a sequence encoding a site-specific enzyme, a sequence encoding a site-specific enzyme target site, a sequence encoding a selection marker, a sequence encoding a cell factor that functions to increase DNA repair, a linker, a spacer, a restriction enzyme site, a sequence for templated genome editing, and any combination thereof. In some embodiments, the cassette is positioned between a first right border (RB1) and a second right border (RB2) such that the two T-strands resulting from initiation at RB1 and RB2 are essentially complementary to each other in at least a portion of the cassette. In some embodiments, the cassette is positioned adjacent to at least one LB DNA sequence. In some embodiments, the cassette is not positioned between RB DNA sequences. In some embodiments, the cassette is not positioned between a RB DNA sequence and a LB DNA sequence. As used herein, the term "landing pad" refers to a nucleic acid locus that is designed to be the locus for site-specific recombination. In some embodiments, landing pads may comprise one or more nucleic acid sequences that are not homologous to native sequences of the host organism. In some embodiments, landing pads may comprise one or more recognition sites for any of an endonuclease, a recombinase or a transposase. In some embodiments a landing pad may comprise one or more recognition sites for any of an endonuclease, a recombinase or a transposase flanking one or more nucleotide sequences substantially lacking homology with the genome of the host organism. In some embodiments, the one or more recognition sites are binding sites for DNA-binding domains (e.g., zinc finger proteins (ZFPs), meganucleases, or leucine zippers). In some examples, landing pads may comprise nucleotide sequences that have substantially no homology to regions of any sequenced target plant genome. In some embodiments, the landing pad may comprises any combination of one or more Zinc Finger Nuclease recognition sites, one or more meganuclease recognition sites, one or more targeting endonuclease recognition sites, one or more TALEN recognition sites, one or more recombinase recognition sites, or one or more transposase recognition sites. As used herein, the term "editing template" refers to a nucleic acid sequence that can be used for recombination with a target sequence. In one aspect, an editing template comprises a sequence that is at least 75%, 80%, 85%, 90%, 91%, 92%, 93%, 94%, 95%, 96%, 97%, 98%, or at least 99% identical to at least a portion of a target sequence. In some embodiments, the editing template comprises one or more nucleic acid changes compared to the target sequence.

As used herein, the term "cassette stack" refers to two or more expression cassettes which are physically linked in a vector. In some embodiments, two or more cassettes in a cassette stack are operably linked. In some embodiments, two or more cassettes in a cassette stack are not operably linked. In some embodiments, two or more cassettes in a cassette stack are flanked by one or more recombinase recognition sites. In some embodiments, two or more cassettes in a cassette stack are flanked by one or more a site-specific enzyme target sites. In some embodiments, two or more cassettes in a cassette stack may be separated by spacer sequences, insulator sequences, multiple cloning site sequences, one or more recombinase recognition sites, a sequence encoding a site-specific enzyme target site, a landing pad, homology arms, a RB DNA sequence or a LB DNA sequence. In some embodiments, the cassette stack is positioned between a first right border (RB1) and a second right border (RB2) such that the two T-strands resulting from initiation at RB1 and RB2 are essentially complementary to each other in at least a portion of the cassette stack. In some embodiments, the cassette stack is positioned adjacent to at least one LB DNA sequence. In some embodiments, the cassette stack is not positioned between RB DNA sequences. In some embodiments, the cassette stack is not positioned between a RB DNA sequence and a LB DNA sequence.

As used herein, the term "genomic locus" means a locatable region of genomic sequence, corresponding to a unit of inheritance. A genomic locus may comprise one or more regulatory regions, such as promoters, enhancers, 5' UTRs, intron regions, 3'UTRs, transcribed regions, and other functional sequence regions that may exist as native genes or transgenes in a plant or a mammalian genome.

As used herein, "gene" refers to a sequence that encodes a protein, or a sequence encoding a non-protein-coding RNA. As used herein, "protein-coding" refers to a polynucleotide encoding for the amino acids of a polypeptide. As used herein, "encoding" refers to a polynucleotide that can produce a functional unit (without being limited, for example, a protein, a microRNA, a transfer RNA, a ribosomal RNA, a small interfering RNA, a guide RNA, a tracer RNA, a single-guide RNA) via transcription and/or translation. A series of three nucleotide bases encodes one amino acid. As used herein, "expressed," "expression," or "expressing" refers to transcription of RNA from a DNA molecule. In one aspect, a sequence of interest provided herein comprises a protein-coding sequence.

As used herein, the term "npcRNA" refers to non-protein-coding RNA. Non-limiting examples of non-protein-coding RNA include a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA). In one aspect, a sequence of interest provided herein comprises a non-protein-coding RNA.

In one aspect, an expression cassette comprises at least one gene selected from a gene of agronomic interest, a DNA binding gene, a selectable marker gene, an RNAi construct, a site specific nuclease gene, a recombinant guide RNA of an RNA-guided nuclease (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof), an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, modified versions thereof), a DNA guide for an Argonaute protein, and any combination thereof. In an aspect, a gene provided herein comprises a promoter. In another aspect, a gene provided herein does not comprise a promoter.

Examples of suitable genes of agronomic interest envisioned by this disclosure would include but are not limited to genes for disease, insect, or pest tolerance (for example, virus tolerance, bacteria tolerance, fungus tolerance, nematode tolerance, arthropod tolerance, gastropod tolerance), herbicide tolerance, genes for quality improvements such as yield, nutritional enhancements, environmental or stress tolerances, or any desirable changes in plant physiology, growth, development, morphology or plant product(s) including starch production (U.S. Pat. Nos. 6,538,181; 6,538,179; 6,538,178; 5,750,876; 6,476,295), modified oils production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,541,259; 5,985,605; 6,171,640), biopolymers (U.S. Pat. Nos. RE37,543; 6,228,623; 5,958,745 and U.S. Patent Publication No. US20030028917). Also environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). Any of these or other genetic elements, methods, and transgenes can be used with the disclosure as will be appreciated by those of skill in the art in view of this disclosure.

In one aspect, an expression cassette provided herein comprises a nucleic acid sequence selected from an insecticidal resistance gene, an herbicide tolerance gene, a nitrogen use efficiency gene, a water use efficiency gene, a nutritional quality gene, a DNA binding gene, a selectable marker gene, an RNAi construct, a site specific nuclease gene, a guide RNA, and any combination thereof.

A gene can also include polynucleotide sequences that encode for other polynucleotide sequences such as a messenger RNA (mRNA). An mRNA produced from a nucleic acid molecule of this disclosure can contain a 5'-UTR leader sequence. This sequence can be derived from the promoter selected to express the gene and can be specifically modified so as to increase or decrease translation of the mRNA. A 5'-UTR can also be obtained from viral RNAs, from suitable eukaryotic genes, or from a synthetic gene sequence. Such "enhancer" sequences can be desirable to increase or alter the translational efficiency of the resultant mRNA. This disclosure is not limited to constructs where the non-translated region is derived from the 5'-UTR that accompanies the promoter sequence. Rather, the 5'-UTR sequence can be derived from unrelated promoters or genes (see, for example U.S. Pat. No. 5,362,865). Examples of non-translation leader sequences include maize and petunia heat shock protein leaders (U.S. Pat. No. 5,362,865), plant virus coat protein leaders, plant rubisco leaders, GmHsp (U.S. Pat. No. 5,659,122), PhDnaK (U.S. Pat. No. 5,362,865), AtAnt1, TEV (Carrington and Freed, *Journal of Virology*, (1990) 64: 1590-1597), and AGRtu.nos (GenBank Accession V00087; Bevan et al., *Nucleic Acids Research* (1983) 11:369-385). Other genetic components that serve to enhance expression or affect transcription or translational of a gene are also envisioned as genetic components.

A gene can further comprise a 3'-UTR. The provided 3'-UTRs can contain a transcriptional terminator, or an element having equivalent function, and a polyadenylation signal that functions in plants to cause the addition of polyadenylated nucleotides to the 3' end of an RNA molecule. Examples of suitable 3' regions are (1) the 3' transcribed, non-translated regions containing the polyadenylation signal of *Agrobacterium* Ti plasmid genes, such as the nopaline synthase (NOS; Fraley et al., *Proceedings of the National Academy of Sciences, USA* (1983) 80: 4803-4807) gene, and (2) plant genes such as the soybean storage protein genes and the small subunit of the ribulose-1,5-bisphosphate carboxylase (ssRUBISCO) gene. An example of a 3' region is that from the ssRUBISCO E9 gene from pea (European Patent Application 0385 962).

In an aspect, an expression cassette or sequence of interest provided herein may comprise a sequence encoding a cell factor that functions to increase DNA repair, where the protein is selected from the group consisting of a vir gene from the Ti plasmid, Rad51, Rad52, Rad2, a dominant-negative Ku70, or any combination thereof.

In one aspect, an expression cassette provided herein comprises a nucleic acid sequence that is not essentially homologous to an endogenous plant nucleic acid sequence. In another aspect, an expression cassette provided herein comprises a nucleic acid sequence that is not essentially homologous to an endogenous plant gene. In another aspect, an expression cassette provided herein comprises a nucleic acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an endogenous plant gene. In another aspect, an expression cassette provided herein comprises a nucleic acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an endogenous plant nucleic acid sequence.

Promoters

A promoter contains a sequence of nucleotide bases that signals RNA polymerase to associate with the DNA and to initiate transcription into mRNA using one of the DNA strands as a template to make a corresponding complementary strand of RNA. In an aspect, a promotor provided herein is a constitutive promoter. In another aspect, a promoter provided herein is a regulatable promoter. In an aspect, an expression cassette provided herein can comprise 1, 2, 3, 4, 5, 6, 7, 8, 9, 10, or more than 10 promoters. In an aspect, a promoter provided herein is located within a sequence of interest. In another aspect, a promoter provided herein is not located within a sequence of interest.

A number of promoters that are active in plant cells have been described in the literature. Such promoters would include but are not limited to the nopaline synthase (NOS) and octopine synthase (OCS) promoters that are carried on Ti plasmids of *Agrobacterium tumefaciens*, the caulimovirus promoters such as the cauliflower mosaic virus (CaMV) 19S and 35S promoters and the Figwort mosaic virus (FMV) 35S promoter, and the enhanced CaMV35S promoter (e35S). A variety of other plant gene promoters that are regulated in response to environmental, hormonal, chemical, and/or developmental signals, also can be used for expression of heterologous genes in plant cells, including, for instance, promoters regulated by (1) heat (Callis et al., *Plant Physiology*, (1988) 88: 965-968), (2) light (e.g., pea RbcS-3A promoter, Kuhlemeier et al., *Plant Cell*, (1989) 1: 471-478; maize RbcS promoter, Schaffner et al., *Plant Cell* (1991) 3: 997-1012); (3) hormones, such as abscisic acid (Marcotte et al., *Plant Cell*, (1989) 1: 969-976), (4) wounding (e.g., Siebertz et al., *Plant Cell*, (1989) 961-968); or other signals or chemicals. Tissue specific promoters are also known.

In some embodiments, a promoter is capable of causing sufficient expression to result in the production of an effective amount of the gene product of interest. Examples describing such promoters include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Molecular Biology* (1987) 9: 315-324), the CaMV 35S promoter (Odell et al., *Nature* (1985) 313: 810-812), the figwort mosaic virus 35S-promoter (U.S. Pat. Nos. 6,051,753; 5,378,619), the sucrose synthase promoter (Yang and Russell, *Proceedings of the National Academy of Sciences*, USA (1990) 87: 4144-4148), the R gene complex promoter (Chandler et al., *Plant Cell* (1989) 1: 1175-1183), and the chlorophyll a/b binding protein gene promoter, PC1SV (U.S. Pat. No. 5,850, 019), and AGRtu.nos (GenBank Accession V00087; Depicker et al., *Journal of Molecular and Applied Genetics* (1982) 1: 561-573; Bevan et al., 1983) promoters.

In some embodiments, promoter hybrids can be constructed to enhance transcriptional activity (U.S. Pat. No. 5,106,739), or to combine desired transcriptional activity, inducibility and tissue specificity or developmental specificity. Promoters that function in plants include but are not limited to promoters that are inducible, viral, synthetic, constitutive, temporally regulated, spatially regulated, and spatio-temporally regulated. Other promoters that are tissue-enhanced, tissue-specific, or developmentally regulated are also known in the art and envisioned to have utility in the practice of this disclosure.

Promoters used in the provided nucleic acid molecules and vectors of this disclosure can be modified, if desired, to affect their control characteristics. Promoters can be derived by means of ligation with operator regions, random or controlled mutagenesis, etc. Furthermore, the promoters can be altered to contain multiple "enhancer sequences" to assist in elevating gene expression.

Selectable Markers

In one aspect, a sequence of interest provided herein can comprise one or more selectable or screenable marker genes. In some embodiments the selectable or screenable marker gene aids in the identification of a transformed plant, or a product of agronomic utility. In some embodiments, DNA that serves as a selectable or screenable marker can function in a regenerable plant tissue to produce a compound that would confer upon the plant tissue resistance to an otherwise toxic compound. A number of selectable or screenable marker genes are known in the art and can be used. Genes for use as a selectable or screenable marker can include, but are not limited, to β-glucuronidase (GUS), green fluorescent protein (GFP), luciferase (LUC), genes conferring tolerance to antibiotics like kanamycin (Dekeyser et al., Plant Physiology (1989) 90: 217-223) or spectinomycin (e.g. spectinomycin aminoglycoside adenyltransferase (aadA); U.S. Pat. No. 5,217,902), genes that encode enzymes that give tolerance to herbicides like glyphosate (e.g. 5-enolpyruvylshikimate-3-phosphate synthase (EPSPS): Della-Cioppa et al., Bio/Technology (1987) 5: 579-584); U.S. Pat. Nos. 5,627,061; 5,633,435; 6,040,497; 5,094,945; WO04074443, and WO04009761; glyphosate oxidoreductase (GOX; U.S. Pat. No. 5,463,175); glyphosate decarboxylase (WO05003362 and US Patent Application 20040177399; or glyphosate N-acetyltransferase (GAT): Castle et al., Science (2004) 304: 1151-1154) U.S. Patent Publication 20030083480), dalapon (e.g. dehI encoding 2,2-dichloropropionic acid dehalogenase conferring tolerance to 2,2-dichloropropionic acid (Dalapon; WO9927116)), bromoxynil (haloarylnitrilase (Bxn) for conferring tolerance to bromoxynil (WO8704181A1; U.S. Pat. No. 4,810,648; WO8900193A), sulfonyl herbicides (e.g. acetohydroxyacid synthase or acetolactate synthase conferring tolerance to acetolactate synthase inhibitors such as sulfonylurea, imidazolinone, triazolopyrimidine, pyrimidyloxybenzoates and phthalide; (U.S. Pat. Nos. 6,225,105; 5,767,366; 4,761,373; 5,633,437; 6,613,963; 5,013,659; 5,141,870; 5,378,824; 5,605,011); encoding ALS, GST-II), bialaphos or phosphinothricin or derivatives (e.g. phosphinothricin acetyltransferase (bar) conferring tolerance to phosphinothricin or glufosinate (U.S. Pat. Nos. 5,646,024, 5,561,236, 5,276,268; 5,637,489; 5,273,894; and EP 275,957), atrazine (encoding GST-III), dicamba (dicamba monooxygenase; U.S. Patent Application Publications 20030115626, 20030135879), or sethoxydim (modified acetyl-coenzyme A carboxylase for conferring tolerance to cyclohexanedione (sethoxydim) and aryloxyphenoxypropionate (haloxyfop) (U.S. Pat. No. 6,414,222), among others. Other selection procedures can also be implemented including positive selection mechanisms (e.g. use of the manA gene of Escherichia coli, allowing growth in the presence of mannose), and dual selection (e.g. simultaneously using 75-100 ppm spectinomycin and 3-10 ppm glufosinate, or 75 ppm spectinomycin and 0.2-0.25 ppm dicamba) and would still fall within the scope of this disclosure. Use of spectinomycin at a concentration of about 25-1000 ppm, such as at about 150 ppm, is also contemplated.

In one aspect, a selectable or screenable marker provided herein is a positive selection marker. A positive selection marker confers an advantage to a cell comprising such marker. In an aspect, a sequence of interest provided herein comprises one or more positive selection markers. In some embodiments, a positive selection marker confers antibiotic resistance or herbicide resistance. In another aspect, a selectable or screenable marker provided herein is a negative selection marker. In some embodiments, a sequence of interest provided herein comprises one or more negative selection markers. In another aspect, a selectable or screenable marker provided herein is both a positive selection marker and a negative selection marker. A negative selectable marker provided herein can be a lethal or non-lethal negative selectable marker. Examples of non-lethal negative selectable markers include U.S. Publication No. 2004-0237142, such as GGPP synthases, GA 2-oxidase gene sequences, isopentenyltransferase (IPT), CKI1 (cytokinin-independent 1), ESR-2, ESR1-A, auxin-producing genes, such as indole-3-acetic acid (IAA), iaaM, iaah, roLABC, genes that result in over-expression of ethylene biosynthetic enzymes, VP1 genes, AB13 genes, LEC1 genes, and Bas1 genes for example. A non-lethal negative selectable marker gene can be included on any nucleic acid molecule provided herein. A non-lethal negative selectable marker gene provided herein is a gene resulting in the over-expression of a class of enzymes that use substrates of the gibberellic acid (GA) biosynthetic pathway, but that do not result in the production of bioactive GA. In another aspect, a nucleic acid molecule provided herein comprises a non-lethal negative selectable marker gene such as a phytoene synthase gene from Erwinia herbicola (crtB).

In one aspect, by employing a selectable or screenable marker, one can provide or enhance the ability to identify transformants. In some embodiments, the selectable or screenable marker imparts a distinct phenotype to cells expressing the marker protein and often provide a means to more efficiently distinguish such transformed cells from cells that do not have the selectable or screenable marker. Such genes may encode either a selectable or screenable marker, depending on whether the marker confers a trait which one can "select" for by chemical means, such as through the use of a selective agent (for example, an herbicide, or an antibiotic), or whether it is simply a trait that one can identify through observation (for example, expression of GFP) or testing or "screening". Of course, many examples of suitable marker proteins are known to the art and can be employed in the practice of the invention.

Included within the terms "selectable" or "screenable markers" also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, by ELISA; or small active enzymes detectable in extracellular solution (for example, α-amylase, β-lactamase, phosphinothricin acetyltransferase); and proteins that are inserted or trapped in the cell wall (for example, proteins that include a leader sequence such as that found in the expression unit of extensin or tobacco PR-S).

Many selectable marker coding regions are known and could be used including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from Klebsiella ozaenae which confers resistance to bromoxynil (Stalker et al., 1988); a mutant acetolactate synthase (ALS) which confers resistance to imidazolinone, sulfonylurea, or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

Examples of screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Site-Specific Enzymes

In an aspect, a sequence of interest provided herein comprises polynucleotides encoding at least 1, at least 2, at least 3, at least 4, at least 5, at least 6, at least 7, at least 8, at least 9, or at least 10 site-specific enzymes. In another aspect, a plant cell provided herein already comprises a polynucleotide encoding a site-specific enzyme. In an aspect, a polynucleotide encoding a site-specific enzyme provided herein is stably transformed into a plant cell. In another aspect, a polynucleotide encoding a site-specific enzyme provided herein is transiently transformed into a plant cell. In another aspect, a polynucleotide encoding a site-specific enzyme is under the control of a regulatable promoter, a constitutive promoter, a tissue specific promoter, or any promoter useful for expression of the site-specific enzyme.

In one aspect, a vector comprises in cis a cassette encoding a site-specific enzyme and a sequence of interest such that when contacted with the genome of a plant cell, the site-specific enzyme enables site-specific integration of the sequence of interest. In one aspect, a first vector comprises a cassette encoding a site-specific enzyme and a second vector comprises a sequence of interest such that when contacted with the genome of a plant cell, the site-specific enzyme provided in trans enables site-specific integration of the sequence of interest.

As used herein, the term "site-specific enzyme" refers to any enzyme that can cleave a nucleotide sequence in a site-specific manner. In an aspect, a site-specific enzyme provided herein is selected from the group consisting of an endonuclease (without being limiting, for example, a meganuclease, a zinc-finger nuclease (ZFN), a transcription activator-like effector nucleases (TALEN), an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), an RNA-guided nuclease (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof); a recombinase (without being limiting, for example, a serine recombinase attached to a DNA recognition motif, a tyrosine recombinase attached to a DNA recognition motif); a transposase (without being limiting, for example, a DNA transposase attached to a DNA binding domain); or any combination thereof.

In an aspect, a tyrosine recombinase attached to a DNA recognition motif provided herein is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA binding domain. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Site-specific nucleases, such as meganucleases, ZFNs, TALENs, Argonaute proteins (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof), Cas9 nucleases (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof), induce a double-strand DNA break at the target site of a genomic sequence that is then repaired by the natural processes of HR or NHEJ. Sequence modifications then occur at the cleaved sites, which can include deletions or insertions that result in gene disruption in the case of NHEJ, or integration of nucleic acid sequences by HR.

In an aspect, a vector or sequence of interest provided herein can comprise a nucleic acid sequence encoding a zinc finger nuclease. ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

In an aspect, a vector or sequence of interest provided herein can comprise a nucleic acid sequence encoding a transcription activator-like effector nuclease (TALEN). TALENs are artificial restriction enzymes generated by fusing the transcription activator-like effector (TALE) DNA binding domain to a nuclease domain. In some embodiments, the nuclease is selected from a group consisting of PvuII, MutH, TevI and FokI, AlwI, MlyI, SbfI, SdaI, StsI, CleDORF, Clo051, Pept071. When each member of a TALEN pair binds to the DNA sites flanking a target site, the FokI monomers dimerize and cause a double-stranded DNA break at the target site.

The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One.* 8: e82539). MutH is capable of introducing strand-specific nicks in DNA (see Gabsalilow et al. 2013. *Nucleic Acids Research.* 41: e83). TevI introduces double-stranded breaks in DNA at targeted sites (see Beurdeley et al., 2013. *Nature Communications.* 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39:e82; and tale-nt.cac.cornell.edu/about.

In an aspect, a vector or sequence of interest provided herein can comprise a nucleic acid sequence encoding a meganuclease. Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp).

The engineering of meganucleases is more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

In an aspect, a vector provided herein can comprise any combination of a nucleic acid sequence encoding an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof), and optionally, a sequence encoding DNA guide.

In an aspect, a vector provided herein can comprise any combination of a nucleic acid sequence encoding a RNA-guided Cas9 nuclease (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof); and, optionally, the guide RNA necessary for targeting the respective nucleases.

Cas9 nucleases are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA.

Site-Specific Enzyme Target Sites

In an aspect, a nucleic acid molecule provided herein comprises at least 1, at least 2, at least 3, at least 4, at least 5, at least 6, at least 7, at least 8, at least 9, or at least 10 site-specific enzyme target sites. In an aspect, a vector or sequence of interest provided herein comprises a Cre/lox recombination site, a Flp/FRT recombination site, an endonuclease recognition site, a TALEN site, or any combination thereof. In another aspect, a vector or sequence of interest provided herein comprises a Cre recombinase or a Flp recombination system. In an aspect, a recombination system provided herein can act in cis. In another aspect, a recombination system provided herein can act in trans.

In an aspect, a site-specific enzyme target site provided herein is at least 10, at least 20, at least 30, at least 40, at least 50, at least 75, at least 100, at least 125, at least 150, at least 200, at least 250, at least 300, at least 400, or at least 500 nucleotides.

The Flp-FRT site-directed recombination system comes from the 2µ plasmid from the baker's yeast *Saccharomyces cerevisiae*. In this system, Flp recombinase (flippase) recombines sequences between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites.

Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

Methods and Compositions for Use of Gene Modification in Plants

In one aspect, the instant disclosure provides a Rhizobiales cell comprising at least one vector that is capable of forming two essentially complementary T-strands. In another aspect, the instant disclosure provides an *Agrobacterium* cell comprising at least one vector that is capable of forming two essentially complementary T-strands.

In one aspect, the instant disclosure provides a method of increasing the rate of site directed integration of a sequence of interest, comprising contacting a plant cell with a Rhizobiales cell capable of transforming the plant cell, where the Rhizobiales cell comprises at least one vector. In another aspect, the instant disclosure provides a method of transforming a plant cell, comprising contacting the plant cell with a Rhizobiales cell capable of transforming the plant cell, where the Rhizobiales cell comprises at least one vector capable of forming two T-strands that are essentially complementary in at least a portion of a of the T-strands.

In one embodiment, a vector disclosed herein comprises a first right border DNA sequence (RB1), a second right border DNA sequence (RB2), and at least one sequence of interest, where the RB1 is positioned in the vector to initiate synthesis of a first T-strand such that the sequence of interest is in the sense orientation from the 5' to 3' end of the first T-strand; and the RB2 is positioned in the vector to initiate synthesis of a second T-strand such that the sequence of interest is in the anti-sense orientation from the 5' to 3' end of the second T-strand, and where the two T-strands resulting from initiation at RB1 and RB2 are essentially complementary to each other.

In another embodiment, a vector disclosed herein comprises a first right border DNA sequence (RB1), a second right border DNA sequence (RB2), at least one sequence of interest, a first left border DNA sequence (LB1), and a second left border DNA sequence (LB2), where the vector is configured such that the RB1 is paired with the LB1, which are positioned in the vector to initiate (RB1) and terminate (LB1) synthesis of a first T-strand such that the sequence of interest is in the sense orientation from the 5' to 3' end of the first T-strand; and the RB2 is paired with the LB2, which are positioned in the vector to initiate (RB2) and terminate (LB2) synthesis of a second T-strand such that the sequence of interest is in an anti-sense orientation relative to the sequence of interest in the first T-strand, and where the two T-strands resulting from initiation at RB1 and RB2 are essentially complementary in at least a portion of the sequence of interest.

In another embodiment, a vector disclosed herein comprises a first right border DNA sequence (RB1), a second right border DNA sequence (RB2), at least one sequence of interest, and a left border DNA sequence (LB), where the vector is configured such that the RB1 is paired with the LB, which are positioned in the vector to initiate (RB1) and terminate (LB) synthesis of a first T-strand such that the sequence of interest is in the sense orientation from the 5' to 3' end of the first T-strand; and the RB2 initiates synthesis of a second T-strand such that the sequence of interest is in an anti-sense orientation relative to the sequence of interest in the first T-strand, and where the two T-strands resulting from initiation at RB1 and RB2 are essentially complementary in at least a portion of the sequence of interest.

In another embodiment, a vector disclosed herein comprises a first right border DNA sequence (RB1), a second right border DNA sequence (RB2), at least one sequence of interest, and a left border DNA sequence (LB), where the vector is configured such that the RB1 initiates synthesis of a first T-strand such that the sequence of interest is in the sense orientation from the 5' to 3' end of the first T-strand; and the RB2 is paired with the LB, which are positioned in the vector to initiate (RB2) and terminate (LB) synthesis of a second T-strand such that the sequence of interest is in an anti-sense orientation relative to the sequence of interest in the first T-strand, and where the two T-strands resulting from initiation at RB1 and RB2 are essentially complementary in at least a portion of the sequence of interest.

In another embodiment, a vector disclosed herein comprises a first sequence of interest and a second sequence of interest, where the first sequence of interest is essentially identical to the second sequence of interest; and the vector further comprises a first right border DNA sequence (RB1) with a first left border DNA sequence (LB1) which are positioned in the vector to initiate (RB1) and terminate (LB1) synthesis of a first T-strand such that the first sequence of interest is in the sense orientation from the 5' to 3' end of the first T-strand; and the vector further comprises a second right border DNA sequence (RB2) and a second left border DNA sequence (LB2) which are positioned in the vector to initiate (RB2) and terminate (LB2) synthesis of a second T-strand such that the second sequence of interest is in an anti-sense orientation relative to the first sequence of interest in the first T-strand, and where the two T-strands resulting from initiation at RB1 and RB2 are essentially complementary in at least a portion of the first sequence of interest and the second sequence of interest.

In another embodiment, a vector disclosed herein comprises a first sequence of interest and a second sequence of interest, where the first sequence of interest is essentially identical to the second sequence of interest; and the vector further comprises a first right border DNA sequence (RB1)

with a left border DNA sequence (LB) which are positioned in the vector to initiate (RB1) and terminate (LB) synthesis of a first T-strand such that the first sequence of interest is in the sense orientation from the 5' to 3' end of the first T-strand; and the vector further comprises a second right border DNA sequence (RB2) which initiates synthesis of a second T-strand such that the second sequence of interest is in an anti-sense orientation relative to the first sequence of interest in the first T-strand, and where the two T-strands resulting from initiation at RB1 and RB2 are essentially complementary in at least a portion of the first sequence of interest and the second sequence of interest.

In another embodiment, a vector disclosed herein comprises a first sequence of interest and a second sequence of interest, where the first sequence of interest is essentially identical to the second sequence of interest; and the vector further comprises a first right border DNA sequence (RB1) which initiates synthesis of a first T-strand such that the first sequence of interest is in the sense orientation from the 5' to 3' end of the first T-strand; and the vector further comprises a second right border DNA sequence (RB2) and a left border DNA sequence (LB) which are positioned in the vector to initiate (RB2) and terminate (LB) synthesis of a second T-strand such that the second sequence of interest is in an anti-sense orientation relative to the first sequence of interest in the first T-strand, and where the two T-strands resulting from initiation at RB1 and RB2 are essentially complementary in at least a portion of the first sequence of interest and the second sequence of interest.

In another embodiment, a vector disclosed herein comprises a first sequence of interest and a second sequence of interest, where the first sequence of interest is essentially identical to the second sequence of interest; and the vector further comprises a first right border DNA sequence (RB1) to initiate synthesis of a first T-strand such that the first sequence of interest is in the sense orientation from the 5' to 3' end of the first T-strand; and the vector further comprises a second right border DNA sequence (RB2) which initiates synthesis of a second T-strand such that the second sequence of interest is in an anti-sense orientation relative to the first sequence of interest in the first T-strand, and where the two T-strands resulting from initiation at RB1 and RB2 are essentially complementary in at least a portion of the first sequence of interest and the second sequence of interest.

In yet another embodiment, a Rhizobiales cell disclosed herein comprises at least a first vector and a second vector, where each vector comprises essentially identical sequences of interest, and where the first vector comprises a first right border DNA sequence (RB1) and a first left border DNA sequence (LB1) which are positioned in the first vector to initiate (RB1) and terminate (LB1) synthesis of a first T-strand such that the sequence of interest is in the sense orientation from the 5' to 3' end of the first T-strand; and the second vector comprises a second right border DNA sequence (RB2) and a second left border DNA Sequence (LB2) which are positioned in the second vector to initiate (RB2) and terminate (LB2) synthesis of a second T-strand such that the sequence of interest is in an anti-sense orientation relative to the sequence of interest in the first T-strand, and where the two T-strands resulting from initiation at RB1 and RB2 are essentially complementary to each other in at least a portion of the sequence of interest.

In another embodiment, a Rhizobiales cell provided herein comprises at least a first vector and a second vector, where each vector comprises essentially identical sequences of interest, and where the first vector comprises a first right border DNA sequence (RB1) and a left border DNA sequence (LB) which are positioned in the first vector to initiate (RB1) and terminate (LB) synthesis of a first T-strand such that the sequence of interest is in the sense orientation from the 5' to 3' end of the first T-strand; and the second vector comprises a second right border DNA sequence (RB2) which initiates synthesis of a second T-strand such that the sequence of interest is in an anti-sense orientation relative to the sequence of interest in the first T-strand, and where the two T-strands resulting from initiation at RB1 and RB2 are essentially complementary to each other in at least a portion of the sequence of interest.

In another embodiment, a Rhizobiales cell provided herein comprises at least a first vector and a second vector, where each vector comprises essentially identical sequences of interest, and where the first vector comprises a first right border DNA sequence (RB1) which initiates synthesis of a first T-strand such that the sequence of interest is in the sense orientation from the 5' to 3' end of the first T-strand; and the second vector comprises a second right border DNA sequence (RB2) and a left border DNA Sequence (LB) which are positioned in the second vector to initiate (RB2) and terminate (LB) synthesis of a second T-strand such that the sequence of interest is in an anti-sense orientation relative to the sequence of interest in the first T-strand, and where the two T-strands resulting from initiation at RB1 and RB2 are essentially complementary to each other in at least a portion of the sequence of interest.

In another embodiment, a Rhizobiales cell provided herein comprises at least a first vector and a second vector, where each vector comprises essentially identical sequences of interest, and where the first vector comprises a first right border DNA sequence (RB1) which initiates synthesis of a first T-strand such that the sequence of interest is in the sense orientation from the 5' to 3' end of the first T-strand; and the second vector comprises a second right border DNA sequence (RB2) which initiates synthesis of a second T-strand such that the sequence of interest is in an anti-sense orientation relative to the sequence of interest in the first T-strand, and where the two T-strands resulting from initiation at RB1 and RB2 are essentially complementary to each other in at least a portion of the sequence of interest.

In one aspect, methods provided in the instant disclosure comprise two or more vectors, where the two or more vectors are in one Rhizobiales cell. In another aspect, methods provided in the instant disclosure comprise two or more vectors, where the two or more vectors are in two or more Rhizobiales cells. For example, a first Rhizobiales cell comprises a first vector, and a second Rhizobiales cell comprises a second vector.

In one aspect, the instant disclosure provides a method of increasing the rate of site directed integration of a sequence of interest, comprising contacting the plant cell with two or more Rhizobiales cells capable of transforming the plant cell, where the two or more Rhizobiales cells each contain one of at least two vectors capable of forming two essentially complementary T-strands.

In another aspect, the instant disclosure provides a method of transforming a plant cell, comprising contacting the plant cell with two or more Rhizobiales cells capable of transforming the plant cell, where the two or more Rhizobiales cells each contain one of at least two vectors capable of forming two essentially complementary T-strands. In another aspect, the instant disclosure provides a method of increasing the rate of site directed integration of a sequence of interest, comprising contacting a plant cell with two or more Rhizobiales cells, where the two or more Rhizobiales cells each contain one of at least two vectors capable of forming two essentially complementary T-strands.

In one embodiment, a first Rhizobiales cell and a second Rhizobiales cell provided herein contain at least a first vector and a second vector, respectively, where each vector comprises an essentially identical sequence of interest, and where the first vector comprises a first right border DNA sequence (RB1), and where the RB1 is positioned in the vector to initiate synthesis of a first T-strand such that the sequence of interest is in the sense orientation from the 5' to 3' end of the first T-strand; and the second vector comprises a second right border DNA sequence (RB2) which is positioned in the vector to initiate synthesis of a second T-strand such that the sequence of interest is in the anti-sense orientation relative to the sequence of interest in the first T-strand, and where the two T-strands resulting from initiation at RB1 and RB2 are essentially complementary in at least a portion of the sequence of interest.

In another embodiment, a first Rhizobiales cell and a second Rhizobiales cell provided herein contain at least a first vector and a second vector, respectively, where each vector comprises an essentially identical sequence of interest, and where the first vector comprises a first right border DNA sequence (RB1) and a first left border DNA sequence (LB1) which are positioned in the first vector to initiate (RB1) and terminate (LB1) synthesis of a first T-strand such that the sequence of interest is in the sense orientation from the 5' to 3' end of the first T-strand; and the second vector comprises a second right border DNA sequence (RB2) and a second left border DNA sequence (LB2) which are positioned in the second vector to initiate (RB2) and terminate (LB2) synthesis of a second T-strand such that the sequence of interest is in an anti-sense orientation from the 5' to 3' end of the second T-strand, and where the sequence of interest in the two T-strands resulting from initiation at RB1 and RB2 are essentially complementary to each other.

In one embodiment, the instant disclosure provides a method comprising a first Rhizobiales cell and a second Rhizobiales cell, where each Rhizobiales cell contains at least one of two vectors, where each vector comprises an essentially identical sequence of interest, and where the first vector comprises a first right border DNA sequence (RB1), and where the RB1 is positioned in the vector to initiate synthesis of a first T-strand such that the sequence of interest is in the sense orientation from the 5' to 3' end of the first T-strand; and the second vector comprises a second right border DNA sequence (RB2) which is positioned in the vector to initiate synthesis of a second T-strand such that the sequence of interest is in the anti-sense orientation relative to the sequence of interest in the first T-strand, and wherein the two T-strands resulting from initiation at RB1 and RB2 are essentially complementary in at least a portion of the sequence of interest.

In another embodiment, the instant disclosure provides a method comprising a first Rhizobiales cell and a second Rhizobiales cell, where each Rhizobiales cell contains at least one of two vectors, where each vector comprises an essentially identical sequence of interest, and where the first vector comprises a first right border DNA sequence (RB1) and a first left border DNA sequence (LB1) which are positioned in the first vector to initiate (RB1) and terminate (LB1) synthesis of a first T-strand such that the sequence of interest is in the sense orientation from the 5' to 3' end of the first T-strand; and the second vector comprises a second right border DNA sequence (RB2) and a second left border DNA sequence (LB2) which are positioned in the second vector to initiate (RB2) and terminate (LB2) synthesis of a second T-strand such that the sequence of interest is in an anti-sense orientation from the 5' to 3' end of the second T-strand, and wherein the sequence of interest in the two T-strands resulting from initiation at RB1 and RB2 are essentially complementary to each other.

In another embodiment, the instant disclosure provides a method comprising a first Rhizobiales cell and a second Rhizobiales cell, where each Rhizobiales cell contains at least one of two vectors, where each vector comprises an essentially identical sequence of interest, and where the first vector comprises a first right border DNA sequence (RB1) and a left border DNA sequence (LB) which are positioned in the first vector to initiate (RB1) and terminate (LB) synthesis of a first T-strand such that the sequence of interest is in the sense orientation from the 5' to 3' end of the first T-strand; and the second vector comprises a second right border DNA sequence (RB2) to initiate synthesis of a second T-strand such that the sequence of interest is in an anti-sense orientation from the 5' to 3' end of the second T-strand, and wherein the sequence of interest in the two T-strands resulting from initiation at RB1 and RB2 are essentially complementary to each other.

In another embodiment, the instant disclosure provides a method comprising a first Rhizobiales cell and a second Rhizobiales cell, where each Rhizobiales cell contains at least one of two vectors, where each vector comprises an essentially identical sequence of interest, and where the first vector comprises a first right border DNA sequence (RB1) initiate synthesis of a first T-strand such that the sequence of interest is in the sense orientation from the 5' to 3' end of the first T-strand; and the second vector comprises a second right border DNA sequence (RB2) and a left border DNA sequence (LB) which are positioned in the second vector to initiate (RB2) and terminate (LB) synthesis of a second T-strand such that the sequence of interest is in an anti-sense orientation from the 5' to 3' end of the second T-strand, and wherein the sequence of interest in the two T-strands resulting from initiation at RB1 and RB2 are essentially complementary to each other.

In another embodiment, at least one vector disclosed herein comprises an RB and a LB and where the vector further comprises between the RB and LB: (i) a first sequence of interest in a sense orientation relative to the RB, (ii) a spacer, and (iii) a second sequence of interest in an anti-sense orientation relative to the RB, where the first sequence of interest and the second sequence of interest are essentially complementary and after synthesis of the T-strand anneal to form a double-stranded DNA.

In one aspect, the integration of at least part of the sequence of interest in a vector results in a point mutation, an insertion, a deletion, an inversion, increased transcription of an endogenous genomic locus, decreased transcription of an endogenous genomic locus, altered protein activity, increased transcription of the sequence of interest, decreased transcription of the integrated sequence of interest, or a combination thereof.

In one aspect, the sequence of interest in the vector further comprises at least one, at least two, at least three, at least four, at leave five, at least six, at least seven, at least eight, at least nine, or at least ten site-specific enzyme target sites. Examples of a site-specific enzyme target site include, but are not limited to, a Cre/lox recombination site, a Flp/FRT recombination site, a endonuclease recognition site, and a TALEN site.

In one aspect, the Rhizobiales cell is selected from an *Agrobacterium* spp., a *Bradyrhizobium* spp., a *Mesorhizobium* spp., an *Ochrobactrum* spp., a *Phyllobacterium* spp., a

*Rhizobium* spp., *Sinorhizobium* spp, and an *Ensifer* spp. In another aspect, the Rhizobiales cell is an *Agrobacterium* cell. In yet another aspect, the Rhizobiales cell is an *Agrobacterium tumefaciens* cell. In another aspect, the Rhizobiales cell further contains a vector comprising one or more gene expression cassettes with sequence encoding a cell factor that functions to increase DNA repair, one or more *Agrobacterium* Ti plasmid vir genes, one or more selectable marker genes, an origin of replication, or any combination thereof.

Methods for Increasing Rates of Site-Directed Integration by Prolonged Co-Culturing In an aspect, the instant disclosure provides a method of increasing the rate of site-directed integration of a sequence of interest in a plant genome, comprising contacting at least one plant cell on a co-culture medium for at least two days, at least 3 days, at least 4 days or at least 5 days with a Rhizobiales cell capable of transforming the plant cell, wherein the Rhizobiales cell comprises at least one vector described in the instant disclosure.

In another aspect, the instant disclosure provides a method of transforming a plant genome, comprising contacting at least one plant cell on a co-culture medium for at least two days, at least 3 days, at least 4 days, or at least 5 days with at least one Rhizobiales cell capable of transforming the plant cell, where the Rhizobiales cell comprises at least one vector capable of forming two essentially complementary T-strands.

In one aspect, the contacting comprises co-culturing the plant cell with a Rhizobiales cell for at least three days, at least four days, at least five days, at least six days, at least seven days, at least eight days, at least nine days, or at least ten days. In one aspect, the contacting comprises co-culturing the plant cell with a Rhizobiales cell for at least 48 hours, at least 49 hours, at least 50 hours, at least 51 hours, at least 52 hours, at least 53 hours, at least 54 hours, at least 55 hours, at least 56 hours, at least 57 hours, at least 58 hours, at least 59 hours, at least 60 hours, at least 61 hours, at least 62 hours, at least 63 hours, at least 64 hours, at least 65 hours, at least 66 hours, at least 67 hours, at least 68 hours, at least 69 hours, at least 70 hours, at least 71 hours, at least 72 hours, at least 73 hours, at least 74 hours, at least 75 hours, at least 76 hours, at least 77 hours, at least 78 hours, at least 79 hours, at least 80 hours, at least 81 hours, at least 82 hours, at least 83 hours, at least 84 hours, at least 85 hours, at least 86 hours, at least 87 hours, at least 88 hours, at least 89 hours, at least 90 hours, at least 91 hours, at least 92 hours, at least 93 hours, at least 94 hours, at least 95 hours, at least 96 hours, at least 97 hours, at least 98 hours, at least 99 hours, at least 100 hours, at least 101 hours, at least 102 hours, at least 103 hours, at least 104 hours or at least 105 hours. In one aspect, a Rhizobiales cell is selected from the group consisting of an *Agrobacterium* spp. cell, a *Bradyrhizobium* spp. cell, a *Mesorhizobium* spp. cell, an *Ochrobactrum* spp. cell, a *Phyllobacterium* spp. cell, a *Rhizobium* spp. cell, and a *Sinorhizobium* spp. cell. In a further aspect, an *Agrobacterium* spp. cell is selected from the group consisting of an *Agrobacterium tumefaciens* cell and an *Agrobacterium rhizogenes* cell.

In one aspect, the method further comprises detecting the integration of at least a fragment of the sequence of interest of the vector in the at least one plant cell. In one aspect, the at least one fragment of the sequence of interest in the vector is integrated into the plant genome by HR. In another aspect, the at least one fragment of the sequence of interest in the vector is integrated into the plant genome by NHEJ.

In one aspect, the method also comprises selecting the plant call based on the presence of the at least one fragment of the sequence of interest in the vector integrated into the plant genome. In a further aspect, the method further comprises regenerating a transgenic plant form the selected plant cell.

In one aspect, a method or system for site-specific modification of a target nucleic acid sequence provided herein involves homologous recombination. In another aspect, a method or system for site-specific modification of a target nucleic acid sequence provided herein involves non-homologous end joining. In yet another aspect, a method or system for site-specific modification of a target nucleic acid sequence provided herein comprises non-homologous end joining that further comprises the introduction of an insertion and/or deletion of one or more, two or more, three or more, four or more, five or more, six or more, seven or more, eight or more, nine or more, ten or more, twenty or more, fifty or more, or one hundred or more nucleotides into the target nucleic acid sequence.

Transformation Methods

Methods of transforming plant cells are well known by persons of ordinary skill in the art. For instance, specific instructions for transforming plant cells by microprojectile bombardment with particles coated with recombinant DNA are found in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat); U.S. Pat. No. 6,002,070 (rice); U.S. Pat. No. 7,122,722 (cotton); U.S. Pat. No. 6,051,756 (*Brassica*); U.S. Pat. No. 6,297,056 (*Brassica*); US Patent Publication 20040123342 (sugarcane) and *Agrobacterium*-mediated transformation is described in U.S. Pat. No. 5,159,135 (cotton); U.S. Pat. No. 5,824,877 (soybean); U.S. Pat. No. 5,591,616 (corn); U.S. Pat. No. 6,384,301 (soybean); U.S. Pat. No. 5,750,871 (*Brassica*); U.S. Pat. No. 5,463,174 (*Brassica*) 5,188,958 (*Brassica*), all of which are incorporated herein by reference. Methods for transforming other plants can be found in, for example, Compendium of Transgenic Crop Plants (2009) Blackwell Publishing. Any appropriate method known to those skilled in the art can be used to transform a plant cell with any of the nucleic acid molecules provided herein.

In one aspect, a method provided herein stably transforms a plant cell. In another aspect, a method provided herein transiently transforms a plant cell. In an aspect, a method of transforming a plant cell provided herein comprises a biolistic transformation or a bacteria-mediated transformation. In an aspect, a method of transforming a plant cell provided herein comprises bacteria-mediated transformation that further comprises contacting the plant cell with a Rhizobiales cell, where the Rhizobiales cell is capable of transforming the plant cell.

Transformation methods to provide transgenic plant cells and transgenic plants containing stably integrated nucleic acid molecules provided herein are preferably practiced in tissue culture on media and in a controlled environment. "Media" refers to the numerous nutrient mixtures that are used to grow cells in vitro, that is, outside of the intact living organism.

In one aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction.

Recipient cell targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a stomata cell, a trichome cell, a root hair cell, a storage root cell, or a tuber cell. In another aspect, this disclosure provides a protoplast. In another aspect, this disclosure provides a plant callus cell. Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189.

In one aspect, the instant disclosure provides a plant cell transformed by any method provided herein. In an aspect, a plant cell provided herein is selected from the group consisting of an Acacia cell, an alfalfa cell, an aneth cell, an apple cell, an apricot cell, an artichoke cell, an arugula cell, an asparagus cell, an avocado cell, a banana cell, a barley cell, a bean cell, a beet cell, a blackberry cell, a blueberry cell, a broccoli cell, a Brussels sprout cell, a cabbage cell, a canola cell, a cantaloupe cell, a carrot cell, a cassava cell, a cauliflower cell, a celery cell, a Chinese cabbage cell, a cherry cell, a cilantro cell, a citrus cell, a clementine cell, a coffee cell, a corn cell, a cotton cell, a cucumber cell, a Douglas fir cell, an eggplant cell, an endive cell, an escarole cell, an eucalyptus cell, a fennel cell, a fig cell, a forest tree cell, a gourd cell, a grape cell, a grapefruit cell, a honey dew cell, a jicama cell, kiwifruit cell, a lettuce cell, a leek cell, a lemon cell, a lime cell, a Loblolly pine cell, a mango cell, a maple tree cell, a melon cell, a mushroom cell, a nectarine cell, a nut cell, an oat cell, an okra cell, an onion cell, an orange cell, an ornamental plant cell, a papaya cell, a parsley cell, a pea cell, a peach cell, a peanut cell, a pear cell, a pepper cell, a persimmon cell, a pine cell, a pineapple cell, a plantain cell, a plum cell, a pomegranate cell, a poplar cell, a potato cell, a pumpkin cell, a quince cell, a radiata pine cell, a radicchio cell, a radish cell, a rapeseed cell, a raspberry cell, a rice cell, a rye cell, a sorghum cell, a Southern pine cell, a soybean cell, a spinach cell, a squash cell, a strawberry cell, a sugar beet cell, a sugarcane cell, a sunflower cell, a sweet corn cell, a sweet potato cell, a sweetgum cell, a tangerine cell, a tea cell, a tobacco cell, a tomato cell, a turf cell, a vine cell, watermelon cell, a wheat cell, a yam cell, and a zucchini cell. In another aspect, a plant cell provided herein is selected from the group consisting of a corn cell, a soybean cell, a canola cell, a cotton cell, a wheat cell, and a sugarcane cell.

In another aspect, a plant cell provided herein is selected from the group consisting of a corn immature embryo cell, a corn mature embryo cell, a corn seed cell, a soybean immature embryo cell, a soybean mature embryo cell, a soybean seed cell, a canola immature embryo cell, a canola mature embryo cell, a canola seed cell, a cotton immature embryo cell, a cotton mature embryo cell, a cotton seed cell, a wheat immature embryo cell, a wheat mature embryo cell, a wheat seed cell, a sugarcane immature embryo cell, a sugarcane mature embryo cell, a sugarcane seed cell.

In one aspect, transformation of a plant cell is performed by an *Agrobacterium* or other Rhizobiales-mediated method (U.S. Pat. Nos. 6,265,638, 5,731,179; U.S. Patent Application Publications US2005/0183170; 2003110532). The polynucleotide sequences that can be transferred into a plant cell provided herein can be present on one recombination vector in one bacterial strain being utilized for transformation. In another aspect, the polynucleotide sequences provided herein can be present on separate recombination vectors in one bacterial strain. In yet another aspect, the polynucleotide sequences provided herein can be found in separate bacterial cells or strains used together for transformation.

The DNA constructs used for transformation in the methods of present disclosure generally also contain the plasmid backbone DNA segments that provide replication function and antibiotic selection in bacterial cells, for example, an *Escherichia coli* origin of replication such as ori322, an *Agrobacterium* origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, LBA4404, AGL0, AGL1, EHA101, or EHA105 carrying a plasmid having a transfer function for the expression unit. Other strains known to those skilled in the art of plant transformation can function in this disclosure.

To confirm the presence of integrated DNA in a transformed cell or genome a variety of assays can be performed. Such assays include, for example, molecular biological assays (e.g., Southern and northern blotting, PCR™); biochemical assays, such as detecting the presence of a protein product (e.g., by immunological means (ELISAs and western blots), or by enzymatic function (e.g., GUS assay)); pollen histochemistry; plant part assays, (e.g., leaf or root assays); and also, by analyzing the phenotype of the whole regenerated plant.

The instant disclosure also provides a transgenic plant cell comprising a sequence of interest integrated into a genome of the plant cell according to the methods disclosed herein. Also provided is a transgenic plant produced by the methods disclosed herein.

EXAMPLES

Example 1. Construct of Control Vectors

Figure 4:
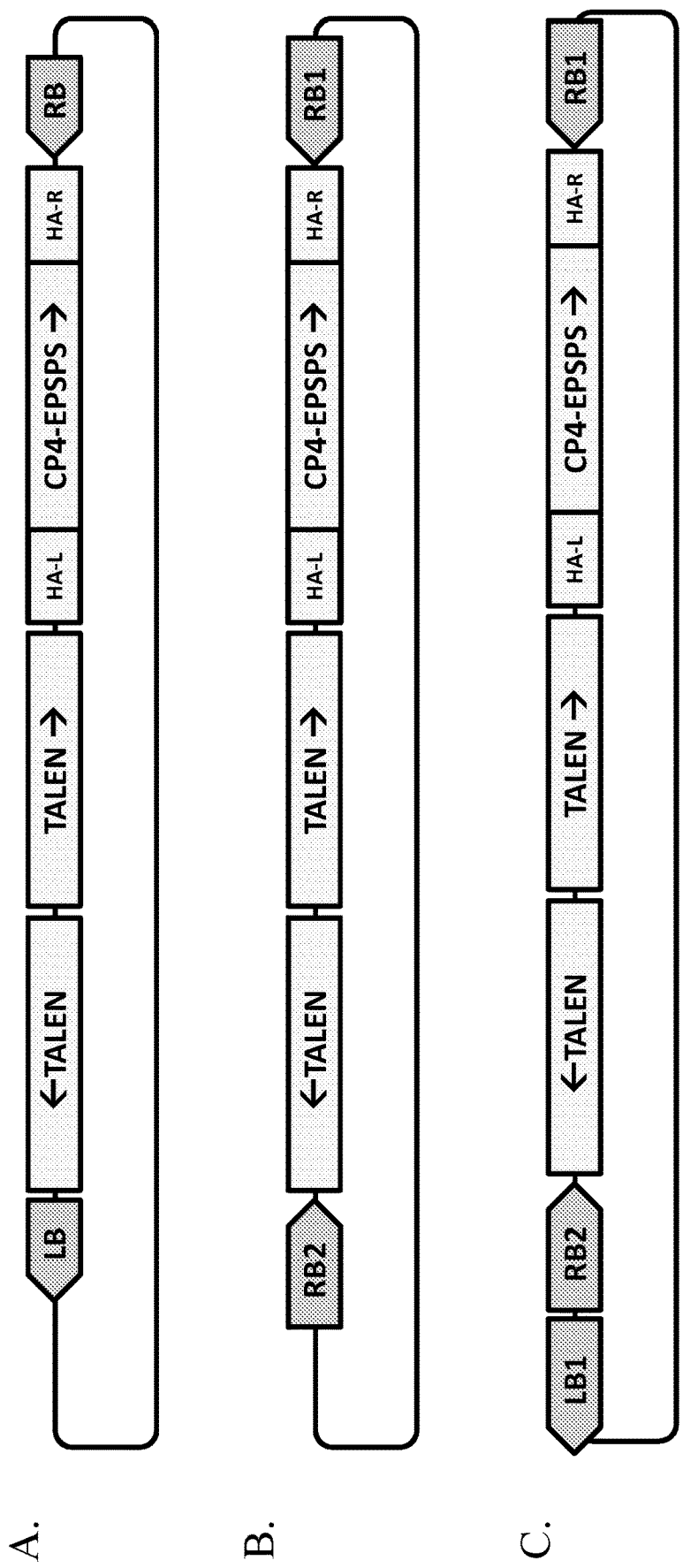
FIG. 4A illustrates a schematic of the control vector configuration for vector A used in Example 9.
FIG. 4B illustrates a schematic of the vector configuration for vector C used in Example 9.
FIG. 4C illustrates a schematic of the vector configuration for vector D used in Example 9.

Two control vectors were created as non-limiting examples for *Agrobacterium*-mediated transformation. Both control vectors contain a sequence of interest comprising three expression cassettes: an expression cassette encoding a gene (CP4-EPSPS) to confer tolerance to the herbicide glyphosate positioned between a left homology arm and a right homology arm; and two expression cassettes each encoding half of a TALEN pair. TALENs were obtained from Life Technologies. The first control vector comprised a RB DNA sequence, the sequence of interest comprising the three expression cassettes, and a LB DNA sequence, as illustrated in FIG. 4A. The second control vector was the same as the first control vector except that there was no LB DNA sequence. These two control vectors were used in Example 9, below.

Example 2. Construct of a Vector with Two RB DNA Sequences

A vector comprising two RB DNA sequences, and zero LB DNA sequences, was created for *Agrobacterium*-mediated transformation (FIG. 4B). The vector was constructed to contain a sequence of interest comprising three expression cassettes: one expression cassette encoding a gene (CP4-EPSPS) to confer tolerance to the herbicide glyphosate positioned between a left homology arm and a right homology arm; and two expression cassettes each encoding half of a TALEN pair; and two RB DNA sequences (RB1 and RB2). This vector was used in Example 9 below. The vector configuration comprised the first RB DNA sequence (RB1) positioned in the vector to initiate synthesis of a first T-strand comprising the three expression cassettes (CP4-EPSPS and two TALENs); and the second RB DNA sequence (RB2) was positioned in the vector to initiate synthesis of a second T-strand comprising the three expression cassettes (CP4-EPSPS and two TALENs) such that the second T-strand was in an anti-sense orientation relative to the first T-strand. The two T-strands resulting from initiation at RB1 and RB2 are essentially complementary to each other in at least a portion of the sequence of interest.

Example 3. Construct of a Vector with Two RB DNA Sequences and One LB DNA Sequence A vector comprising two RB DNA sequences, and one LB DNA sequence, was created for *Agrobacterium*-mediated transformation (FIG. 4C). The vector was constructed to contain a sequence of interest comprising three expression cassettes: one expression cassette encoding a gene (CP4-EPSPS) to confer tolerance to the herbicide glyphosate positioned between a left homology arm and a right homology arm; and two expression cassettes each encoding half of a TALEN pair; and two right border DNA sequences (RB1 and RB2), and one LB DNA sequence (LB1) paired with the first RB DNA sequence (RB1). The vector configuration comprised the first RB DNA sequence (RB1) positioned in the vector to initiate synthesis of a first T-strand comprising the three expression cassettes (CP4-EPSPS and two TALENs) and terminate synthesis at the first LB DNA sequence (LB1) (paired with RB1); and the second RB DNA sequence (RB2) was positioned in the vector to initiate synthesis of a second T-strand comprising the three expression cassettes (CP4-EPSPS and two TALENs) such that the second T-strand was in an anti-sense orientation relative to the first T-strand. This vector was used in Example 9 below. The two T-strands resulting from initiation at RB1 and RB2 are essentially complementary to each other in at least a portion of the sequence of interest.

Example 4. Construct of a Vector with Two RB DNA Sequences and Two LB DNA Sequences A vector comprising at least one sequence of interest, two RB DNA sequences, and two LB DNA sequences is created for *Agrobacterium*-mediated transformation (a non-limiting example is presented in FIG. 1D). The vector configuration comprises a first RB DNA sequence (RB1) paired with a first LB DNA sequence (LB1) which are positioned in the vector to initiate (RB1) and terminate (LB1) synthesis of a first T-strand such that the sequence of interest is in the sense orientation from the 5' to 3' end of the first T-strand; and the second RB DNA sequence (RB2) is paired with a second LB DNA sequence (LB2) which are positioned in the vector to initiate synthesis of a second T-strand such that the sequence of interest is in an anti-sense orientation relative to the sequence of interest in the first T-strand. The two T-strands resulting from initiation at RB1 and RB2 are essentially complementary to each other in at least a portion of the sequence of interest.

Example 5. Construct of a Vector with Two RB DNA Sequences and Two Essentially Identical Sequences of Interest A vector comprising two essentially identical sequences of interest, at least two RB DNA sequences, and optional one or more LB DNA sequences is created for *Agrobacterium*-mediated transformation (a non-limiting example is presented in FIG. 2A). The vector configuration comprises a first RB DNA sequence (RB1) with an optional first LB DNA sequence (LB1) which are positioned in the vector to initiate (RB1) and terminate (LB1) synthesis of a first T-strand such that the first sequence of interest is in the sense orientation from the 5' to 3' end of the first T-strand; and the vector configuration further comprises a second RB DNA sequence (RB2) and an optional second LB DNA sequence (LB2) which are positioned in the vector to initiate (RB2) and terminate (LB2) synthesis of a second T-strand such that the second sequence of interest is in an anti-sense orientation relative to the sequence of interest in the first T-strand. The two T-strands resulting from initiation at RB1 and RB2 are essentially complementary to each other in at least a portion of the sequence of interest.

Example 6. Construct of Two Vectors for Co-Transformation

Figure 2:
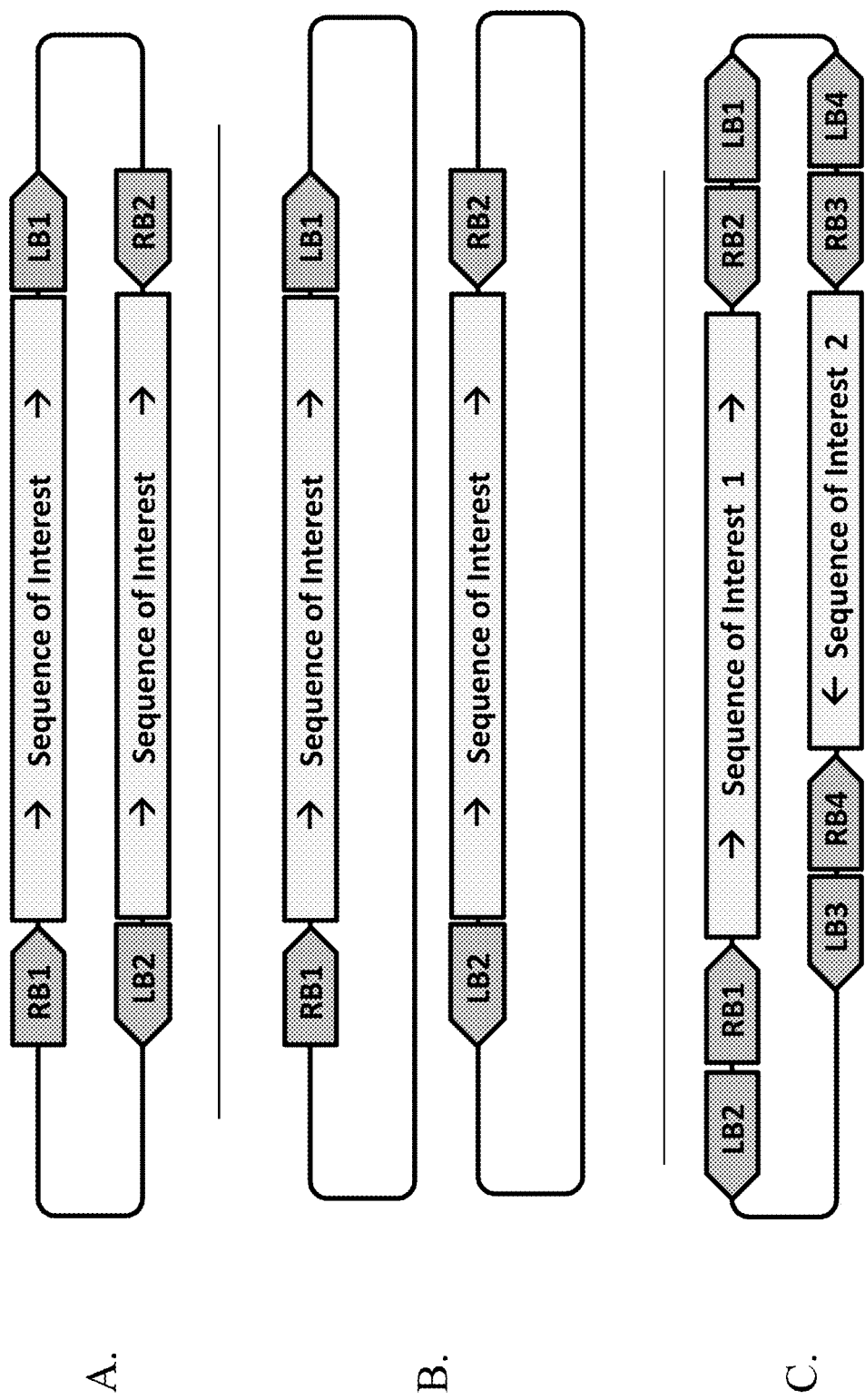
FIG. 2A illustrates a vector configuration comprising a first sequence of interest and a second sequence of interest, where the first sequence of interest is essentially identical to the second sequence of interest; and the vector configuration further comprises a first RB DNA sequence (RB1) with an optional first LB DNA sequence (LB1) which are positioned in the vector to initiate (RB1) and optionally terminate (LB1) synthesis of a first T-strand such that the sequence of interest is in the sense orientation from the 5' to 3' end of the first T-strand; and the vector configuration further comprises a second RB DNA sequence (RB2) and an optional second LB DNA sequence (LB2) which are positioned in the vector to initiate (RB2) and optionally terminate (LB2) synthesis of a second T-strand such that the sequence of interest is in an anti-sense orientation from the 5' to 3' end of the second T-strand. The sequence of interest in the two T-strands resulting from initiation at RB1 and RB2 are essentially complementary to each other.
FIG. 2B illustrates a vector configuration employed in co-transformation in which two essentially identical sequences of interest are located on separate vectors, hosted by one or more bacterium cells, and where the first vector configuration comprises a first RB DNA sequence (RB1) and an optional first LB DNA sequence (LB1) which are positioned in the first vector to initiate (RB1) and optionally terminate (LB1) synthesis of a first T-strand such that the sequence of interest is in the sense orientation from the 5' to 3' end of the first T-strand; and the second vector configuration comprises a second RB DNA sequence (RB2) and an optional second LB DNA sequence (LB2) which are positioned in the second vector to initiate (RB2) and optionally terminate (LB2) synthesis of a second T-strand such that the sequence of interest is in an anti-sense orientation from the 5' to 3' end of the second T-strand. The sequence of interest in the two T-strands resulting from initiation at RB1 and RB2 are essentially complementary to each other.
FIG. 2C illustrates a vector comprising a first sequence of interest, a second sequence of interest different from the first sequence of interest, two or more RB DNA sequences, and one or more optional LB DNA sequences. The illustrated construct is one non-limiting example where the vector configuration comprises a first RB DNA sequence (RB1) and an optional first LB DNA sequence (LB1) which are positioned in the vector to initiate (RB1) and optionally terminate (LB1) synthesis of a first T-strand such that the first sequence of interest is in the sense orientation from the 5' to 3' end of the first T-strand; and the vector configuration further comprises a second RB DNA sequence (RB2) and an optional second LB DNA sequence (LB2) which are positioned in the vector to initiate (RB2) and optionally terminate (LB2) synthesis of a second T-strand such that the first sequence of interest is in an anti-sense orientation from the 5' to 3' end of the second T-strand. The two T-strands resulting from initiation at RB1 and RB2 are essentially complementary to each other in at least a portion of the first sequence of interest. The vector configuration further comprises a third RB DNA sequence (RB3) and an optional third LB DNA sequence (LB3) which are positioned in the vector to initiate (RB3) and optionally terminate (LB3) synthesis of a third T-strand such that the second sequence of interest is in the sense orientation from the 5' to 3' end of the third T-strand; and the vector configuration further comprises a fourth RB DNA sequence (RB4) and an optional fourth LB DNA sequence (LB4) which are positioned in the vector to initiate (RB4) and optionally terminate (LB4) synthesis of a fourth T-strand such that the second sequence of interest is in an anti-sense orientation from the 5' to 3' end of the fourth T-strand. The two T-strands resulting from initiation at RB3 and RB4 are essentially complementary to each other in at least a portion of the second sequence of interest.

Two vectors are provided for the co-transformation of plant cells with *Agrobacterium*-mediated transformation (a non-limiting example is presented in FIG. 2B). The two vector configurations comprise essentially identical sequences of interest, where the first vector configuration comprises a first RB DNA sequence (RB1) and an optional first LB DNA sequence (LB1) which are positioned in the first vector to initiate (RB1) and terminate (LB1) synthesis of a first T-strand such that the sequence of interest is in the sense orientation from the 5' to 3' end of the first T-strand; and the second vector configuration comprises a second RB DNA sequence (RB2) and an optional second LB DNA sequence (LB2) which are positioned in the second vector to initiate (RB2) and terminate (LB2) synthesis of a second T-strand such that the sequence of interest is in an anti-sense orientation relative to the sequence of interest in the first T-strand. The two T-strands resulting from initiation at RB1 and RB2 are essentially complementary to each other in at least a portion of the sequence of interest. The two vectors may be in the same *Agrobacterium* cell, or the two vectors may be in different *Agrobacterium* cells.

Example 7. Construct of a Vector with Two Different Sequences of Interest and Three or More RB DNA Sequences A vector comprising a first sequence of interest, a second sequence of interest different from the first sequence of interest, three or more RB DNA sequences, and optional one or more LB DNA sequences is created for *Agrobacterium*-mediated transformation. For illustrative purposes, one non-limiting example of a vector configuration is presented in FIG. 2C where the vector configuration comprises a first RB DNA sequence (RB1) and a first LB DNA sequence (LB1) which are positioned in the vector to initiate (RB1) and terminate (LB1) synthesis of a first T-strand such that the first sequence of interest is in the sense orientation from the 5' to 3' end of the first T-strand; and the vector configuration further comprises a second RB DNA sequence (RB2) and a second LB DNA sequence (LB2) which are positioned in the vector to initiate (RB2) and terminate (LB2) synthesis of a second T-strand such that the first sequence of interest is in an anti-sense orientation relative to the sequence of interest in the first T-strand. The two T-strands resulting from initiation at RB1 and RB2 are essentially complementary to each other in at least a portion of the sequence of interest. The vector configuration further comprises a third RB DNA sequence (RB3) and a third LB DNA sequence (LB3) which are positioned in the vector to initiate (RB3) and terminate (LB3) synthesis of a third T-strand such that the second sequence of interest is in the sense orientation from the 5' to 3' end of the third T-strand; and the vector configuration further comprises a fourth RB DNA sequence (RB4) and a fourth LB DNA sequence (LB4) which are positioned in the vector to initiate (RB4) and terminate (LB4) synthesis of a fourth T-strand such that the second sequence of interest is in an anti-sense orientation relative to the sequence of interest in the third T-strand. The two T-strands resulting from initiation at RB3 and RB4 are essentially complementary to each other in at least a portion of the sequence of interest.

Figure 3:
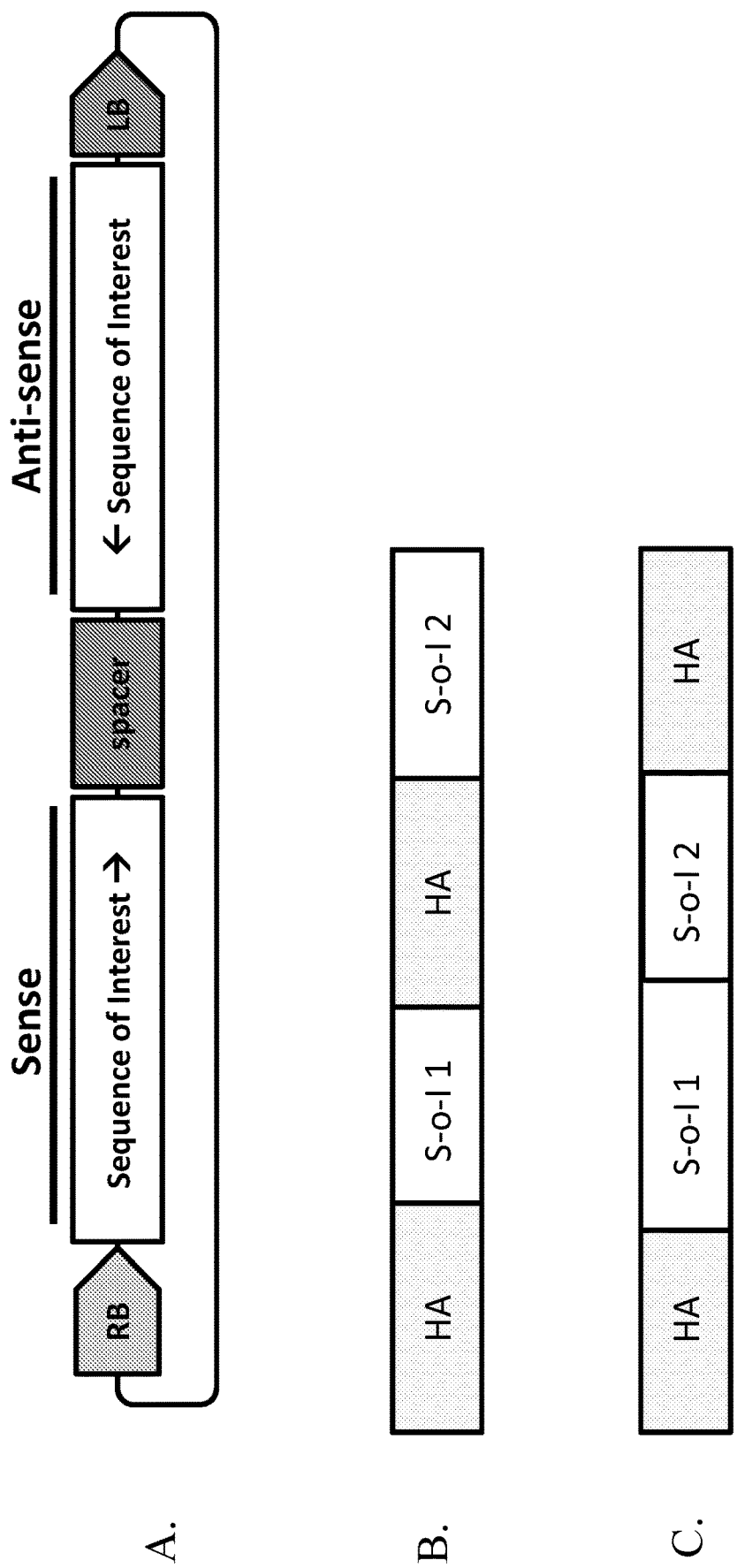
FIG. 3A illustrates a vector configuration where the vector comprises a RB DNA sequence and a LB DNA sequence and where the vector further comprises between the RB and LB DNA sequences: (i) a first sequence of interest in a sense orientation relative to the RB DNA sequence, (ii) a spacer, and (iii) a second sequence of interest in an anti-sense orientation relative to the RB DNA sequence. The two sequences of interest are essentially complementary, and after synthesis of the T-strand a hairpin structure may form.
FIGS. 3B and 3C illustrate possible variations of at least two cassettes (S-o-I 1 and S-o-I 2) in relation to positions of two homology arms within a sequence of interest.

Example 8. Construct of a Vector with a RB DNA Sequence, a LB DNA Sequence, and Two Sequences of Interest Linked by a Spacer A vector is provided for *Agrobacterium*-mediated transformation where the vector configuration comprises a RB DNA sequence and a LB DNA sequence and where the vector further comprises between the RB and LB DNA sequences: (i) a first sequence of interest in a sense orientation relative to the RB DNA sequence, (ii) a spacer, and (iii) a second sequence of interest in an anti-sense orientation relative to the first sequence of interest. The two sequences of interest, after synthesis of the T-strand, form a partially double stranded hairpin structure due to complementary base pairing. For illustrative purposes, one non-limiting example of such a vector configuration is presented in FIG. 3A.

Example 9. Increased Frequency of Site-Directed Integration by *Agrobacterium*-Mediated Transformation A locus termed L7 was identified as occurring only once in a corn genome. A site was selected within the L7 locus for insertion of a transgene by site-directed recombination at the targeted site. To facilitate site-directed recombination a pair of TALENs was engineered to introduce a double-strand break at a specific site within the L7 locus. Vectors made according to Examples 1-3 (see Table 2) were transformed into immature corn embryos. The vectors each comprised a sequence of interest containing three expression cassettes: two expression cassettes for expression of each one of the TALEN pair and an expression cassette containing a CP4-EPSPS transgene positioned between a left homology arm and a right homology arm.

Approximately 3000 immature corn embryos were co-cultured with *Agrobacterium* containing one of the four vectors for 3 days, then moved to callus-induction medium containing 0.1 mM glyphosate as a selection agent. Approximately 300 regenerated plants (R0 events) were selected for each vector, transferred to plugs, and grown in a greenhouse. Genomic DNA was extracted from R0 leaf tissue after one week of greenhouse growth, and individual plants were molecularly assessed with real time PCR for (a) the presence of the transgene (CP4-EPSPS) copy number, and (b) targeting sequence copy number. Individual plants that scored "1" or "2" for transgene copy number (i.e., there are one or two copies of the transgene inserted in the plant genome), or "0" or "1" for targeting sequence copy number (i.e., there is a mutation at the genomic targeting sequence after TALEN enzyme cutting), were selected for additional PCR analysis.

Figure 5:
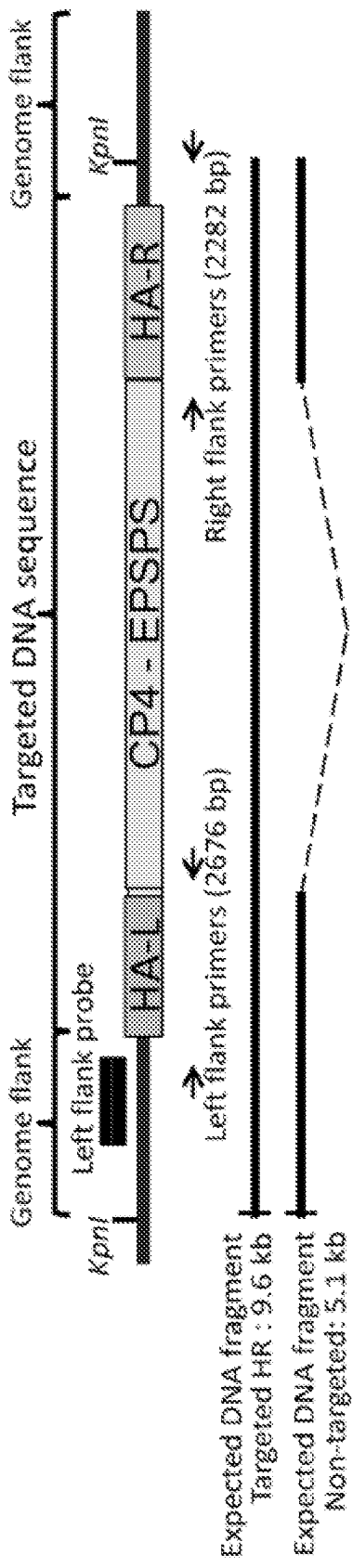
FIG. 5 illustrates the targeted DNA sequence, comprising a left homology arm (HA-L), a selectable marker gene (CP4-EPSPS), and a right homology arm (HA-R), that is used in Example 9.

PCR with genomic DNA from of selected R0 plants was used to identify individual plants comprising CP4-EPSPS cassette insertions at the L7 target site. PCR primers were designed such that a product was only produced when the CP4-EPSPS cassette inserted into the L7 targeted region of the corn genome; one PCR primer was located in genomic DNA flanking the targeted region, and one PCR primer was located within the CP4-EPSPS cassette. Two sets of PCR primers were used, one positioned on the 5' end of the CP4-EPSPS cassette and one positioned on the 3' end of the CP4-EPSPS cassette. FIG. 5 shows the positions of the primers used to identify CP4-EPSPS cassette insertions in the L7 locus. The 5' set of PCR primers amplifies a 2676 bp product when the CP4-EPSPS cassette is inserted in the targeted L7 locus; no product is produced in wild type genomic DNA or if the CP4-EPSPS cassette is not inserted into the L7 target site. The 3' set of PCR primers amplifies a 2282 bp product when the CP4-EPSPS is inserted in the targeted L7 locus; no product is produced in wild type genomic DNA or if the CP4-EPSPS cassette is not inserted into the L7 target site. After PCR, the products were resolved on an agarose gel to identify plants with the correct sized bands for both the 5' end and the 3' end of the CP4-EPSPS cassette. The results of this analysis are shown in Table 2.

To further confirm TALEN-mediated site-directed integration, plants with at least one positive PCR result for site directed insertion of the CP4-EPSPS cassette were selected for Southern blot analysis. Genomic DNA extracted from the plant was digested with the restriction endonuclease KpnI. Digestion with KpnI produces a 9.6 kb fragment when the CP4-EPSPS cassette is integrated into the L7 target site (see FIG. 5). Digestion with KpnI produces a 5.1 kb DNA fragment corresponding to the L7 genomic locus, for example in the wild-type non-transformed plant or a plant where the CP4-EPSPS cassette has not integrated into the L7 locus (see FIG. 5). The Southern blot was probed with a "left flank probe" as shown in FIG. 5. The southern blot results showing a combination of bands of a 9.6 kb (targeted integration) and a 5.1 kb (wild type/non-targeted) indicated that transgenic plants were hemizygous for the CP4-EPSPS cassette (i.e., the CP4-EPSPS cassette was only targeted to one corn chromosome). The southern blot results showing only a band of 9.6 kb (targeted integration) indicated that transgenic plants were homozygous for the CP4-EPSPS cassette (i.e., the CP4-EPSPS cassette was targeted to both corn chromosomes). TALEN-mediated site-directed integration (SDI) using *Agrobacterium* vectors comprising either two RB DNA sequences (vector C) or two RB DNA sequences and one LB DNA sequence (vector D) had superior efficacy compared to standard *Agrobacterium* vectors comprising either one RB DNA sequence and one LB DNA sequence (vector A), or one RB DNA sequence (vector B). The data indicate the unexpected observation of an increased frequency of site-directed integration by NHEJ or HR when the vector comprised two RB DNA sequences positioned to generate essentially complementary T-strands. The data further indicated an increased number of events generated by HR when the vector comprised two RB DNA sequences positioned to generate essentially complementary T-strands (see Table 2).

TABLE 2

Summary of border configurations and site-directed integration (SDI) frequencies.

| Vector | Border configuration | Total embryos transformed | # events | # R0 plants screened by PCR | Flank PCR Left Flank Pos. | Flank PCR Right Flank Pos. | Flank PCR L & R Flank Pos. | SDI positive events by Southern NHEJ or HR | SDI positive events by Southern HR |
|---|---|---|---|---|---|---|---|---|---|
| A | 1 right border (SEQ ID NO: 4) 1 left border (SEQ ID NO: 19) | 2921 | 368 |  | 0 | 1 | 0 | 1 | 0 |
| B | 1 right border (SEQ ID NO: 4) | 3177 | 228 | 68 | 2 | 2 | 2 | 1 | 1 |
| C | 2 right borders (SEQ ID NO: 4) (SEQ ID NO: 4) | 3231 | 336 | 28 | 11 | 7 | 7 | 7 | 4 |
| D | 2 right borders (SEQ ID NO: 4) (SEQ ID NO: 4) 1 left border (SEQ ID NO: 19) | 3544 | 221 | 73 | 8 | 7 | 6 | 8 | 4 |

Pos., positive;
L, left;
R, right;
NHEJ, non-homologous end-joining;
HR, homologous recombination.

Example 10. Retargeting a Gene to a Pre-Existing Lox Site

A vector with two RB DNA sequences is used to facilitate site-directed integration of a sequence of interest into a pre-existing recombination site (e.g. a lox site) in genomic DNA. The vector is created comprising, from 5' to 3', a first right RB DNA sequence (RB1); P-35S-crtB; a first lox site; a gene; a first recombination site (optional); a marker gene to select for transformants; a second recombination site (optional); a second lox site; P-DaMV-Cre; and a second RB DNA sequence (RB2). The RB1 and RB2 are positioned in the vector to generate essentially complementary T-strands. P-35S-crtB is a non-lethal, constitutively expressed phytoene synthase expression cassette that inhibits shoot elongation in cells where non-targeted recombination occurs. P-DaMV-Cre is a constitutively expressed Cre-recombinase that promotes recombination of the intervening DNA construct with the targeted genomic lox site.

Upon creation of a complementary strand of the intervening DNA during *Agrobacterium*-mediated transformation, the lox sites of the intervening DNA recombine with a pre-existing genomic DNA lox site and insert into the genomic DNA. A target after transformation and recombination contains only the regions of the intervening DNA construct between the two lox sites (in this example, a gene; a first recombination site; a marker gene; and a second recombination site). Optional recombination sites are used to remove the marker gene in a future recombination event.

Example 11. Prolonged Co-Culturing During *Agrobacterium*-Mediated Transformation Increases Site-Directed Integration Frequency For transformation of immature corn embryos, *Agrobacterium* containing a vector is typically incubated with the immature corn embryos for 12-16 hours. The unexpected observation detailed herein was that extended co-culture of the *Agrobacterium* containing a vector with the immature corn embryos resulted in a higher percentage of targeted integrations of the sequence of interest contained in the vector while not significantly affecting transformation frequency.

Vector A (FIG. 4A, Example 1) was used for *Agrobacterium*-mediated transformation using standard protocols except that the co-culture time was varied. About 3000 immature corn embryos were co-cultured for each of 1 day, 2 days, or 3 days. After transformation, the transformants were moved to callus-induction medium containing 0.1 mM glyphosate as a selection agent. R0 plants surviving glyphosate selection were transferred to plugs and grown in a greenhouse.

As shown in Table 3, the transformation frequency did not vary significantly between co-culturing periods. The frequency of transformed plants surviving for molecular assessment (91.7% survival for 1 day co-incubation; 91.3% survival for 2 day co-incubation; and 92.8% survival for 3 day co-incubation) shows that prolonged co-culturing did not affect plant health after regeneration from callus. Furthermore, the percentage transformation and the number of plants surviving for molecular assessment was similar for each of the 1 day, 2 day, and 3 day co-culture periods.

TABLE 3

Summary of prolonged co-culture period for *Agrobacterium*-mediated transformation

| Co-culturing Period | Immature Embryos Used | Regenerated Plants | # of Plants Surviving for Molecular Assessment (%) | Percentage Transformed |
|---|---|---|---|---|
| 1 day | 3127 | 205 | 188 (91.7%) | 6.0 |
| 2 day | 3138 | 321 | 293 (91.3%) | 9.3 |
| 3 day | 2920 | 263 | 244 (92.8%) | 8.4 |

After one week of greenhouse growth, R0 leaf tissue was sampled from plants surviving for molecular assessment, and genomic DNA was extracted and assessed for the presence of and copy number of the transgene cassette (CP4-EPSPS), and for targeting sequence copy number with real time PCR. Individual plants that scored "0" or "1" for targeting sequence copy number (i.e., there is a mutation at the genomic target site after TALEN enzyme cutting), or that scored a "1" or "2" for transgene cassette copy number (i.e., there are one or two copies of the transgene cassette inserted in the plant genome) were selected for further PCR analysis. The mutation rate of the targeted site is an indicator of how well the TALEN pair worked in plant cells. The mutation rate can be calculated by assaying the targeting sequence copy number in R0 plants. As shown in Table 4, the mutation rate at the targeted site increased as the co-culturing period was prolonged.

TABLE 4

Mutation rate of each co-culturing period

| Co-culturing period | Surviving R0 plants | R0 plants with mutation at targeted site | Percentage of R0 plants with mutation at targeted site |
|---|---|---|---|
| 1 day | 188 | 96 | 51.1 |
| 2 day | 293 | 162 | 55.3 |
| 3 day | 244 | 149 | 61.1 |

The PCR protocol and primers described in Example 9 were used with the genomic DNA from selected R0 plants from the extended co-culture protocol to identify individual plants comprising targeted integration of the CP4-EPSPS cassette. As described in Example 9, and illustrated in FIG. 5, two sets of PCR primers were used to detect targeted integration of the CP4-EPSPS cassette at the L7 locus. To further verify whether the junction sequences at the targeted sites were perfect (e.g., HR) or imperfect (e.g., NHEJ), the PCR products were sequenced. Table 5 shows that the highest number of positive PCR results for either the left flank, the right flank, or both the left and right flanks was with the 3-day co-culture.

To further confirm the PCR results, R0 plants with at least one positive PCR result were selected for Southern blot analysis, as detailed in Example 9. Genomic DNA extracted from the plant was digested with the restriction endonuclease KpnI, and the southern blots were probed with a left-flank probe (FIG. 5). For each co-culturing period, PCR and Southern blot results detecting targeted integration of the CP4-EPSPS cassette at the L7 locus are summarized in Table 5. The data indicate the unexpected observation of an increased frequency of site-directed integration by NHEJ or HR with the 3-day co-culture. This finding demonstrates that *Agrobacterium*-mediated transformation is more efficient at inducing site-directed integrations in immature corn embryos with prolonged co-culturing periods.

TABLE 5

Summary of left and right flank PCR, southern results and percentage of SDI and HR frequencies in co-culture experiment.

| Co-culturing period | Embryos transformed | # of events | PCR | | | Southern | |
| | | | Left Flank Positive | Right Flank Positive | Right and Left Flank Positive | Targeted (NHEJ or HR) | Targeted (HR only) |
|---|---|---|---|---|---|---|---|
| 1 day | 3127 | 205 | 1 | 0 | 0 | 1 | 0 |
| 2 day | 3138 | 321 | 0 | 0 | 0 | 0 | 0 |
| 3 day | 2920 | 263 | 5 | 6 | 5 | 6 | 3 |

NHEJ, non-homologous end joining;
HR, homologous recombination

Example 12: Increased Frequency of Site-Directed Integration of a Sequence of Interest Flanked by RBs and Optional LBs A site within the L7 locus, described in Example 9, was selected for site-directed integration of a transgene cassette. An expression cassette encoding CP4-EPSPS (CP4-EPSPS), which confers tissue-restricted tolerance to the herbicide glyphosate, was chosen as the cargo for site-specific integration at the L7 locus. To facilitate site-directed integration, a pair of TALENs was engineered to introduce a double-strand break at a specific site within the L7 locus.

Figure 6:
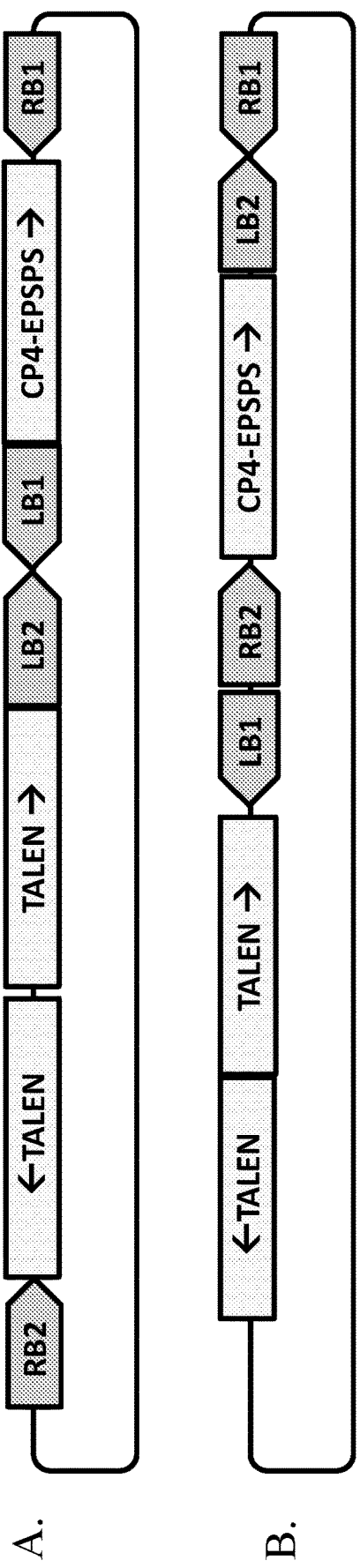
FIG. 6A illustrates a schematic of the configuration of control vector A used in Example 12. Vector A comprises a first sequence of interest comprising an expression cassette encoding CP4-EPSPS positioned between a first RB DNA sequence (RB1) and a first LB DNA sequence (LB1). The vector further comprises a second sequence of interest comprising two expression cassettes each encoding half of a TALEN pair positioned between a second RB DNA sequence (RB2) and a second LB DNA sequence (LB2).
FIG. 6B illustrates a schematic of the configuration of vector B used in Example 12. The vector comprises a first sequence of interest comprising an expression cassette encoding CP4-EPSPS positioned between two RB DNA sequences and two LB DNA sequences. The vector further comprises a second sequence of interest comprising two expression cassettes each encoding half of a TALEN pair.

A control vector (Vector 6A) was created for *Agrobacterium*-mediated transformation (see FIG. 6A). The control vector comprised a first sequence of interest comprising an expression cassette encoding CP4-EPSPS positioned between a first RB DNA sequence (RB1) and a first LB DNA sequence (LB1) such that T-strand synthesis initiated at RB1 and terminated at LB1. The vector further comprised a second sequence of interest comprising two expression cassettes each encoding half of a TALEN pair positioned between a second RB DNA sequence (RB2) and a second LB DNA sequence (LB2) such that T-strand synthesis initiated at RB2 and terminated at LB2. TALENs were obtained from Life Technologies.

A second vector (Vector 6B) was created for *Agrobacterium*-mediated transformation (see FIG. 6B). This vector comprised a first sequence of interest comprising an expression cassette encoding CP4-EPSPS positioned between two RB DNA sequences and two LB DNA sequences. The vector further comprised a second sequence of interest comprising two expression cassettes each encoding half of a TALEN pair. The vector configuration comprised a first RB DNA sequence (RB1) paired with a first LB DNA sequence (LB1) which were positioned in the vector to initiate (RB1) and terminate (LB1) synthesis of a first T-strand comprising CP4-EPSPS in an anti-sense orientation from the 5' to 3' end of the first T-strand; and the second RB DNA sequence (RB2) was paired with a second LB DNA sequence (LB2) which were positioned in the vector to initiate synthesis of 2 were positive for the right flank. For vector 6B, of the 371 R0 plants that were screened by PCR, 2 were positive for the left flank and 10 were positive for the right flank. The data indicated an increased frequency of site directed integration when the vector comprises two RB DNA sequences positioned to generate essentially complementary T-DNA strands containing the cargo sequence to be inserted (Vector 6B).

TABLE 6

Summary of border configurations and site-directed integration frequencies.

| Vector | Border configuration | Total embryos transformed | # events | Flank PCR |  | Left and Right Flank Positive |
|---|---|---|---|---|---|---|
|  |  |  |  | Left Flank Positive | Right Flank Positive |  |
| 6A | 2 right borders (SEQ ID NO: 4) (SEQ ID NO: 12) 2 left borders (SEQ ID NO: 19) (SEQ ID NO: 17) | 3125 | 180 | 0 | 2 | 0 |
| 6B | 2 right borders (SEQ ID NO: 4) (SEQ ID NO: 12) 2 left borders (SEQ ID NO: 19) (SEQ ID NO: 17) | 5445 | 371 | 2 | 10 | 0 | a second T-strand such that CP4-EPSPS was in sense orientation from the 5' to 3' end of the second T-strand. Furthermore, RB1 was also positioned such that read through of the LB1 would result in the synthesis of a T-strand comprising both the CP4-EPSPS cassette and the two TALEN cassettes. The T-strands resulting from initiation at RB1 and RB2 were essentially complementary to each other in at least a portion of the first sequence of interest.

Approximately 3000 to 5000 immature corn embryos were co-cultured with *Agrobacterium* containing either the control Vector 6A or Vector 6B for 3 days, then moved to callus-induction medium containing 0.1 mM glyphosate as a selection agent. One hundred eighty regenerated plants (R0 events) were selected for Vector 6A and 371 regenerated plants were selected for Vector 6B, transferred to plugs, and grown in a greenhouse.

To confirm TALEN mediated site directed integration, genomic DNA was isolated from selected R0 plants and PCR assays were carried out to identify individual plants comprising CP4-EPSPS cassette insertions at the L7 target site. PCR primers were designed such that a product was only produced when the CP4-EPSPS cassette inserted into the L7 target region of the corn genome. PCR protocol and primers described in Example 9, and illustrated in FIG. 5, were used to identify individual plants comprising targeted integration of the CP4-EPSPS cassette. Following PCR, the PCR products were resolved on agarose gels to identify plants with the correct sized bands for both the 5' end and the 3' end of the CP4-EPSPS cassette. As tabulated in Table 6, for the control Vector 6A: of the 180 R0 plants that were screened by PCR, none were positive for the left flank and Example 13: Increased Frequency of Site-Directed Integration of a Sequence of Interest Flanked by RBs and No LBs A site within the L7 locus, described in Example 9, was selected for site-directed integration of a transgene cassette encoding a CP4-EPSPS (CP4-EPSPS), which confers tolerance to the herbicide glyphosate. To facilitate site-directed integration of the cassette, a pair of TALENs was engineered to introduce a double-strand break at a specific site within the L7 locus.

Figure 7:
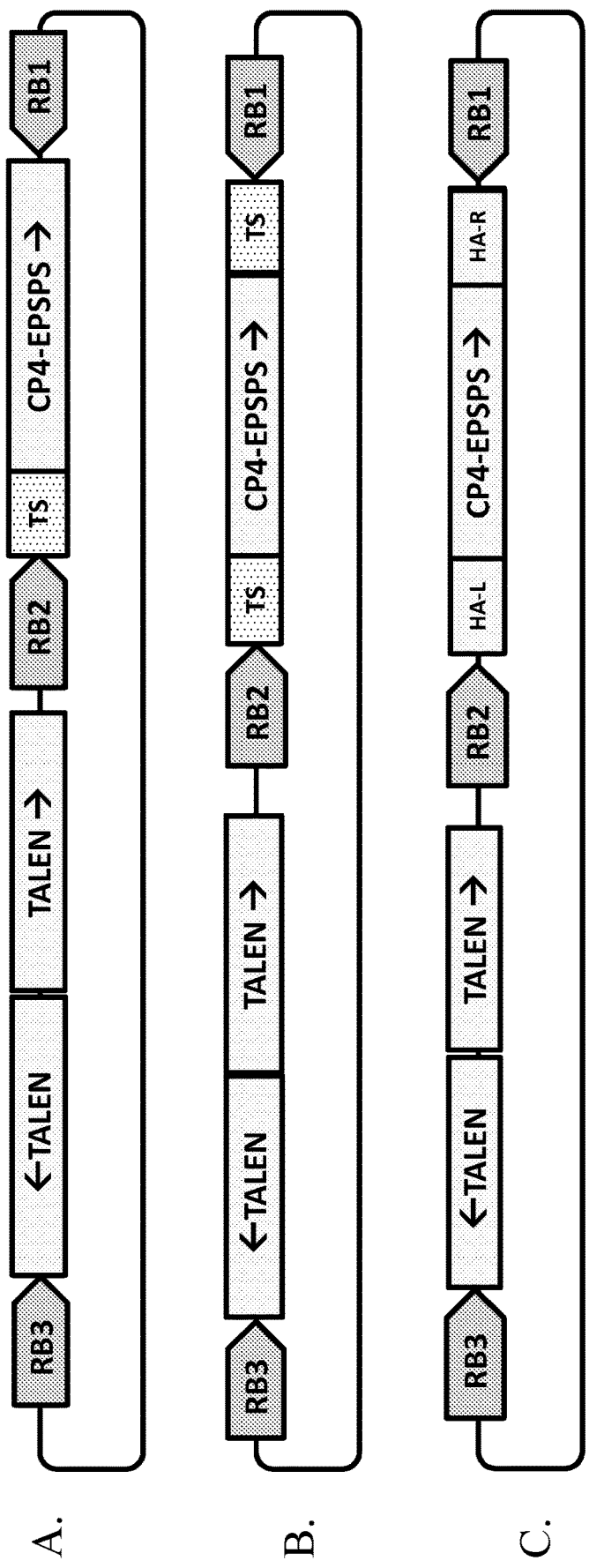
FIG. 7A illustrates a schematic of the configuration of vector A used in Example 13. The vector comprises a first sequence of interest comprising an expression cassette encoding CP4-EPSPS with a TALEN target site (TS) positioned 5' to the CP4-EPSPS cassette. Additionally, the first sequence of interest is flanked by a first RB DNA sequence (RB1) and a second RB DNA sequence (RB2). The vector further comprised a second sequence of interest comprising two expression cassettes each encoding half of a TALEN pair positioned adjacent to a third RB DNA sequence (RB3).
FIG. 7B illustrates a schematic of the configuration of vector B used in Example 13. The vector comprises a first sequence of interest comprising an expression cassette encoding CP4-EPSPS flanked by TALEN target sites. Additionally, the first sequence of interest is flanked by a first RB DNA sequence (RB1) and a second RB DNA sequence (RB2). The vector further comprised a second sequence of interest comprising two expression cassettes each encoding half of a TALEN pair positioned adjacent to a third RB DNA sequence (RB3).
FIG. 7C illustrates a schematic of the configuration of vector C used in Example 13. The vector comprises a first sequence of interest comprising an expression cassette encoding CP4-EPSPS positioned between a left homology arm and a right homology arm. Additionally, the first sequence of interest is positioned between a first RB DNA sequence (RB1) and a second RB DNA sequence (RB2). The vector further comprises a second sequence of interest comprising two expression cassettes each encoding half of a TALEN pair positioned adjacent to a third RB DNA sequence (RB3).

A first vector (Vector 7A) was created for *Agrobacterium*-mediated transformation. For illustrative purposes, the vector configuration is presented in FIG. 7A. The vector comprised a first sequence of interest comprising an expression cassette encoding CP4-EPSPS with a TALEN target site (TS) positioned 5' to the cassette. Additionally, the first sequence of interest was flanked by a first RB DNA sequence (RB1) and a second RB DNA sequence (RB2) positioned such that T-strand synthesis initiated at both RB1 and RB2 and the resulting T-strands were essentially complementary to each other in at least a portion of the first sequence of interest. The vector further comprised a second sequence of interest comprising two expression cassettes each encoding half of a TALEN pair, where the second sequence of interest was positioned adjacent to a third RB DNA sequence (RB3) so as to initiate synthesis of a third T-strand that comprised the two TALEN cassettes. TALENs were obtained from Life Technologies A second vector (Vector 7B) was created for *Agrobacterium*-mediated transformation. For illustrative purposes, the vector configuration is presented in FIG. 7B. The vector comprised a first sequence of interest comprising an expression cassette encoding CP4-EPSPS flanked by TALEN target sites (TS). Additionally, the first sequence of interest was positioned between a first RB DNA sequence (RB1) and a second RB DNA sequence (RB2) such that T-strand synthesis initiated at both RB1 and RB2 and the resulting T-strands were essentially complementary to each other in at least a portion of the first sequence of interest. The vector further comprised a second sequence of interest comprising two expression cassettes each encoding half of a TALEN pair positioned adjacent to a third RB DNA sequence (RB3) so as to initiate synthesis of a third T-strand that comprised the two TALEN cassettes. TALENs were obtained from Life Technologies.

A third vector (Vector 7C) was created for *Agrobacterium*-mediated transformation. For illustrative purposes, the vector configuration is presented in FIG. 7C. The vector comprised a first sequence of interest comprising an expression cassette encoding CP4-EPSPS positioned between a left homology arm and a right homology arm. Additionally, the first sequence of interest was positioned between a first RB DNA sequence (RB1) and a second RB DNA sequence (RB2) such that T-strand synthesis initiated at both RB1 and RB2 and the resulting T-strands were essentially complementary to each other in at least a portion of the first sequence of interest. The vector further comprised a second sequence of interest comprising two expression cassettes each encoding half of a TALEN pair positioned adjacent to a third RB DNA sequence (RB3) so as to initiate synthesis of a third T-strand that comprised the two TALEN cassettes. TALENs were obtained from Life Technologies.

Approximately 4000 to 5000 immature corn embryos were co-cultured with *Agrobacterium* containing one of the three vectors for 3 days, then moved to callus-induction medium containing 0.1 mM glyphosate as a selection agent. Approximately 200 regenerated plants (R0 events) were selected for each vector, transferred to plugs, and grown in a greenhouse.

To confirm TALEN mediated site directed integration, genomic DNA was isolated from selected R0 plants and PCR assays were carried out to identify individual plants comprising CP4-EPSPS cassette insertions at the L7 target site. PCR primers were designed such that a product was only produced when the CP4-EPSPS cassette inserted into the targeted L7 region of the corn genome. PCR protocol and primers described in Example 9, and illustrated in FIG. 5, were used to identify individual plants comprising targeted integration of the CP4-EPSPS cassette. After PCR, the products were resolved on agarose gels to identify plants with the correct sized bands for both the 5' end and the 3' end of the CP4-EPSPS cassette. As tabulated in Table 7, for Vector 7A: of the 226 R0 plants that were screened by PCR, one was positive for the left flank and 4 were positive for the right flank. For Vector 7B, of the 292 R0 plants that were screened by PCR, 2 were positive for the left flank and 26 were positive for the right flank. One plant was positive for both right and left PCR. For Vector 7C, of the 241 R0 plants that were screened by PCR, 7 were positive for the left flank and 7 were positive for the right flank. Four plants were positive for both right and left flank PCR products.

The data indicate that TALEN-mediated site-directed integration (SDI) using an *Agrobacterium* vector comprising two TALEN target sites and two RB DNA sequences flanking a cargo sequence of interest (Vector 7B) had superior efficacy compared to an *Agrobacterium* vector comprising only 1 target site and two RB DNA sequences flanking the cargo sequence (Vector 7A). The data further indicate an increased number of full integration events generated by HR when the vector comprised a cargo sequence flanked by homology arms and two RB DNA sequences (Vector 7C).

TABLE 7

Summary of border configurations and site-directed integration frequencies.

| Vector | Border configuration | Total embryos transformed | # events | Flank PCR Left Flank Positive | Flank PCR Right Flank Positive | Flank PCR Left and Right Flank Positive |
|---|---|---|---|---|---|---|
| 7A | 3 right borders (SEQ ID NO: 4) (SEQ ID NO: 4) (SEQ ID NO: 12) | 5235 | 226 | 1 | 4 | 0 |
| 7B | 3 right borders (SEQ ID NO: 4) (SEQ ID NO: 4) (SEQ ID NO: 12) | 4709 | 292 | 2 | 26 | 1 |
| 7C | 3 right borders (SEQ ID NO: 4) (SEQ ID NO: 4) (SEQ ID NO: 12) | 4059 | 241 | 7 | 7 | 4 |

Example 14. Co-Culturing Time During *Agrobacterium*-Mediated Transformation Influences Site-Directed Integration Frequency For transformation of immature corn embryos, *Agrobacterium* comprising a transformation vector is typically incubated with immature corn embryos for 12-16 hours. The unexpected observation detailed herein was that prolonging the co-culture time of the *Agrobacterium* comprising a vector with immature corn embryos to three days resulted in a higher number of events that had targeted integration of the sequence of interest contained in the vector.

A vector depicted in FIG. 4A and Example 1 was used for *Agrobacterium*-mediated transformation using standard protocols except that the co-culture time was varied. Explants were co-cultured with *Agrobacterium* for 1, 3, 5, or 7 days. Transformation of immature embryos was conducted on eight different experimental dates. One and three day co-culture treatments were conducted on alternating dates (a total of 4 experimental treatment dates each), and an average of 1086 and 1132 explants were treated per experiment, respectively. Five and seven day treatments were conducted on each of the eight experimental dates, with an average of 558 and 556 explants treated per experiment, respectively. After transformation, the transformants were moved to callus-induction medium containing 0.1 mM glyphosate as a selection agent. R0 plants surviving glyphosate selection were transferred to plugs and grown in a greenhouse. The number of stable herbicide tolerant events generated per experimental treatment was divided by the number of explants treated to determine transformation frequencies. PCR protocol and primers described in Example 9 were used with the genomic DNA from R0 plants from the extended co-culture protocol to identify individual plants comprising targeted integration of the CP4-EPSPS cassette. As described in Example 9, and illustrated in FIG. 5, two sets of PCR primers were used to detect targeted integration of the CP4-EPSPS cassette at the L7 locus. The number of site directed integration events (determined by positive flank PCR results for either or both flanks) detected per experimental treatment was divided by the number of explants recovered to estimate the SDI frequencies. The data were analyzed using a mixed linear model. Table 8 shows that the highest number of positive PCR results for either the left flank, the right flank, or both the left and right flanks was with the 3-day co-culture.

TABLE 8

Summary of left and right flank PCR, transformation frequency and percentage of SDI in co-culture experiment.

| Co-culturing period | Embryos transformed | # of events | TFN Freq (%) | PCR Left or Right Flank Pos. (SDI events) | SDI (%) | Right and Left Flank Pos. |
|---|---|---|---|---|---|---|
| 1 day | 4345 | 387 | 8.9 | 8 | 2.1 | 1 |
| 3 day | 4530 | 527 | 11.6 | 21 | 4.0 | 3 |
| 5 day | 4478 | 222 | 5.0 | 10 | 4.5 | 1 |
| 7 day | 4455 | 126 | 2.8 | 6 | 4.8 | 0 |

TFN, Transformation;
Pos., positive;
SDI, site-directed integration

What is claimed is:

1. A method of providing a sequence of interest to the genome of a plant cell, comprising contacting the plant cell with a Rhizobiales cell capable of transforming the plant cell,
wherein the Rhizobiales cell comprises at least one vector capable of forming two T-strands that are essentially complementary in at least a portion of the T-strands,
wherein the at least one vector comprises a first right border DNA sequence (RB1), a second right border DNA sequence (RB2), and at least one sequence of interest,
wherein the RB1 is positioned in the vector to initiate synthesis of a first T-strand such that the sequence of interest is in the sense orientation from the 5' to 3' end of the first T-strand; and the RB2 is positioned in the vector to initiate synthesis of a second T-strand such that the sequence of interest is in the anti-sense orientation relative to the sequence of interest in the first T-strand, and wherein the two T-strands resulting from initiation at RB1 and RB2 are essentially complementary in at least a portion of the sequence of interest, wherein the sequence of interest further comprises at least one homology arm DNA sequence, wherein the at least one homology arm DNA sequence comprises a sequence that is at least 80% identical to a target sequence in the plant genome and is at least 50 nucleotides in length, and
wherein the at least one vector does not comprise a left border DNA sequence.

2. The method of claim 1, wherein
(a) the RB1 and the RB2 are essentially homologous; or
(b) the RB1 and the RB2 are not essentially homologous.

3. The method of claim 1, wherein
(a) at least one of the RB1 and RB2 comprise an *Agrobacterium* Ti plasmid right border consensus DNA sequence;
(b) at least one of the RB1 and RB2 comprise an *Agrobacterium* Ti plasmid right border consensus DNA sequence selected from SEQ ID NO: 21 and SEQ ID NO: 22;
(c) at least one of the RB 1 and RB2 comprise a sequence selected from SEQ ID NOs: 1-13;
or
(d) at least one of the RB1 and RB2 comprise a sequence at least 80% identical to a sequence selected from SEQ ID NO:4 and SEQ ID NO: 12.

4. The method of claim 1, wherein the sequence of interest comprises one or more sequences selected from: a gene, a portion of a gene, an intergenic sequence, an enhancer, a promoter, an intron, an exon, a sequence encoding a transcription termination sequence, a sequence encoding a chloroplast targeting peptide, a sequence encoding a mitochondrial targeting peptide, an insulator sequence, a sequence encoding an anti-sense RNA construct, a sequence encoding a protein, a sequence encoding non-protein-coding RNA (npcRNA), a sequence encoding a recombinase, a sequence encoding a recombinase recognition site, a landing pad, an editing template, an expression cassette, a stack of two or more expression cassettes encoding transgenes, a sequence encoding a site-specific enzyme, a sequence encoding a site-specific enzyme target site, a sequence encoding a selection marker, a sequence encoding a cell factor that functions to increase DNA repair, a sequence comprising a linker or a spacer, a sequence comprising one or more restriction enzyme sites, a sequence for templated genome editing, and any combination thereof.

5. The method of claim 1, wherein the sequence of interest comprises both a left homology arm DNA sequence and a right homology arm DNA sequence.

6. The method of claim 4, wherein the site-specific enzyme is selected from a group consisting of an endonuclease, a recombinase, and a transposase.

7. The method of claim 4, wherein the sequence of interest comprises a sequence encoding a protein involved in DNA repair, wherein the protein is selected from the group comprising a vir gene from the Ti plasmid, Rad51, Rad52, Rad2, a dominant-negative Ku70, or any combination thereof.

8. The method of claim 1, wherein at least part of the sequence of interest is integrated into the plant genome via homologous recombination or via non-homologous end joining, wherein the integration of at least part of the sequence of interest results in a point mutation, an insertion, a deletion, an inversion, increased transcription of an endogenous locus, decreased transcription of an endogenous locus, altered protein activity, altered RNAi products, altered RNAi target sites, altered RNAi pathway activity, increased transcription of the sequence of interest, decreased transcription of the integrated sequence of interest, or any combination thereof.

9. A method of providing at least two sequence of interest to the genome of a plant cell, comprising contacting the plant cell with a Rhizobiales cell capable of transforming the plant cell, wherein the Rhizobiales cell comprises at least one vector comprising a single DNA segment comprising a first right border DNA sequence (RB1) and a second right border DNA sequence (RB2) and wherein the vector comprises between the RB1 and RB2: (i) a first sequence of interest in a sense orientation relative to the RB1, (ii) a spacer, and (iii) a second sequence of interest in an anti-sense orientation relative to the RB 1, wherein the first sequence of interest and second sequence of interest are essentially complementary and after synthesis of the T-strand anneal to form a double-stranded DNA, wherein the sequence of interest further comprises at least one homology arm DNA sequence, wherein the at least one homology arm DNA sequence comprises a sequence that is at least 80% identical to a target sequence in the plant genome and is at least 50 nucleotides in length, and wherein the vector does not comprise a left border DNA sequence.

10. The method of claim 9, wherein the first sequence of interest comprises a first left homology arm DNA sequence and a first right homology arm DNA sequence, and the second sequence of interest comprises a second left homology arm DNA sequence and a second right homology arm DNA sequence.

11. The method of claim 1, wherein the Rhizobiales cell is selected from an *Agrobacterium* spp., a *Bradyrhizobium* spp., a *Mesorhizobium* spp., an *Ochrobactrum* spp., a *Phyllobacterium* spp., a *Rhizobium* spp., and a *Sinorhizobium* spp.

12. The method of claim 1, wherein the plant cell is selected from the group consisting of a corn cell, a soybean cell, a canola cell, a cotton cell, a wheat cell, or a sugarcane cell.

13. A method of providing a sequence of interest to a plant genome, comprising contacting at least one plant cell on a co-culture medium for at least 2 days, with at least one Rhizobiales cell capable of transforming the plant cell, wherein the Rhizobiales cell comprises at least one vector capable of forming two essentially complementary T-strands, wherein, the at least one vector comprises a first right border (RB1) DNA sequence, a second right border DNA sequence (RB2), and at least one sequence of interest, and wherein the RB1 is positioned in the vector to initiate synthesis of a first T-strand such that the sequence of interest is in the sense orientation from the 5' to 3' end of the first T-strand;

and the RB2 is positioned in the vector to initiate synthesis of a second T-strand such that the sequence of interest is in the anti-sense orientation relative to the sequence of interest in the first T-strand, and wherein the sequence of interest in the two T-strands resulting from initiation at RB1 and RB2 are essentially complementary in at least a portion of the sequence of interest, and wherein the sequence of interest further comprises at least one homology arm DNA sequence, wherein the at least one homology arm DNA sequence comprises a sequence that is at least 80% identical to a target sequence in the plant genome and is at least 50 nucleotides in length, and wherein the vector does not comprise a left border DNA sequence.

14. The method of claim 13, wherein the contacting comprises co-culturing the plant cell with the Rhizobiales cell for at least 3 days.

15. The method of claim 13, wherein the Rhizobiales cell is selected from the group consisting of an *Agrobacterium* spp. cell, a *Bradyrhizobium* spp. cell, a *Mesorhizobium* spp. cell, an *Ochrobactrum* spp. cell, a *Phyllobacterium* spp. cell, a *Rhizobium* spp. cell, and a *Sinorhizobium* spp. cell.

16. The method of claim 13, wherein the plant cell is selected from the group consisting of a corn immature embryo cell, a corn mature embryo cell, a corn seed cell, a soybean immature embryo cell, a soybean mature embryo cell, a soybean seed cell, a canola immature embryo cell, a canola mature embryo cell, a canola seed cell, a cotton immature embryo cell, a cotton mature embryo cell, a cotton seed cell, a wheat immature embryo cell, a wheat mature embryo cell, a wheat seed cell, a sugarcane immature embryo cell, a sugarcane mature embryo cell, and a sugarcane seed cell.

\* \* \* \* \*

SEQUENCE LISTING

<160> NUMBER OF SEQ ID NOS: 24

<210> SEQ ID NO 1
<211> LENGTH: 355
<212> TYPE: DNA
<213> ORGANISM: Agrobacterium tumefaciens

<400> SEQUENCE: 1

```
aggatttttc ggcgctgcgc tacgtccgck accgcgttga gggatcaagc cacagcagcc      60
cactcgacct ctagccgacc cagacgagcc aagggatctt tttggaatgc tgctccgtcg     120
tcaggctttc cgacgtttgg gtggttgaac agaagtcatt atcgtacgga atgccaagca     180
ctcccgaggg gaaccctgtg gttggcatgc acatacaaat ggacgaacgg ataaaccttt     240
tcacgccctt ttaaatatcc gttattctaa taaacgctct tttctcttag gtttacccgc     300
caatatatcc tgtcaaacac tgatagttta aactgaaggc gggaaacgac aatct         355
```

<210> SEQ ID NO 2
<211> LENGTH: 356
<212> TYPE: DNA
<213> ORGANISM: Agrobacterium tumefaciens

<400> SEQUENCE: 2

```
aggatttttc ggcgctgcgc tacgtccgck accgcgttga gggatcaagc cacagcagcc      60
cactcgacct ctagccgacc cagacgagcc aagggatctt tttggaatgc tgctccgtcg     120
tcaggctttc cgacgtttgg gtggttgaac agaagtcatt atcgcacgga atgccaagca     180
ctcccgaggg gaaccctgtg gttggcatgc acatacaaat ggacgaacgg ataaaccttt     240
tcacgccctt ttaaatatcc gattattcta ataaacgctc ttttctctta ggtttacccg     300
ccaatatatc ctgtcaaaca ctgatagttt aaactgaagg cgggaaacga caatct        356
```

<210> SEQ ID NO 3
<211> LENGTH: 355
<212> TYPE: DNA
<213> ORGANISM: Agrobacterium tumefaciens

<400> SEQUENCE: 3

```
aggattttc  ggcgctgaca  ggtccgcgac  cgcgttgagg  gatcaagcca  cagcagccca    60 ctcgacctc  tagccgaccc  agacgagcca  agggatcttt  ttggaatgct  gctccgtcgt   120
caggctttcc  gacgtttggg  tggttgaaca  gaagtcatta  tcgcacggaa  tgccaagcac   180
tcccgagggg  aaccctgtgg  ttggcatgca  catacaaatg  gacgaacgga  taaaccttt    240 cacgcccttt  taaatatccg  attattctaa  taaacgctct  tttctcttag  gtttacccgc   300
caatatatcc  tgtcaaacac  tgatagttta  aactgaaggc  gggaaacgac  aatct        355

<210> SEQ ID NO 4
<211> LENGTH: 505
<212> TYPE: DNA
<213> ORGANISM: Agrobacterium tumefaciens

<400> SEQUENCE: 4
cgaagctcgg  tcccgtgggt  gttctgtcgt  ctcgttgtac  aacgaaatcc  attcccattc    60
cgcgctcaag  atggcttccc  ctcggcagtt  catcagggct  aaatcaatct  agccgacttg   120
tccggtgaaa  tgggctgcac  tccaacagaa  acaatcaaac  aaacatacac  agcgacttat   180
tcacacgagc  tcaaattaca  acggtatata  tcctgccagt  cagcatcatc  acaccaaaag   240
ttaggcccga  atagtttgaa  attagaaagc  tcgcaattga  ggtctacagg  ccaaattcgc   300
tcttagccgt  acaatattac  tcaccggtgc  gatgcccccc  atcgtaggtg  aaggtggaaa   360
ttaatgatcc  atcttgagac  cacaggccca  caacagctac  cagtttcctc  aagggtccac   420
caaaaacgta  agcgcttacg  tacatggtcg  ataagaaaag  gcaatttgta  gatgttaaca   480
tccaacgtcg  ctttcaggga  tcctt                                            505

<210> SEQ ID NO 5
<211> LENGTH: 470
<212> TYPE: DNA
<213> ORGANISM: Agrobacterium tumefaciens

<400> SEQUENCE: 5 aggattttc  ggcgctgcgc  tacgtccgcg  accgcgttga  gggatcaagc  cacagcagcc    60
cactcgacct  tctagccgac  ccagacgagc  caagggatct  tttggaatg   ctgctccgtc   120 gtcaggcttt  ccgacgtttg  ggtggttgaa  cagaagtcat  tatcgcacgg  aatgccaagc   180
actcccgagg  ggaaccctgt  ggttggcatg  cacatacaaa  tggacgaacg  gataaacctt   240 ttcacgcccct  tttaaatatc  cgattattct  aataaacgct  ctttctctt  aggtttaccc   300 gccaatatat  cctgtcaaac  actgatagtt  taaactgaag  gcgggaaacg  acaatctgat   360
catgagcgga  gaattaaggg  agtcacgtta  tgaccccgc   cgatgacgcg  ggacaagccg   420 tttacgttt   ggaactgaca  gaaccgcaac  gttgaaggag  ccactgagcc                470

<210> SEQ ID NO 6
<211> LENGTH: 334
<212> TYPE: DNA
<213> ORGANISM: Agrobacterium tumefaciens

<400> SEQUENCE: 6
cgaagctcgg  tcccgtgggt  gttctgtcgt  ctcgttgtac  aacgaaatcc  attcccattc    60
cgcgctcaag  atggcttccc  ctcggcagtt  catcagggct  aaatcaatct  agccgacttg   120
tccggtgaaa  tgggctgcac  tccaacagaa  acaatcaaac  aaacatacac  agcgacttat   180
tcacacgagc  tcaaattaca  acggtatata  tcctgccagt  cagcatcatc  acaccaaaag   240
ttaggcccga  atagtttgaa  attagaaagc  tcgcaattga  ggtctacagg  ccaaattcgc   300
```

```
tcttagccgt acaatattac tcaccggtgc gatg                               334
```

<210> SEQ ID NO 7
<211> LENGTH: 162
<212> TYPE: DNA
<213> ORGANISM: Agrobacterium tumefaciens

<400> SEQUENCE: 7

```
cctgtggttg gcatgcacat acaaatggac gaacggataa accttttcac gcccttttaa    60
atatccgatt attctaataa cgctcttttt ctcttaggtt tacccgccaa tatatcctgt   120
caaacactga tagtttaaac tgaaggcggg aaacgacaat ct                      162
```

<210> SEQ ID NO 8
<211> LENGTH: 329
<212> TYPE: DNA
<213> ORGANISM: Agrobacterium tumefaciens

<400> SEQUENCE: 8

```
aggattttc ggcgctgcgc tacgtccgck accgcgttga gggatcaagc cacagcagcc    60
cactcgacct ctagccgacc cagacgagcc aagggatctt tttggaatgc tgctccgtcg   120
tcaggctttc cgacgtttgg gtggttgaac agaagtcatt atcgtacgga atgccaagca   180
ctcccgaggg gaaccctgtg gttggcatgc acatacaaat ggacgaacgg ataaaccttt   240
tcacgccctt ttaaatatcc gttattctaa taaacgctct tttctcttag gtttacccgc   300
caatatatcc tgtcaaacac tgatagttt                                     329
```

<210> SEQ ID NO 9
<211> LENGTH: 331
<212> TYPE: DNA
<213> ORGANISM: Agrobacterium tumefaciens

<400> SEQUENCE: 9

```
aggattttc ggcgctgcgc tacgtccgck accgcgttga gggatcaagc cacagcagcc    60
cactcgacct tctagccgac ccagacgagc caagggatct ttttggaatg ctgctccgtc   120
gtcaggcttt ccgacgtttg gtggttgaa cagaagtcat tatcgcacgg aatgccaagc   180
actcccgagg ggaaccctgt ggttggcatg cacatacaaa tggacgaacg gataaacctt   240
ttcacgcccct tttaaatatc cgattattct aataaacgct cttttctctt aggtttaccc   300
gccaatatat cctgtcaaac actgatagtt t                                   331
```

<210> SEQ ID NO 10
<211> LENGTH: 331
<212> TYPE: DNA
<213> ORGANISM: Agrobacterium tumefaciens

<400> SEQUENCE: 10

```
aggattttc ggcgctgcgc tacgtccgcg accgcgttga gggatcaagc cacagcagcc    60
cactcgacct tctagccgac ccagacgagc caagggatct ttttggaatg ctgctccgtc   120
gtcaggcttt ccgacgtttg gtggttgaa cagaagtcat tatcgcacgg aatgccaagc   180
actcccgagg ggaaccctgt ggttggcatg cacatacaaa tggacgaacg gataaacctt   240
ttcacgcccct tttaaatatc cgattattct aataaacgct cttttctctt aggtttaccc   300
gccaatatat cctgtcaaac actgatagtt t                                   331
```

<210> SEQ ID NO 11

```
<211> LENGTH: 285
<212> TYPE: DNA
<213> ORGANISM: Agrobacterium tumefaciens

<400> SEQUENCE: 11
cgaagctcgg tcccgtgggt gttctgtcgt ctcgttgtac aacgaaatcc attcccattc      60
cgcgctcaag atggcttccc ctcggcagtt catcagggct aaatcaatct agccgacttg     120
tccggtgaaa tgggctgcac tccaacagaa acaatcaaac aaacatacac agcgacttat     180
tcacacgagc tcaaattaca acggtatata tcctgccagt cagcatcatc acaccaaaag     240
ttaggcccga atagtttgaa attagaaagc tcgcaattga ggtct                     285

<210> SEQ ID NO 12
<211> LENGTH: 357
<212> TYPE: DNA
<213> ORGANISM: Agrobacterium tumefaciens

<400> SEQUENCE: 12 aggattttc ggcgctgcgc tacgtccgcg accgcgttga gggatcaagc cacagcagcc      60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc     180
actcccgagg ggaaccctgt ggttggcatg cacatacaaa tggacgaacg gataaacctt     240
ttcacgcccc tttaaatatc cgattattct aataaacgct cttttctctt aggtttaccc     300
gccaatatat cctgtcaaac actgatagtt taaactgaag gcgggaaacg acaatct       357

<210> SEQ ID NO 13
<211> LENGTH: 330
<212> TYPE: DNA
<213> ORGANISM: Agrobacterium tumefaciens

<400> SEQUENCE: 13 aggattttc ggcgctgcgc tacgtccgck accgcgttga gggatcaagc cacagcagcc      60
cactcgacct ctagccgacc cagacgagcc aagggatctt tttggaatgc tgctccgtcg    120
tcaggctttc cgacgtttgg gtggttgaac agaagtcatt atcgcacgga atgccaagca    180
ctcccgaggg gaaccctgtg gttggcatgc acatacaaat ggacgaacgg ataaacctt     240 tcacgccctt ttaaatatcc gattattcta ataaacgctc ttttctctta ggtttacccg    300
ccaatatatc ctgtcaaaca ctgatagttt                                      330

<210> SEQ ID NO 14
<211> LENGTH: 220
<212> TYPE: DNA
<213> ORGANISM: Agrobacterium tumefaciens

<400> SEQUENCE: 14
taaaaacgtc cgcaatgtgt tattaagttg tctaagcgtc aatttgttta caccacaata     60
tatcctgcca ccagccagcc aacagctccc cgaccggcag ctcggcacaa aatcaccact    120
cgatacaggc agcccatcag tccgggacgg cgtcagcggg agagccgttg taaggcggca    180
gactttgctc atgttaccga tgctattcgg aagaacggca                          220

<210> SEQ ID NO 15
<211> LENGTH: 401
<212> TYPE: DNA
<213> ORGANISM: Agrobacterium tumefaciens

<400> SEQUENCE: 15
```

```
ataaagattt cccaatcaga ataatttgtt tattgctttc ggcctataaa tacggacgga    60
tcgtaatttg tcgttttatc aaaatgcact ttcattctat aataacgctg cggacatcta   120 cattttgaa ttgaaaaaaa attggtaatt actctttctt tttctccata ttgaccatca   180
tactcattgc tgatccatgt agatttcccg gacatgaagc catttacaat tgaatatatc   240
ctgccgccgc tgccgctttg cacccggtgg agcttgcatg ttggtttcta cgcagaactg   300
agccggttag gcagataatt tccattgaga actgagccat gtgcaccttc cccccaacac   360
ggtgagcgac ggggcaacgg agtgatccac atgggacttt t                       401
```

<210> SEQ ID NO 16
<211> LENGTH: 443
<212> TYPE: DNA
<213> ORGANISM: Agrobacterium tumefaciens

<400> SEQUENCE: 16

```
ctcatctaag cccccatttg gacgtgaatg tagacacgtc gaaataaaga tttccgaatt    60
agaataattt gtttattgct ttcgcctata aatacgacgg atcgtaattt gtcgttttat   120
caaaatgtac tttcatttta taataacgct gcggacatct acattttga attgaaaaaa   180 aattggtaat tactctttct ttttctccat attgaccatc atactcattg ctgatccatg   240
tagatttccc ggacatgaag ccatttacaa ttgaatatat cctgccgccg ctgccgcttt   300
gcacccggtg gagcttgcat gttggtttct acgcagaact gagccggtta ggcagataat   360
ttccattgag aactgagcca tgtgcacctt ccccccaaca cggtgagcga cggggcaacg   420
gagtgatcca catggggact ttt                                           443
```

<210> SEQ ID NO 17
<211> LENGTH: 319
<212> TYPE: DNA
<213> ORGANISM: Agrobacterium tumefaciens

<400> SEQUENCE: 17

```
aattcagtac attaaaaacg tccgcaatgt gttattaagt tgtctaagcg tcaatttgtt    60
tacaccacaa tatatcctgc caccagccag ccaacagctc cccgaccggc agctcggcac   120
aaaatcacca ctcgatacag gcagcccatc agtccgggac ggcgtcagcg ggagagccgt   180
tgtaaggcgg cagactttgc tcatgttacc gatgctattc ggaagaacgg caactaagct   240
gccgggtttg aaacacggat gatctcgcgg agggtagcat gttgattgta acgatgacag   300
agcgttgctg cctgtgatc                                                319
```

<210> SEQ ID NO 18
<211> LENGTH: 427
<212> TYPE: DNA
<213> ORGANISM: Agrobacterium tumefaciens

<400> SEQUENCE: 18

```
gacacacaca tcatctcatt gatgcttggt aataattgtc attagattgt ttttatgcat    60
agatgcactc gaaatcagcc aattttagac aagtatcaaa cggatgtgaa ttcagtacat   120
taaaaacgtc cgcaatgtgt tattaagttg tctaagcgtc aatttgttta caccacaata   180
tatcctgcca ccagccagcc aacagctccc cgaccggcag ctcggcacaa atcaccact   240 cgatacaggc agcccatcag tccgggacg cgtcagcggg agagccgttg taaggcggca   300
gactttgctc atgttaccga tgctattcgg aagaacggca actaagctgc cgggtttgaa   360
```

```
acacggatga tctcgcggag ggtagcatgt tgattgtaac gatgacagag cgttgctgcc      420
tgtgatc                                                                427
```

<210> SEQ ID NO 19
<211> LENGTH: 442
<212> TYPE: DNA
<213> ORGANISM: Agrobacterium tumefaciens

<400> SEQUENCE: 19

```
ctcatctaag cccccatttg gacgtgaatg tagacacgtc gaaataaaga tttccgaatt      60
agaataattt gtttattgct ttcgcctata aatacgacgg atcgtaattt gtcgttttat     120
caaaatgtac tttcatttta taataacgct gcggacatct acattttga attgaaaaaa     180 aattggtaat tactctttct ttttctccat attgaccatc atactcattg ctgatccatg     240
tagatttccc ggacatgaag ccatttacaa ttgaatatat cctgccgccg ctgccgcttt     300
gcacccggtg gagcttgcat gttggtttct acgcagaact gagccggtta ggcagataat     360
ttccattgag aactgagcca tgtgcacctt ccccccaaca cggtgagcga cggggcaacg     420
gagtgatcca catgggactt tt                                              442
```

<210> SEQ ID NO 20
<211> LENGTH: 411
<212> TYPE: DNA
<213> ORGANISM: Agrobacterium tumefaciens

<400> SEQUENCE: 20

```
agacacgtcg aaataaagat ttccgaatta gaataatttg tttattgctt tcgcctataa      60
atacgacgga tcgtaatttg tcgttttatc aaaatgtact ttcattttat aataacgctg     120
cggacatcta cattttgaa ttgaaaaaaa attggtaatt actctttctt tttctccata     180
ttgaccatca tactcattgc tgatccatgt agatttcccg gacatgaagc catttacaat     240
tgaatatatc ctgccgccgc tgccgctttg cacccggtgg agcttgcatg ttggtttcta     300
cgcagaactg agccggttag gcagataatt tccattgaga actgagccat gtgcaccttc     360 ccccaacac ggtgagcgac ggggcaacgg agtgatccac atgggacttt t              411
```

<210> SEQ ID NO 21
<211> LENGTH: 25
<212> TYPE: DNA
<213> ORGANISM: Agrobacterium tumefaciens

<400> SEQUENCE: 21

```
gtttacccgc aatatatcc tgtca                                            25
```

<210> SEQ ID NO 22
<211> LENGTH: 25
<212> TYPE: DNA
<213> ORGANISM: Agrobacterium tumefaciens

<400> SEQUENCE: 22

```
aattcaaacg gtatatatcc tgcca                                           25
```

<210> SEQ ID NO 23
<211> LENGTH: 25
<212> TYPE: DNA
<213> ORGANISM: Agrobacterium tumefaciens

<400> SEQUENCE: 23

```
gtttacacca caatatatcc tgcca                                           25
```

```
<210> SEQ ID NO 24
<211> LENGTH: 25
<212> TYPE: DNA
<213> ORGANISM: Agrobacterium tumefaciens

<400> SEQUENCE: 24
atttacaatt gaatatatcc tgccg                                              25
```